(12) United States Patent
Kita et al.

(10) Patent No.: US 6,970,790 B2
(45) Date of Patent: Nov. 29, 2005

(54) METHOD AND APPARATUS FOR ANALYSIS OF MOLECULAR COMBINATION BASED ON COMPUTATIONAL ESTIMATION OF ELECTROSTATIC AFFINITY USING BASIS EXPANSIONS

(75) Inventors: David Kita, Milpitas, CA (US); Somalee Datta, Menlo Park, CA (US); Adityo Prakash, Fremont, CA (US); Eniko Fodor, Fremont, CA (US)

(73) Assignee: Verseon, LLC, Milpitas, CA (US)

( * ) Notice: Subject to any disclaimer, the term of this patent is extended or adjusted under 35 U.S.C. 154(b) by 0 days.

(21) Appl. No.: 10/967,011

(22) Filed: Oct. 14, 2004

(65) Prior Publication Data

US 2005/0119835 A1 Jun. 2, 2005

Related U.S. Application Data

(60) Provisional application No. 60/511,277, filed on Oct. 14, 2003.

(51) Int. Cl.[7] .............................................. C12Q 1/00
(52) U.S. Cl. ........................................ 702/22; 702/19
(58) Field of Search ............................. 702/22, 27–32, 702/19, 21–23

(56) References Cited

U.S. PATENT DOCUMENTS

| | | | | |
|---|---|---|---|---|
| 4,939,666 A | * | 7/1990 | Hardman ................... 700/293 |
| 5,260,882 A | * | 11/1993 | Blanco et al. ................. 703/6 |
| 5,424,963 A | * | 6/1995 | Turner et al. ................... 703/6 |
| 5,495,423 A | * | 2/1996 | DeLisi et al. ................... 703/2 |
| 5,703,792 A | * | 12/1997 | Chapman ..................... 702/27 |
| 5,915,230 A | * | 6/1999 | Berne et al. .................. 702/22 |
| 6,230,102 B1 | * | 5/2001 | Tidor et al. ................... 702/19 |
| 2002/0062155 A1 | * | 5/2002 | Itai et al. ........................ 700/1 |
| 2002/0133298 A1 | * | 9/2002 | Silverman ..................... 702/19 |
| 2005/0027457 A1 | * | 2/2005 | Mandell et al. ............... 702/19 |
| 2005/0027458 A1 | * | 2/2005 | Merz et al. ................... 702/19 |
| 2005/0038610 A1 | * | 2/2005 | Mayo et al. .................. 702/19 |
| 2005/0055165 A1 | * | 3/2005 | Purvis, III .................... 702/19 |

\* cited by examiner

*Primary Examiner*—Marc S. Hoff
*Assistant Examiner*—Anthony Gutierrez
(74) *Attorney, Agent, or Firm*—Townsend and Townsend and Crew LLP; Philip H. Albert

(57) ABSTRACT

A method and apparatus for analysis of molecular combinations featuring two or more molecular subsets is described. The computational method estimates the electrostatic affinity of the system via utilization of a basis expansion representing charge density and electrostatic potential functions associated with the first and second molecular subsets in a coordinate system. An electrostatic affinity, representing a correlation of the charge density and electrostatic potential functions of the first and second molecular subsets, is computed via suitable application of translation and rotation operators to the basis expansion coefficients over a sequence of different sampled configurations for the molecular combination. The method may also be combined with other methods for computation of shape complementarity in determining a composite or augmented score reflecting both electrostatic affinity and shape complementarity for configurations of a molecular combination.

89 Claims, 19 Drawing Sheets

```
                                                              ,-0340
      ┌──────────────────────────────────────────────────────────┐
      │ HEADER   OXIDO-REDUCTASE              25-JUN-82    4DFR  │
      │ COMPND   DIHYDROFOLATE REDUCTASE (E.C.1.5.1.3) COMPLEX WITH │
      │ COMPND  2 METHOTREXATE                                    │
      │ SOURCE   (ESCHERICHIA COLI B), STRAIN /MB1428$,          │
      │ SOURCE  2 A METHOTREXATE-RESISTANT MUTANT                │
      │ AUTHOR  D.J.FILMAN, D.A. MATTHEWS, J.T. BOLIN, J. KRAUT  │
      │ JRNL   AUTH J.T. BOLIN, D.J. FILMAN, D.A. MATTHEWS, R.C. HAMLIN, │
      │ JRNL   AUTH 2 J. KRAUT                                    │
      │ JRNL    REF   J.BIOL.CHEM.        V. 257 13650 1982      │
      │ REMARK 1 RESOLUTION, 1.7                                  │
      │ ANGSTROMS.                                                │
      │ FORMUL 2 MIX  2 (C20 H22 N8 O5)                          │
```

| | | | | | | | |
|---|---|---|---|---|---|---|---|
| HETATM | 1 | N1 | MTX | A | 1 | 22.983 58.667 24.488 | 1.00 15.10 |
| HETATM | 2 | C2 | MTX | A | 1 | 23.468 58.215 23.282 | 1.00 17.30 |
| HETATM | 3 | NA2 | MTX | A | 1 | 24.797 58.223 23.208 | 1.00 16.50 |
| HETATM | 4 | N3 | MTX | A | 1 | 22.792 57.819 22.23 | 1.00 17.90 |
| HETATM | 5 | C4 | MTX | A | 1 | 21.459 57.803 22.068 | 1.00 18.60 |
| HETATM | 6 | NA4 | MTX | A | 1 | 20.821 57.44 21.075 | 1.00 18.10 |
| HETATM | 7 | C4A | MTX | A | 1 | 20.9  58.304 23.363 | 1.00 18.90 |
| HETATM | 8 | N5 | MTX | A | 1 | 19.558 58.514 23.37 | 1.00 19.80 |
| HETATM | 9 | C6 | MTX | A | 1 | 18.989 58.982 24.422 | 1.00 18.60 |
| HETATM | 10 | C7 | MTX | A | 1 | 19.781 59.256 25.628 | 1.00 18.80 |
| HETATM | 11 | N8 | MTX | A | 1 | 21.096 59.176 25.562 | 1.00 21.90 |
| HETATM | 12 | C8A | MTX | A | 1 | 21.608 58.594 24.363 | 1.00 19.50 |
| HETATM | 13 | C9 | MTX | A | 1 | 17.465 59.006 24.451 | 1.00 20.50 |
| HETATM | 14 | N10 | MTX | A | 1 | 16.957 59.967 25.533 | 1.00 17.40 |
| HETATM | 15 | CM | MTX | A | 1 | 16.225 59.184 26.643 | 1.00 22.30 |
| HETATM | 16 | C11 | MTX | A | 1 | 18.122 64.1  25.805 | 1.00 22.10 |
| HETATM | 17 | C12 | MTX | A | 1 | 17.288 63.511 26.732 | 1.00 18.80 |
| HETATM | 18 | C13 | MTX | A | 1 | 16.845 62.195 26.688 | 1.00 18.10 |
| HETATM | 19 | C14 | MTX | A | 1 | 17.32 61.452 25.68 | 1.00 19.70 |
| HETATM | 20 | C15 | MTX | A | 1 | 18.141 62.098 24.672 | 1.00 17.60 |
| HETATM | 21 | C16 | MTX | A | 1 | 18.518 63.414 24.738 | 1.00 17.00 |
| HETATM | 22 | C | MTX | A | 1 | 18.192 65.626 25.834 | 1.00 23.30 |
| HETATM | 23 | O | MTX | A | 1 | 17.516 66.28 26.783 | 1.00 25.90 |
| HETATM | 24 | N | MTX | A | 1 | 19.329 65.981 25.135 | 1.00 21.30 |
| HETATM | 25 | CA | MTX | A | 1 | 19.837 67.459 25.135 | 1.00 22.60 |
| HETATM | 26 | CT | MTX | A | 1 | 20.159 67.548 23.635 | 1.00 22.80 |
| HETATM | 27 | O1 | MTX | A | 1 | 20.289 66.659 22.848 | 1.00 21.30 |
| HETATM | 28 | O2 | MTX | A | 1 | 19.921 68.75  23.149 | 1.00 27.20 |
| HETATM | 29 | CB | MTX | A | 1 | 21.217 67.669 25.761 | 1.00 27.40 |
| HETATM | 30 | CG | MTX | A | 1 | 20.891 67.636 27.32 | 1.00 36.20 |

```
HETATM  31  CD   MTX  A  1    19.921 68.524 28.357 1.00 41.50
HETATM  32  OE1  MTX  A  1    19.413 68.371 29.593 1.00 49.10
HETATM  33  OE2  MTX  A  1    19.441 69.469 27.489 1.00 42.50
CONECT  1   2    12
CONECT  2   1    3    4
CONECT  3   2
CONECT  4   2    5
CONECT  5   4    6    7
CONECT  6   5
CONECT  7   5    8    12
CONECT  8   7    9
CONECT  9   8    10   13
CONECT  10  9    11
CONECT  11  10   12
CONECT  12  1    7    11
CONECT  13  9    14
CONECT  14  13   15   19
CONECT  15  14
CONECT  16  17   21   22
CONECT  17  16   18
CONECT  18  17   19
CONECT  19  14   18   20
CONECT  20  19   21
CONECT  21  16   20
CONECT  22  16   23   24
CONECT  23  22
CONECT  24  22   25
CONECT  25  24   26   29
CONECT  26  25   27   28
CONECT  27  26
CONECT  28  26
CONECT  29  25   30
CONECT  30  29   31
CONECT  31  30   32   33
CONECT  32  31
CONECT  33  31
END
```

```
# MOL2 TOPOLOGY BY PRODRG
# WARNING: THIS FILE IS BUILT FROM A GROMOS TOPOLOGY
# AND MAY NEED FURTHER OPTIMISATION (E.G. AROMATICITY
@<TRIPOS>MOLECULE
      MTX
  56 58  1
     SMALL
    USER_CHARGES

PRODRG MOLECULE

@<TRIPOS>ATOM

1   C7    19.781  59.256  25.628  C.ar  1  MTX  -0.012
 2   N8    21.096  59.176  25.562  N.ar  1  MTX  -0.264
 3   C8A   21.608  58.594  24.363  C.ar  1  MTX   0.195
 4   N1    22.983  58.667  24.488  N.ar  1  MTX  -0.264
 5   C2    23.468  58.215  23.282  C.ar  1  MTX   0.267
 6   NA2   24.797  58.223  23.208  N.2   1  MTX   0.051
 7   HAE   25.253  57.932  22.367  H     1  MTX   0.014
 8   HAD   25.34   58.52   23.994  H     1  MTX   0.014
 9   N3    22.792  57.819  22.23   N.ar  1  MTX  -0.264
10   C4    21.459  57.803  22.068  C.ar  1  MTX   0.195
11   NA4   20.821  57.44   21.075  N.2   1  MTX   0.051
12   HAG   19.821  57.464  21.087  H     1  MTX   0.013
13   HAF   21.304  57.122  20.259  H     1  MTX   0.014
14   C4A   20.9    58.304  23.363  C.ar  1  MTX   0.103
15   N5    19.558  58.514  23.37   N.ar  1  MTX  -0.264
16   C6    18.989  58.982  24.422  C.ar  1  MTX   0.103
17   C9    17.465  59.006  24.451  C.3   1  MTX   0.055
18   N10   16.957  59.967  25.533  N.2   1  MTX   0.104
19   CM    16.225  59.184  26.643  C.3   1  MTX   0.03
20   C14   17.32   61.452  25.68   C.ar  1  MTX   0.103
21   C15   18.141  62.098  24.672  C.ar  1  MTX  -0.012
22   C16   18.518  63.414  24.738  C.ar  1  MTX  -0.013
23   C13   16.845  62.195  26.688  C.ar  1  MTX  -0.012
24   C12   17.288  63.511  26.732  C.ar  1  MTX  -0.012
25   C11   18.122  64.1    25.805  C.ar  1  MTX  -0.001
26   C     18.192  65.626  25.834  C.2   1  MTX   0.261
27   O     17.516  66.28   26.783  O.3   1  MTX  -0.09
28   HAA   16.734  65.73   27.075  H     1  MTX   0.044
29   N     19.329  65.981  25.135  N.2   1  MTX  -0.11
30   CA    19.837  67.459  25.135  C.3   1  MTX   0.098
31   CT    20.159  67.548  23.635  C.2   1  MTX   0.261
```

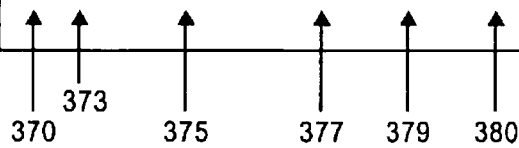

FIG. 3C

|    |      |        |        |        |     |   |     |        |
|----|------|--------|--------|--------|-----|---|-----|--------|
| 32 | O2   | 19.921 | 68.75  | 23.149 | O.2 | 1 | MTX | -0.388 |
| 33 | O1   | 20.289 | 66.659 | 22.848 | O.2 | 1 | MTX | -0.388 |
| 34 | CB   | 21.217 | 67.669 | 25.761 | C.3 | 1 | MTX | 0.055  |
| 35 | CG   | 20.891 | 67.636 | 27.32  | C.3 | 1 | MTX | 0.055  |
| 36 | CD   | 19.921 | 68.524 | 28.357 | C.3 | 1 | MTX | 0.098  |
| 37 | OE2  | 19.441 | 69.469 | 27.489 | O.3 | 1 | MTX | -0.09  |
| 38 | HAC  | 19.949 | 69.421 | 26.629 | H   | 1 | MTX | 0.045  |
| 39 | OE1  | 19.413 | 68.371 | 29.593 | O.3 | 1 | MTX | -0.09  |
| 40 | HAB  | 19.897 | 67.634 | 30.064 | H   | 1 | MTX | 0.045  |
| 41 | H001 | 19.33  | 59.5   | 26.487 | H   | 1 | MTX | 0      |
| 42 | H002 | 17.126 | 58.085 | 24.645 | H   | 1 | MTX | 0      |
| 43 | H003 | 17.125 | 59.306 | 23.56  | H   | 1 | MTX | 0      |
| 44 | H004 | 16.086 | 58.239 | 26.348 | H   | 1 | MTX | 0      |
| 45 | H005 | 16.776 | 59.195 | 27.478 | H   | 1 | MTX | 0      |
| 46 | H006 | 15.339 | 59.611 | 26.824 | H   | 1 | MTX | 0      |
| 47 | H007 | 18.447 | 61.555 | 23.89  | H   | 1 | MTX | 0      |
| 48 | H008 | 19.066 | 63.838 | 24.017 | H   | 1 | MTX | 0      |
| 49 | H009 | 16.211 | 61.825 | 27.367 | H   | 1 | MTX | 0      |
| 50 | H010 | 16.978 | 64.076 | 27.496 | H   | 1 | MTX | 0      |
| 51 | H011 | 19.195 | 68.071 | 25.597 | H   | 1 | MTX | 0      |
| 52 | H012 | 21.607 | 68.55  | 25.491 | H   | 1 | MTX | 0      |
| 53 | H013 | 21.845 | 66.934 | 25.507 | H   | 1 | MTX | 0      |
| 54 | H014 | 21.796 | 67.729 | 27.734 | H   | 1 | MTX | 0      |
| 55 | H015 | 20.557 | 66.703 | 27.454 | H   | 1 | MTX | 0      |
| 56 | H016 | 20.325 | 68.4   | 29.263 | H   | 1 | MTX | 0      |

@<TRIPOS>BOND

| 1  | 1  | 2  | ar |
| 2  | 1  | 16 | ar |
| 3  | 2  | 3  | ar |
| 4  | 3  | 4  | ar |
| 5  | 3  | 14 | ar |
| 6  | 4  | 5  | ar |
| 7  | 5  | 6  | 1  |
| 8  | 5  | 9  | ar |
| 9  | 6  | 7  | 1  |
| 10 | 6  | 8  | 1  |
| 11 | 9  | 10 | ar |
| 12 | 10 | 11 | 1  |
| 13 | 10 | 14 | ar |
| 14 | 11 | 12 | 1  |
| 15 | 11 | 13 | 1  |
| 16 | 14 | 15 | ar |
| 17 | 15 | 16 | ar |

FIG. 3C (CONT.)

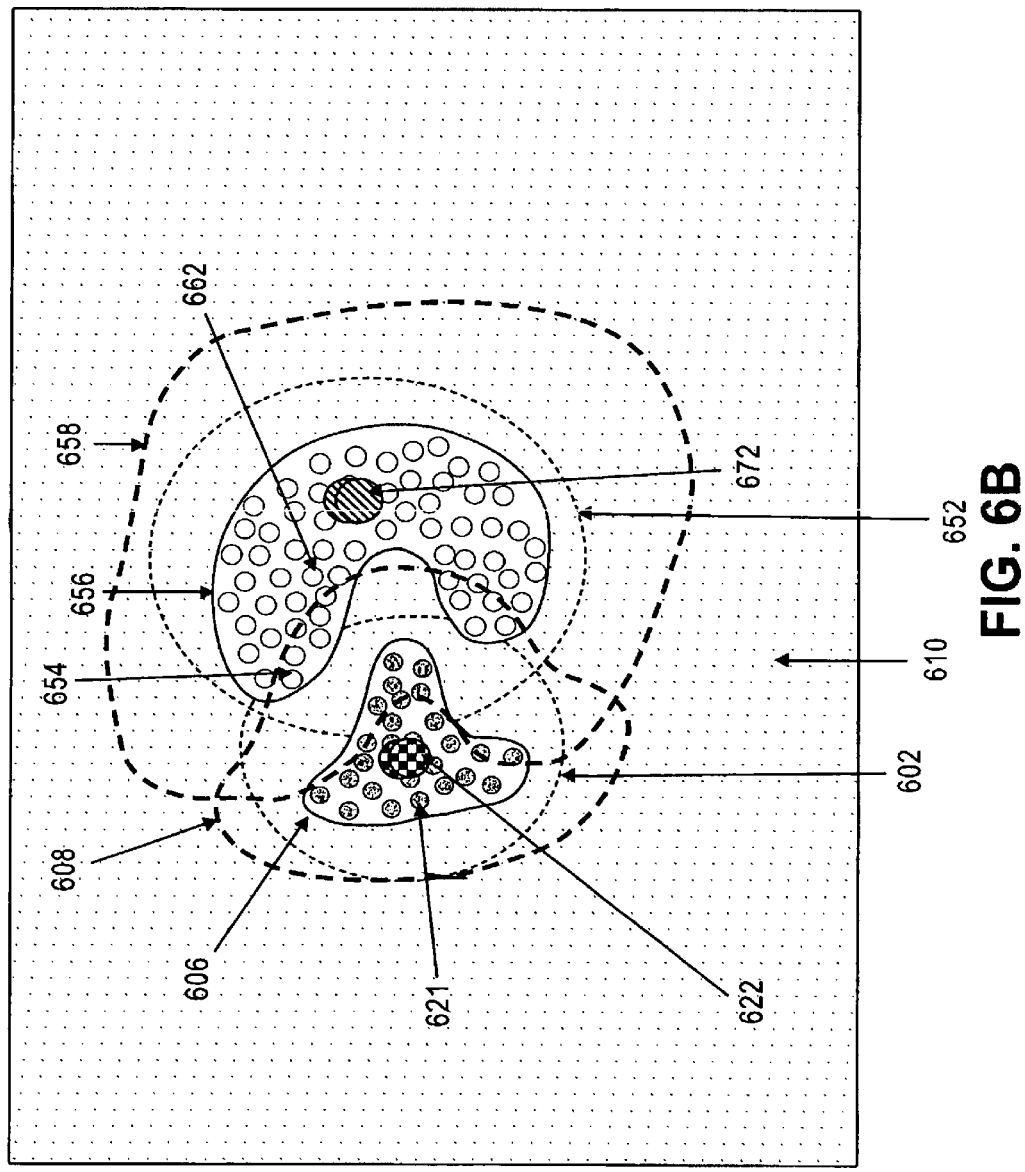

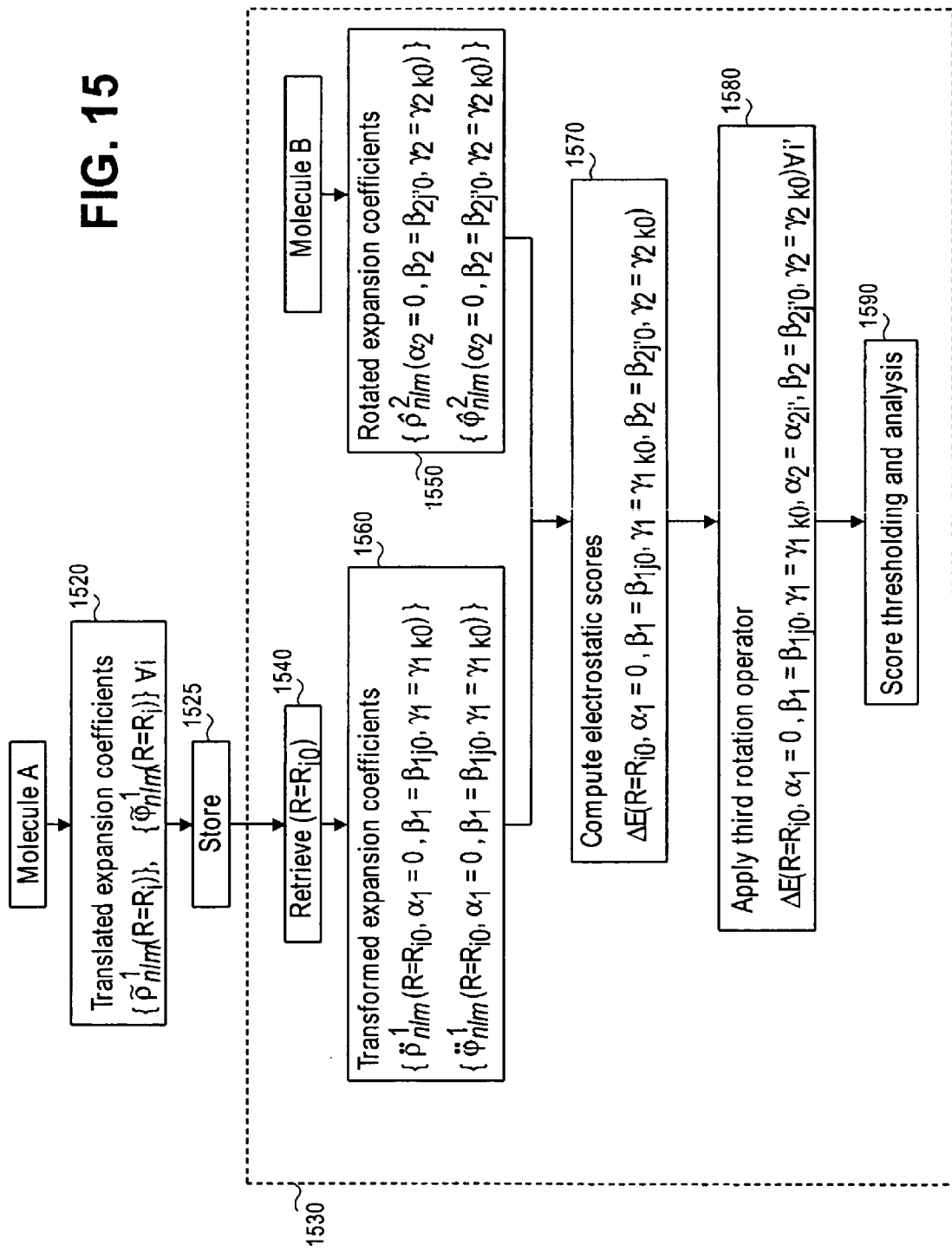

METHOD AND APPARATUS FOR ANALYSIS OF MOLECULAR COMBINATION BASED ON COMPUTATIONAL ESTIMATION OF ELECTROSTATIC AFFINITY USING BASIS EXPANSIONS

CROSS-REFERENCES TO RELATED APPLICATIONS

The present application claims priority from and is a nonprovisional application of U.S. Provisional Application No. 60/511,277, entitled "Method and Apparatus for Estimation of the Electrostatic Affinity Between Molecules using a Basis Expansion" filed Oct. 14, 2003, the entire contents of which are herein incorporated by reference for all purposes.

The present disclosure is related to the following commonly assigned applications/patents:

U.S. patent application Ser. No. 10/966,160; filed of even date herewith, entitled "Method and Apparatus for Analysis of Molecular Combination Based on Computations of Shape Complementarity using Basis Expansions" to Kita et al. (hereinafter "Kita II");

The respective disclosures of these applications/patents are incorporated herein by reference in their entirety for all purposes.

FIELD OF THE INVENTION

The present invention generally relates to bioinformatics, proteomics, molecular modeling, computer-aided molecular design (CAMD), and more specifically computer-aided drug design (CADD) and computational modeling of molecular combinations.

BACKGROUND OF THE INVENTION

An explanation of conventional drug discovery processes and their limitations is useful for understanding the present invention.

Discovering a new drug to treat or cure some biological condition, is a lengthy and expensive process, typically taking on average 12 years and $800 million per drug, and taking possibly up to 15 years or more and $1 billion to complete in some cases.

A goal of a drug discovery process is to identify and characterize a chemical compound or ligand biomolecule, that affects the function of one or more other biomolecules (i.e., a drug "target") in an organism, usually a biopolymer, via a potential molecular interaction or combination. Herein the term biopolymer refers to a macromolecule that comprises one or more of a protein, nucleic acid (DNA or RNA), peptide or nucleotide sequence or any portions or fragments thereof. Herein the term biomolecule refers to a chemical entity that comprises one or more of a biopolymer, carbohydrate, hormone, or other molecule or chemical compound, either inorganic or organic, including, but not limited to, synthetic, medicinal, drug-like, or natural compounds, or any portions or fragments thereof.

The target molecule is typically a disease-related target protein or nucleic acid for which it is desired to affect a change in function, structure, and/or chemical activity in order to aid in the treatment of a patient disease or other disorder. In other cases, the target is a biomolecule found in a disease-causing organism, such as a virus, bacteria, or parasite, that when affected by the drug will affect the survival or activity of the infectious organism. In yet other cases, the target is a biomolecule of a defective or harmful cell such as a cancer cell. In yet other cases the target is an antigen or other environmental chemical agent that may induce an allergic reaction or other undesired immunological or biological response.

The ligand is typically a small molecule drug or chemical compound with desired drug-like properties in terms of potency, low toxicity, membrane permeability, solubility, chemical/metabolic stability, etc. In other cases, the ligand may be biologic such as an injected protein-based or peptide-based drug or even another full-fledged protein. In yet other cases the ligand may be a chemical substrate of a target enzyme. The ligand may even be covalently bound to the target or may in fact be a portion of the protein, e.g., protein secondary structure component, protein domain containing or near an active site, protein subunit of an appropriate protein quaternary structure, etc.

Throughout the remainder of the background discussion, unless otherwise specifically differentiated, a (potential) molecular combination will feature one ligand and one target, the ligand and target will be separate chemical entities, and the ligand will be assumed to be a chemical compound while the target will be a biological protein (mutant or wild type). Note that the frequency of nucleic acids (both DNA/RNA) as targets will likely increase in coming years as advances in gene therapy and pathogenic microbiology progress. Also the term "molecular complex" will refer to the bound state between the target and ligand when interacting with one another in the midst of a suitable (often aqueous) environment. A "potential" molecular complex refers to a bound state that may occur albeit with low probability and therefore may or may not actually form under normal conditions.

The drug discovery process itself typically includes four different subprocesses: (1) target validation; (2) lead generation/optimization; (3) preclinical testing; and (4) clinical trials and approval.

Target validation includes determination of one or more targets that have disease relevance and usually takes two-and-a-half years to complete. Results of the target validation phase might include a determination that the presence or action of the target molecule in an organism causes or influences some effect that initiates, exacerbates, or contributes to a disease for which a cure or treatment is sought. In some cases a natural binder or substrate for the target may also be determined via experimental methods.

Lead generation typically involves the identification of lead compounds that can bind to the target molecule and thereby alter the effects of the target through either activation, deactivation, catalysis, or inhibition of the function of the target, in which case the lead would be a viewed as a suitable candidate ligand to be used in the drug application process. Lead optimization involves the chemical and structural refinement of lead candidates into drug precursors in order to improve binding affinity to the desired target, increase selectivity, and also to address basic issues of toxicity, solubility, and metabolism. Together lead generation and lead optimization typically takes about three years to complete and might result in one or more chemically distinct leads for further consideration.

In preclinical testing, biochemical assays and animal models are used to test the selected leads for various pharmacokinetic factors related to drug absorption, distribution, metabolism, excretion, toxicity, side effects, and required dosages. This preclinical testing takes approximately one year. After the preclinical testing period, clinical trials and approval take another six to eight or more years during which the drug candidates are tested on human subjects for safety and efficacy.

Rational drug design generally uses structural information about drug targets (structure-based) and/or their natural ligands (ligand-based) as a basis for the design of effective lead candidate generation and optimization. Structure-based rational drug design generally utilizes a three-dimensional model of the structure for the target. For target proteins or nucleic acids such structures may be as the result of X-ray crystallography/NMR or other measurement procedures or may result from homology modeling, analysis of protein motifs and conserved domains, and/or computational modeling of protein folding or the nucleic acid equivalent. Model-built structures are often all that is available when considering many membrane-associated target proteins, e.g., GPCRs and ion-channels. The structure of a ligand may be generated in a similar manner or may instead be constructed ab initio from a known 2-D chemical representation using fundamental physics and chemistry principles, provided the ligand is not a biopolymer.

Rational drug design may incorporate the use of any of a number of computational components ranging from computational modeling of target-ligand molecular interactions and combinations to lead optimization to computational prediction of desired drug-like biological properties. The use of computational modeling in the context of rational drug design has been largely motivated by a desire to both reduce the required time and to improve the focus and efficiency of drug research and development, by avoiding often time consuming and costly efforts in biological "wet" lab testing and the like.

Computational modeling of target-ligand molecular combinations in the context of lead generation may involve the large-scale in-silico screening of compound libraries (i.e., library screening), whether the libraries are virtually generated and stored as one or more compound structural databases or constructed via combinatorial chemistry and organic synthesis, using computational methods to rank a selected subset of ligands based on computational prediction of bioactivity (or an equivalent measure) with respect to the intended target molecule.

Throughout the text, the term "binding mode" refers to the 3-D molecular structure of a potential molecular complex in a bound state at or near a minimum of the binding energy (i.e., maximum of the binding affinity), where the term "binding energy" (sometimes interchanged with "binding affinity" or "binding free energy") refers to the change in free energy of a molecular system upon formation of a potential molecular complex, i.e., the transition from an unbound to a (potential) bound state for the ligand and target. Here, the term "free energy" generally refers to both enthalpic and entropic effects as the result of physical interactions between the constituent atoms and bonds of the molecules between themselves (i.e., both intermolecular and intramolecular interactions) and with their surrounding environment. Examples of the free energy are the Gibbs free energy encountered in the canonical or grand canonical ensembles of equilibrium statistical mechanics. In general, the optimal binding free energy of a given target-ligand pair directly correlates to the likelihood of formation of a potential molecular complex between the two molecules in chemical equilibrium, though, in truth, the binding free energy describes an ensemble of (putative) complexed structures and not one single binding mode. However, in computational modeling it is usually assumed that the change in free energy is dominated by a single structure corresponding to a minimal energy. This is certainly true for tight binders (pK~0.1 to 10 nanomolar) but questionable for weak ones (pK~10–100 micromolar). The dominating structure is usually taken to be the binding mode. In some cases it may be necessary to consider more than one alternative-binding mode when the associated system states are nearly degenerate in terms of energy.

It is desirable in the drug discovery process to identify quickly and efficiently the optimal docking configurations, i.e., binding modes, of two molecules or parts of molecules. Efficiency is especially relevant in the lead generation and lead optimization stages for a drug discovery pipeline, where it is desirable to accurately predict the binding mode for possibly millions of potential molecular complexes, before submitting promising candidates to further analysis.

Binding modes and binding affinity are of direct interest to drug discovery and rational drug design because they often help indicate how well a potential drug candidate may serve its purpose. Furthermore, where the binding mode is determinable, the action of the drug on the target can be better understood. Such understanding may be useful when, for example, it is desirable to further modify one or more characteristics of the ligand so as to improve its potency (with respect to the target), binding specificity (with respect to other targets), or other chemical and metabolic properties.

A number of laboratory methods exist for measuring or estimating affinity between a target molecule and a ligand. Often the target might be first isolated and then mixed with the ligand in vitro and the molecular interaction assessed experimentally such as in the myriad biochemical and functional assays associated with high throughput screening. However, such methods are most useful where the target is simple to isolate, the ligand is simple to manufacture and the molecular interaction easily measured, but is more problematic when the target cannot be easily isolated, isolation interferes with the biological process or disease pathway, the ligand is difficult to synthesize in sufficient quantity, or where the particular target or ligand is not well characterized ahead of time. In the latter case, many thousands or millions of experiments might be needed for all possible combinations of the target and ligands, making the use of laboratory methods unfeasible.

While a number of attempts have been made to resolve this bottleneck by first using specialized knowledge of various chemical and biological properties of the target (or even related targets such as protein family members) and/or one or more already known natural binders or substrates to the target, to reduce the number of combinations required for lab processing, this is still impractical and too expensive in most cases. Instead of actually combining molecules in a laboratory setting and measuring experimental results, another approach is to use computers to simulate or characterize molecular interactions between two or more molecules (i.e., molecular combinations modeled in silico). The use of computational methods to assess molecular combinations and interactions is usually associated with one or more stages of rational drug design, whether structure-based, ligand-based, or both.

The computational prediction of one or more binding modes and/or the computational assessment of the nature of a molecular combination and the likelihood of formation of a potential molecular complex is generally associated with the term "docking" in the art. To date, conventional "docking" methods have included a wide variety of computational techniques as described in the forthcoming section entitled "REFERENCES AND PRIOR ART".

Whatever the choice of computational docking method there are inherent trade-offs between the computational complexity of both the underlying molecular models and the intrinsic numerical algorithms, and the amount of compute resources (time, number of CPUs, number of simulations) that must be allocated to process each molecular combination. For example, while highly sophisticated molecular dynamics simulations (MD) of the two molecules surrounded by explicit water molecules and evolved over trillions of time steps may lead to higher accuracy in modeling the potential molecular combination, the resultant computational cost (i.e., time and compute power) is so enormous that such simulations are intractable for use with more than just a few molecular combinations.

One major distinction amongst docking methods as applied to computational modeling of molecular combinations is whether the ligand and target structures remain rigid throughout the course of the simulation (i.e., rigid-body docking) vs. the ligand and/or target being allowed to change their molecular conformations (i.e., flexible docking). In general, the latter scenario involves more computational complexity, though flexible docking may often achieve higher accuracy than rigid-body docking when modeling various molecular combinations.

That being said rigid-body docking can provide valuable insight into the nature of a molecular combination and/or the likelihood of formation of a potential molecular complex and has many potential uses within the context of rational drug discovery. For instance rigid-body docking may be appropriate for docking small, rigid molecules (or molecular fragments) to a simple protein with a well-defined, nearly rigid active site. As another example, rigid-body docking may also be used to more efficiently and rapidly screen out a subset of likely nonactive ligands in a molecule library for a given target, and then applying more onerous flexible docking procedures to the surviving candidate molecules. Rigid-body docking may also be suitable for de novo ligand design and combinatorial library design.

Moreover, in order to better predict the binding mode and better assess the nature and/or likelihood of a molecular combination when one or both molecules are likely to be flexible, rigid-body docking can be used in conjunction with a process for generating likely yet distinct molecular conformers of one or both molecules for straightforward and efficient virtual screening of a molecule library against a target molecule. However, as will be discussed, even rigid body docking of molecular combinations can be computationally expensive and thus there is a clear need for better and more efficient computational methods based on rigid body docking when assessing the nature and/or likelihood of molecular combinations.

As outlined in the section entitled "REFERENCES AND PRIOR ART", conventional computational methods for predicting binding modes and assessing the nature and/or likelihood of molecular combinations in the context of rigid-body docking include a wide variety of techniques. These include methods based on pattern matching (often graph-based), maximization of shape complementarity (i.e., shape correlations), geometric hashing, pose clustering, and even the use of one or more flexible docking methods with the simplifying run-time condition that both molecules are rigid.

Of special interest to this invention is class of rigid-body docking techniques based on the maximization of shape complementarity via evaluation of the spatial correlation between two representative molecular surfaces at different relative positions and orientations. Here the term "shape complementarity" measures the geometric fit or correlation between the molecular shapes of two molecules. The concept can be generalized to any two objects. For example, two pieces of a jigsaw puzzle that fit each other exhibit strong shape complementarity.

Shape complementarity based methods while typically treating molecules as rigid and thus perhaps less rigorous than their flexible docking counterparts, especially in the context of flexible molecules, is still potentially valuable for the fast, efficient screening of two molecules in order to make a preliminary assessment of the nature and/or likelihood of formation of a potential molecular complex of the two molecules or to make an initial prediction of the preferred binding mode for the molecular combination. Such a preliminary assessment may significantly reduce the number of candidates that must be further screened in silico by another more computationally costly docking method.

One example includes the "FTDOCK" docking software of the Cambridge Crystallographic Data Center based on computation of spatial correlations in the Fourier domain and described in Aloy, P., Moont, G., Gabb, H. A., Querol, E., Aviles, F. X., and Sternberg, M. J. E., "Modeling Protein Docking using Shape Complementarity, Electrostatics and Biochemical Information," (1998), *Proteins: Structure, Function, and Genetics,* 33(4) 535–549; all of which is hereby incorporated by reference in their entirety. However, the number of computations associated with this method renders the process impractical for use with conventional computer software and hardware configurations when performing large-scale screening. Moreover, the method is practical for high accuracy prediction of the binding mode due to the requirement of a high resolution of the associated sampling space.

Another example is the Patchdock docking software based on least-square minimization (or equivalent minimization) of separation distances between critical surface and/or fitting points that represent the molecular surfaces of the two molecules and written by Nussinov-Wolfson Structural Bioinformatics Group at Tel-Aviv University, based on principles described in Lin, S. L., Nussinov, R., Fischer, D., and Wolfson, H. J., "Molecular Surface Representations by Sparse Critical Points", *Proteins: Structure, Function, and Genetics* 18, 94–101 (1994); all of which is hereby incorporated by reference in their entirety. However, this method often suffers from degraded accuracy, especially when the molecular surface geometry is complex or when the ligand molecule is very small relative to the protein receptor and/or characterized by poor binding affinities. Moreover, the method can be computationally expensive for a high resolution sampling space of relative positions and orientations of the system, and even the cost of computing the surface critical points is often itself quite expensive.

Yet another example is the "Hex" docking software developed for the efficient estimation of shape complementarity based on the decomposition of two volumetric functions describing a representative molecular surface for each molecule onto an appropriate orthogonal basis set, such as a radial-spherical harmonics expansion. The "Hex" docking software is described in Ritchie, D. W. and Kemp. G. J. L, "Protein Docking Using Spherical Polar Fourier Correlations", (2000), *Proteins: Structure, Function, and Genetics,* 39, 178–194; (hereinafter, "Ritchie et al"), all of which is hereby incorporated by reference in their entirety.

The chief advantage of this type of method is that the required number of calculations scale linearly with the desired number of sampled configurations, thus allowing for a dense sampling of the geometric shape complementarity. Moreover, the compute time is roughly invariant with respect to the sizes of the two molecules and is thus suitable for protein-protein docking as has been demonstrated with respect to multiple protein-protein systems, including both enzyme-inhibitor and antibody-antigen, as shown in Ritchie et al. However, to achieve high accuracy for complex molecular surface geometries, it is necessary to perform the orthogonal basis expansion with a large expansion order and as such the total compute time can be quite large. Furthermore, current methods such as those outlined in Ritchie et al., are not amenable to implementation in customized or other application specific hardware for use in large-scale screening.

While high shape complementarity alone is often a positive indicator of a favorable binding mode, additional electrostatic interactions involving the charges comprising the two molecules, as well as charges or ions in an ambient environment, are also important physical aspects of any potential molecular complex. In fact, many potential molecular combinations involving a false positive lead candidate (i.e., a lead that in reality does not bind strongly to the target) may exhibit high shape complementarity but poor electrostatic affinity. It is also possible, though relatively rare, for a potential molecular combination to demonstrate such a high electrostatic affinity that even if the shape complementarity is relatively poor, the two molecules may indeed have a high likelihood of forming a valid molecular complex. Further discussion of the importance of electrostatic interactions in biology and chemistry can be found in the review article by Honig et al. [35].

Throughout the description the term "charge" will refer to either the conventional definition related to the "net charge" of an molecular component, i.e., its electrostatic monopole moment, or a "partial charge" representing various nonvanishing higher moments of an electrostatic multipole expansion, e.g., dipoles, quadrupoles, etc., whether in the classical or quantum mechanical regime.

To illustrate this point, FIG. 1a shows two molecules 110 and 120 of a potential molecular complex with high shape complementarity. However, the positive charges 125 of molecule 120 in or near the active site, denoted by region 130, are in unfavorable close electrostatic contact with the positive charges 115 located on molecule 110 in close proximity to region 130. The system in FIG. 1a, then exhibits poor electrostatic affinity and is unlikely to form a favorable molecular combination, yet computation of shape complementarity alone would not have detected this and instead overestimated the likelihood of combination of molecules 110 and 120.

Observe that molecule 110 may contain charges other than 115 and in fact molecule 110 may in fact be overall electrically neutral. The same potentially applies to molecule 120, but as illustrated in FIG. 1a, it is both the arrangement and magnitude of the charges on one molecule relative to another in a given relative orientation and position of the two molecules that most heavily impacts on the electrostatic affinity of the system.

FIG. 1b shows two molecules 140 and 150 with identical molecular shapes as molecules 110 and 120, respectively, of FIG. 1a. However, now the positive charges 155 of molecule 150, in or near the corresponding active site, denoted by region 160, are now in favorable close electrostatic contact with negative charges 145 on molecule 140 in close proximity to region 160. The system in FIG. 1b, unlike the system in FIG. 1a, then exhibits good electrostatic affinity in addition to high shape complementarity and is thus molecules 140 and 150 are more likely to form an energetically favorable molecular complex.

Thus in order to accurately analyze and characterize the nature and/or likelihood of a molecular combination, including, estimation of the binding affinity, and prediction of the binding mode (or even additional alternative modes) for the system, it is desirable to estimate the electrostatic affinity, i.e., the change in the electrostatic energy, of the system upon formation of a potential molecular complex. As used herein, "electrostatic energy" is a quantitative measure of the electrostatic affinity. Typically, when the electrostatic affinity is high, the change in electrostatic energy is very negative, whereas when the electrostatic affinity is poor, the change in electrostatic energy is near zero or may even be positive. As used herein, the "change in electrostatic energy" refers to the net difference in energy between a state where the two molecules are mutually interacting and a reference state where the two molecules are very far apart and thus their mutual electrostatic interaction is negligible. Computing the electrostatic affinity, as opposed to the final absolute electrostatic energy of the system, is significant since the two molecules in their initial reference state may already exhibit favorable self-electrostatic energies.

In general, however, it is computationally expensive to estimate the electrostatic affinity of a molecular combination in a suitable environment system for a large sequence of relative positions and orientations of the constituent molecules via conventional means, especially when one or more of the molecules are a macromolecule such as a protein or a long nucleotide sequence. Full treatment in the quantum mechanical regime is extremely impractical when the molecules in question are comprised of fifty or more atoms, due to the high complexity of suitable Hamiltonian functions. This is true even when considering only one relative position and orientation of the system, let alone the possibly millions of relative positions and orientations for each of possibly thousands or even millions of molecular combinations encountered during library screening. The reader is referred to Labanowski et al., [58] for a review of quantum mechanical calculations of electrostatics interactions.

Full treatment in the classical regime usually entails numerical solutions to second order partial differential equations [49][50] with appropriately chosen boundary conditions such as the Poisson-Boltzmann equation [45][47][48]. Such numerical solutions generally require many computations and exhibit high memory overhead. Moreover, new solutions must be generated for each distinct relative configuration of the two molecules because of the corresponding change in boundary conditions. Such classical methods are then also highly unsuitable for fast molecular docking and/or library screening.

Some attempts have been made to overcome this computational bottleneck by implementing a simple Coulombic energy model with a distance-dependent dielectric function $\in(r_{ij})$, as follows:

$$E = \sum_i \sum_j \frac{q_i q_j}{\varepsilon(r_{ij}) r_{ij}} \quad [\text{Eqn. 1}]$$

where $r_{ij}$ is the distance between charge $q_i$ and $q_j$. The reader is referred to Mehler et al., [46] for a comparison of dielectric models. Examples of methods using the formulation of Eqn. 1 include those of Luty et al., [26] and AutoDock [31].

However, Eqn. 1 is ad hoc at best when the two molecules are not in vacuum (i.e., $\in$=constant=$\in_0$) and thus often does not well represent the nature of electrostatic interactions for charges embedded in a polarizable medium (e.g., an appropriate solvent like water or even salt water). Moreover, even for the simple model represented by Eqn. 1, the computational effort stills scales quadratically with the number of charges in the two molecules, e.g., if the molecule has N point charges, their are N(N−1) distinct pairs which need to be calculated. This can be a real problem, especially when considering possibly millions of relative orientations and translations of the two molecules during a high-resolution search of the electrostatic affinity space.

Further computational savings can be obtained by introducing a cutoff radius, $r_{cutoff}$, beyond which the interaction is ignored, such as in Luty et al., [26]. However, due to the long distance scales inherent in the electrostatic interaction, this may lead to numerical inaccuracies, and thus accurate prediction of the electrostatic affinity may still require large cutoff radii, e.g., $r_{cutoff} \geq 10$–$20$ Å, thereby significantly reducing the savings provided by the cutoff radius.

Methods based on the use of a Generalized Born approximation [51][52], whether based on computations of volume or surface integrals, are viable alternatives for the calculation of charge-charge interactions for pairs of atoms or ions in the presence of continuum solvent. In general, however, though less computationally demanding, the Generalized Born approximation is not as accurate in estimating electrostatic energies as the Poisson-Boltzmann equation, and is still more costly than the distance-dependent dielectric Coulombic model of Eqn. 1.

Recently, a new approach as described in Ritchie et al., has been developed for the estimation of electrostatic affinity based on the decomposition of two volumetric functions describing respectively the charge distributions, and the electrostatic potential generated thereby, for each molecule onto an appropriate orthogonal basis set. As with the computations of shape complementarity based on similar techniques, required number of calculations scale linearly with the desired number of sampled configurations, thus allowing for a dense sampling of the search space associated with the electrostatic affinity of the two molecules.

However, the implementation described by Ritchie et al., has several drawbacks. First, it requires a complicated and computationally intensive representation of the electrostatic potential in terms of a Greens function expansion as applied to a general solution to Poisson's equation. Second, all solvent effects are ignored and the calculations are performed in vacuum, thereby limiting the applicable scope of the model. Third, their characterization of atomic charges as point charges, represented by Dirac delta functions, leads to sharp discontinuities in the charge distribution. Such discontinuities are very difficult to model accurately in a spherical harmonics expansion, thereby requiring a very large expansion order for the underlying basis expansions, and thus leading to large computational costs. Altogether, this leads to an imprecise estimate for the electrostatic affinity of most molecular complexes, unless the expansion order is so high as to make the calculations intractable in the context of a library screening. Furthermore, this approach is not amenable to implementation in customized or other application specific hardware for use in large-scale screening, due to the large number of required computations and exorbitant requirements for both memory storage and/or memory or i/o bandwidth.

In summary, it is desirable in the drug discovery process to identify quickly and efficiently the optimal configurations, i.e., binding modes, of two molecules or parts of molecules. Efficiency is especially relevant in the lead generation and lead optimization stages for a drug discovery pipeline, where it may be desirable to accurately predict the binding mode and binding affinity for possibly millions of potential target-ligand molecular combinations, before submitting promising candidates to further analysis. There is a clear need then to have more efficient systems and methods for computational modeling of the molecular combinations with reasonable accuracy.

In general, the present invention relates to an efficient computational method an analysis of molecular combinations based on maximization of electrostatic affinity (i.e., minimization of electrostatic energy relative to an isolated reference state) over a set of configurations of a molecular combination through computation of a basis expansion representing charge density and electrostatic potential functions associated with the molecules in a coordinate system. Here, the analysis of the molecular combination may involve the prediction of likelihood of formation of a potential molecular complex, the prediction of the binding mode (or even additional alternative modes) for the combination, the characterization of the nature of the interaction or binding of various components of the molecular combination, or even an approximation of binding affinity for the molecular combination based on an electrostatic affinity score or an equivalent measure. The teaching of this disclosure might also be used in conjunction with other methods for computation of shape complementarity, including the disclosure described in Kita II, in order to generate a composite affinity score reflecting both shape complementarity and electrostatic affinity for one or more configurations of a molecular combination. The invention also addresses and solves various hurdles and bottlenecks associated with efficient hardware implementation of the invention.

REFERENCES AND PRIOR ART

Prior art in the field of the current invention is heavily documented: the following tries to summarize it.

Drews [1] provides a good overview of the current state of drug discovery. In [2] Abagyan and Totrov show the state of high throughput docking and scoring and its applications. Lamb et al., [3] further teach a general approach to the design, docking, and virtual screening of multiple combinatorial libraries against a family of proteins, finally Waskowycz et al., [4] describe the use of multiple computers to accelerate virtual screening of a large ligand library against a specific target by assigning groups of ligands to specific computers.

[1] J. Drews, "Drug Discovery: A Historical perspective," Science 287, 1960–1964 (2000).

[2] Ruben Abagyan and Maxim Totrov, "High-throughput docking for lead generation". Current Opinion in Chemical Biology 2001, 5:375–382.

[3] Lamb, M. L.; Burdick, K. W.; Toba, S.; Young, M. M.; Skillman, A. G. et al, "Design, docking, and evaluation of multiple libraries against multiple targets". Proteins 2001, 42, 296–318.

[4] Waszkowycz, B., Perkins, T. D. J., Sykes, R. A., Li, J., "Large-scale virtual screening for discovering leads in the post-genomic era", IBM Systems Journal, Vol. 40, No. 2 (2001).

There are a number of examples of software tools currently used to perform docking simulations. These methods involve a wide range of computational techniques, including use of a) rigid-body pattern-matching algorithms, either based on surface correlations, use of geometric hashing, pose clustering, or graph pattern-matching; b) fragmental-based methods, including incremental construction or "place and join" operators; c) stochastic optimization methods including use of Monte Carlo, simulated annealing, or genetic (or memetic) algorithms; d) molecular dynamics simulations or e) hybrids strategies derived thereof.

The earliest docking software tool was a graph-based rigid-body pattern-matching algorithm called DOCK [6] developed at UCSF back in 1982 (v1.0) and now up to v5.0 (with extensions to include incremental construction). Other examples of graph-based pattern-matching algorithms include CLIX (which in turn uses GRID), FLOG and LIGIN.

[5] Shoichet, B. K., Bodian, D. L. and Kuntz, I. D., "Molecular docking using shape descriptors", *J. Comp. Chem.*, Vol. 13 No. 3, 380–397 (1992).

[6] Meng, E. C., Gschwend, D. A., Blaney, J. M., and I. D. Kuntz, "Orientational sampling and rigid-body minimization in molecular docking", *Proteins: Structure, Function, and Genetics*, Vol. 17, 266–278 (1993).

[7] Ewing, T. J. A. and Kuntz, I. D., "Critical Evaluation of Search Algorithms for Automated Molecular Docking and Database Screening", *J. Computational Chemistry*, Vol. 18 No. 9, 1175–1189 (1997).

[8] Lawrence, M. C. and Davis, P. C.; "CLIX: A Search Algorithm for Finding Novel Ligands Capable of Binding Proteins of Known Three-Dimensional Structure", *Proteins*, Vol. 12, 31–41 (1992).

[9] Kastenholz, M. A., Pastor, M., Cruciani, G., Haaksma, E. E. J., Fox, T., "GRID/CPCA: A new computational tool to design selective ligands", *J. Medicinal Chemistry*, Vol. 43, 3033–3044 (2000).

[10] Miller, M. D., Kearsley, S. K., Underwood, D. J. and Sheridan, R. P., "FLOG: a system to select "quasi-flexible" ligands complementary to a receptor of known three-dimensional structure", *J. Computer-Aided Molecular Design*, Vol. 8 No.2, 153–174 (1994).

[11] Sobolev, V., Wade, R. C., Vriend, G. and Edelman, M., "Molecular docking using surface complementarity", *Proteins*, Vol. 25, 120–129 (1996).

Other rigid-body pattern-matching docking software tools include the shape-based correlation methods of FTDOCK and HEX [13], the geometric hashing of Fischer et al., or the pose clustering of Rarey et al.

[12] Katchalski-Katzir, E., Shariv, I., Eisenstein, M., Friesem, A. A., Aflalo, C., and Vakser, I. A., "Molecular surface recognition: Determination of geometric fit between proteins and their ligands by correlation techniques", *Proceedings of the National Academy of Sciences of the United States of America*, Vol. 89 No. 6, 2195–2199 (1992).

[13] Ritchie, D. W. and Kemp. G. J. L., "Fast Computation, Rotation, and Comparison of Low Resolution Spherical Harmonic Molecular Surfaces", *J. Computational Chemistry*, Vol. 20 No. 4, 383–395 (1999).

[14] Fischer, D., Norel, R., Wolfson, H. and Nussinov, R., "Surface motifs by a computer vision technique: searches, detection, and implications for protein-ligand recognition", *Proteins*, Vol. 16, 278–292 (1993).

[15] Rarey, M., Wefing, S., and Lengauer, T., "Placement of medium-sized molecular fragments into active sites of proteins", *J. Computer-Aided Molecular Design*, Vol. 10, 41–54 (1996).

In general, rigid-body pattern-matching algorithms assume that both the target and ligand are rigid (i.e., not flexible) and hence may be appropriate for docking small, rigid molecules (or molecular fragments) to a simple protein with a well-defined, nearly rigid active site. Thus this class of docking tools may be suitable for de novo ligand design, combinatorial library design, or straightforward rigid-body screening of a molecule library containing multiple conformers per ligand.

Incremental construction based docking software tools include FlexX from Tripos (licensed from EMBL), Hammerhead, DOCK v4.0 (as an option), and the nongreedy, backtracking algorithm of Leach et al,. Programs using incremental construction in the context of de novo ligand design include LUDI [20] (from Accelrys) and Grow-Mol. Docking software tools based on "place and join" strategies include DesJarlais et al.

[16] Kramer, B., Rarey, M. and Lengauer, T., "Evaluation of the FlexX incremental construction algorithm for protein-ligand docking", *Proteins*, Vol. 37, 228–241 (1999).

[17] Rarey, M., Kramer, B., Lengauer, T., and Klebe, G., "A Fast Flexible Docking Method Using An Incremental Construction Algorithm", *J. Mol. Biol.*, Vol. 261, 470–489 (1996).

[18] Welch, W., Ruppert, J. and Jain, A. N., "Hammerhead: Fast, fully automated docking of flexible ligands to protein binding sites", *Chemical Biology*, Vol. 3, 449–462 (1996).

[19] Leach, A. R., Kuntz, I. D., "Conformational Analysis of Flexible Ligands in Macromolecular Receptor Sites", *J. Comp. Chem.*, Vol. 13, 730–748 (1992).

[20] Bohm, H. J., "The computer program LUDI: a new method for the de novo design of enzyme inhibitors", *J. Computer-Aided Molecular Design*, Vol. 6, 61–78 (1992).

[21] Bohacek, R. S. and McMartin, C., "Multiple Highly Diverse Structures Complementary to Enzyme Binding Sites: Results of Extensive Application of a de Novo Design Method Incorporating Combinatorial Growth", *J. American Chemical Society*, Vol. 116, 5560–5571 (1994).

[22] DesJarlais, R. L., Sheridan, R. P., Dixon, J. S., Kuntz, I. D., and Venkataraghavan, R., "Docking Flexible Ligands to Macromolecular Receptors by Molecular Shape", *J. Med. Chem.*, Vol. 29, 2149–2153 (1986).

Incremental construction algorithms may be used to model docking of flexible ligands to a rigid target molecule with a well-characterized active site. They may be used when screening a library of flexible ligands against one or more targets. They are often comparatively less compute intensive, yet consequently less accurate, than many of their stochastic optimization based competitors. However, even FlexX may take on order of <1–2 minutes to process one target-ligand combination and thus may still be computationally onerous depending on the size of the library (e.g., tens of millions or more compounds). Recently FlexX was extended to FlexE [23] to attempt to account for partial flexibility of the target molecule's active site via use of user-defined ensembles of certain active site rotamers.

[23] Claussen, H., Buning, C., Rarey, M., and Lengauer, T., "FlexE: Efficient Molecular Docking Considering Protein Structure Variations", *J. Molecular Biology*, Vol. 308, 377–395 (2001).

Computational docking software tools based on stochastic optimization include ICM [24] (from MolSoft), GLIDE [25]

(from Schrodinger), and LigandFit [26] (from Accelrys), all based on modified Monte Carlo techniques, and AutoDock v.2.5 [27] (from Scripps Institute) based on simulated annealing. Others based on genetic or memetic algorithms include GOLD, DARWIN, and AutoDock v.3.0 [31] (also from Scripps).

[24] Abagyan, R. A., Totrov, M. M., and Kuznetsov, D. N., "Biased probability Monte Carlo conformational searches and electrostatic calculations for peptides and proteins", *J. Comp. Chem.*, Vol. 15, 488–506 (1994).

[25] Halgren, T. A., Murphy, R. B., Friesner, R. A., Beard, H. S., Frye, L. L., Pollard, W. T., and Banks, J. L., "Glide: a new approach for rapid, accurate docking and scoring. 2. Enrichment factors in database screening", *J Med Chem.*, Vol. 47 No. 7, 1750–1759 (2004).

[26] Luty, B. A., Wasserman, Z. R., Stouten, P. F. W., Hodge, C. N., Zacharias, M., and McCammon, J. A., "Molecular Mechanics/Grid Method for the Evaluation of Ligand-Receptor Interactions", *J. Comp. Chem.*, Vol.16, 454–464 (1995).

[27] Goodsell, D. S. and Olson, A. J., "Automated Docking of Substrates to Proteins by Simulated Annealing", *Proteins: Structure, Function, and Genetics*, Vol. 8, 195–202 (1990).

[28] Jones, G., Willett, P. and Glen, R. C., "Molecular Recognition of Receptor Sites using a Genetic Algorithm with a Description of Desolvation", *J. Mol. Biol.*, Vol. 245, 43–53 (1995).

[29] Jones, G., Willett, P., Glen, R. C., Leach, A., and Taylor, R., "Development and Validation of a Genetic Algorithm for Flexible Docking", *J. Mol. Biol.*, Vol. 267, 727–748 (1997).

[30] Taylor, J. S. and Burnett, R. M., *Proteins*, Vol. 41, 173–191 (2000).

[31] Morris, G. M., Goodsell, D. S., Halliday, R. S., Huey, R., Hart, W. E., Belew, R. K. and Olson, A. J., "Automated Docking Using a Lamarckian Genetic Algorithm and an Empirical Binding Free Energy Function", *J. Comp. Chem.*, Vol. 19, 1639–1662 (1998).

Stochastic optimization-based methods may be used to model docking of flexible ligands to a target molecule. They generally use a molecular-mechanics based formulation of the affinity function and employ various strategies to search for one or more favorable system energy minima. They are often more compute intensive, yet also more robust, than their incremental construction competitors. As they are stochastic in nature, different runs or simulations may often result in different predictions. Traditionally most docking software tools using stochastic optimization assume the target to be nearly rigid (i.e., hydrogen bond donor and acceptor groups in the active site may rotate), since otherwise the combinatorial complexity increases rapidly making the problem difficult to robustly solve in reasonable time.

Molecular dynamics simulations have also been used in the context of computational modeling of target-ligand combinations. A molecular dynamics simulation refers to a simulation method devoted to the calculation of the time dependent behavior of a molecular system in order to investigate the structure, dynamics and thermodynamics of molecular systems. Examples include the implementations presented in Di Nola et al., [32], Mangoni et al., [33] and Luty et al., [26] (along with Monte Carlo). In principle, molecular dynamics simulations may be able to model protein flexibility to an arbitrary degree. On the other hand, they may also require evaluation of many fine-grained, time steps and are thus often very time-consuming (one order of hours or even days per target-ligand combination). They also often require user-interaction for selection of valid trajectories. Use of molecular dynamics simulations in lead discovery is therefore more suited to local minimization of predicted complexes featuring a small number of promising lead candidates.

[32] Di Nola, A., Berendsen, H. J. C., and Roccatano, D., "Molecular Dynamics Simulation of the Docking of Substrates to Proteins", *Proteins*, Vol. 19, 174–182 (1994).

[33] Mangoni, M., Raccatano, D., and Di Nola, A., "Docking of Flexible Ligands to Flexible Receptors in Solution by Molecular Dynamics Simulation", *Proteins: Structure, Function, and Genetics*, 35, 153–162, 1999;

Hybrid methods may involve use of rigid-body pattern matching techniques for fast screening of selected low-energy ligand conformations, followed by Monte Carlo torsional optimization of surviving poses, and finally even molecular dynamics refinement of a few choice ligand structures in combination with a (potentially) flexible protein active site. An example of this type of docking software strategy is Wang et al., [34].

[34] Wang, J., Kollman, P. A. and Kuntz, I. D., "Flexible ligand docking: A multistep strategy approach", *Proteins*, Vol. 36, 1–19 (1999).

A review discussing the importance of electrostatic interactions in biology and chemistry can be found in Honig et al., [35]. When modeling electrostatics interactions between molecules in an environment, especially in the context of molecular dynamics simulations or other molecular-mechanics-based methods, the assignment of charges (full or partial) to various molecular components must be addressed. An example of a commonly used, and classically derived, method for assignment of partial charges is PARSE described in Sitkoff et al., [36]. An example of commonly used quantum mechanical based software packages for the purpose of the assignment of partial charges is MOPAC [37] and GAMESS [38].

[35] Honig, B., and Nicholls, A., "Classical Electrostatics in Biology and Chemistry", *Science*, Vol. 268, 1144–1148 (1995).

[36] Sitkoff, D., Sharp, K. A., and Honig, B., in "Accurate Calculation of Hydration Free Energies Using Macroscopic Solvent Models", *J. Phys. Chem.*, Vol. 98, 1978–1988 (1994).

[37] J. J. P. Stewart, "MOPAC: A General Molecular Orbital Package" in *Quantum Chemistry Program Exchange*, Vol. 10, No. 86 (1990).

[38] Schmidt, M. W., Baldridge, K. K., Boatz, J. A., Elbert, S. T., Gordon, M. S., Jensen, J. J, Koseki, S., Matsunaga, N., Nguyen, K. A., Su, S., Windus, T. L., Dupuis, M., Montgomery, J. A., "General atomic and molecular electronic structure system", *J. Comput. Chem.*, Vol. 14, 1347–1363 (1993).

Partial charges may also be assigned to each covalently bound or other electrically neutral atoms of a molecule as per an molecular mechanics all-atom force field, especially for macromolecules such as proteins, DNA/RNA, etc. Such force fields may be used to assign various other atomic, bond, and/or other chemical or physical descriptors associated with components of molecules including, but not limited to, such items as vdW radii, solvation dependent parameters, and equilibrium bond constants. Examples of such force fields include AMBER [39][40], OPLS [41], MMFF [42], CHARMM [43], and the general-purpose Tripos force-field [44]of Clark et al.

[39] Pearlman, D. A., Case, D. A., Caldwell, J. C., Ross, W. S., Cheatham III, T. E., Ferguson, D. M., Seibel, G. L., Singh, U. C., Weiner, P., Kollman, P. A. *AMBER* 4.1, University of California, San Francisco (1995).

[40] Cornell, W. D., Cieplak, P., Bayly, C. I., Goulg, I. R., Merz, K. M., Ferguson, D. M., Spellmeyer, D. C., Fox, T., Caldwell, J. W., Kollman, P. A., "A second-generation force field for the simulation of proteins, nucleic acids, and organic molecules", *J. American Chemical Society*, Vol. 117, 5179–5197 (1995).

[41] Jorgensen, W. L., & Tirado-Rives, J., *J. American Chemical Society*, Vol. 110, 1657–1666 (1988).

[42] Halgren, T. A., "Merck Molecular Force Field. I. Basis, Form, Scope, Parameterization, and Performance of MMFF94", *J. Comp. Chem.*, Vol. 17, 490–519 (1996).

[43] Brooks, B. R., Bruccoleri, R. E., Olafson, B. D., States, D. J., Swaminathan, S. and Karplus, M., "CHARMM: A Program for Macromolecular Energy, Minimization, and Dynamics Calculations", *J. Comp. Chem.*, Vol. 4, 187–217 (1983).

[44] Clark, M., Cramer, R. D., Opdenbosch, N. V., "Validation of the General Purpose Tripos 5.2 Force Field", *J. Comp. Chem.*, Vol. 10, 982–1012 (1989).

A discussion on the calculation of total electrostatic energies involved in the formation of a potential molecular complex can be found in Gilson et al., [45]. Computational solutions of electrostatic potentials in the classical regime range from simpler formulations, like those involving distance-dependent dielectric functions [46] to more complex formulations, like those involving solution of the Poisson-Boltzmann equation [47][48], a second order, generally nonlinear, elliptic partial differential equation. A review of numerical solvers for second order partial differential equations with appropriate boundary conditions can be found in Press et al, [49] and Arfken et al., [50].

Other classical formalisms that attempt to model electrostatic desolvation include those based on the Generalized Born solvation model [51][52], methods that involve representation of reaction field effects via additional solvent accessible or fragmental volume terms [53][54], or explicit representation of solvent in the context of molecular dynamics simulations [55][56][57]. A lengthy review of full quantum mechanical treatment of electrostatics interactions can be found in Labanowksi et al., [58].

[45] Gilson, M. K., and Honig, B., "Calculation of the Total Electrostatic Energy of a Macromolecular System: Solvation Energies, Binding Energies, and Conformational Analysis", *Proteins*, Vol. 4, 7–18 (1988).

[46] Mehler, E. L. and Solmajer, T., "Electrostatic effects in proteins: comparison of dielectric and charge models" *Protein Engineering*, Vol. 4, 903–910 (1991).

[47] Hoist, M., Baker, N., and Wang, F., "Adaptive Multilevel Finite Element Solution of the Poisson-Boltzmann Equations 1. Algorithms and Examples", *J. Comp. Chem.*, Vol. 21, No. 15, 1319–1342 (2000).

[48] Nicholls, A., and Honig, B., "A Rapid Finite Difference Algorithm, Utilizing Successive Over-Relaxation to Solve Poisson-Boltzmann Equation", *J. Comp. Chem.*, Vol. 12, No. 4, 435–445 (1991).

[49] Press, W. H., Flannery, B. P., Teukolsky, S. A., and Vetterling, W. T., "Numerical Recipes in C: The Art of Scientific Computing", Cambridge University Press (1993).

[50] Arfken, G. B., and Weber H. J., "Mathematical Method for Physicist", Harcourt/Academic Press (2000).

[51] Still, W. C., Tempczyk, A., Hawley, R. C. and Hendrickson, T., "A General Treatment of Solvation for Molecular Mechanics", *J. Am. Chem. Soc.*, Vol. 112, 6127–6129 (1990).

[52] Ghosh, A., Rapp, C. S., and Friesner, R. A., "A Generalized Born Model Based on Surface Integral Formulation", *J. Physical Chemistry B.*, Vol. 102, 10983–10 (1988).Eisenberg, D., and McLachlan, A. D., "Solvation Energy in Protein Folding and Binding", *Nature*, Vol. 31, 3086 (1986).

[54] Privalov, P. L., and Makhatadze, G. I., "Contribution of hydration to protein folding thermodynamics", *J. Mol. Bio.*, Vol. 232, 660–679 (1993).

[55] Bash, P., Singh, U. C., Langridge, R., and Kollman, P., "Free Energy Calculation by Computer Simulation", *Science*, Vol. 236, 564 (1987).

[56] Jorgensen, W. L., Briggs, J. M., and Contreras, M. L., "Relative Partition Coefficients for Organic Solutes from Fluid Simulations", *J. Phys. Chem.*, Vol. 94, 1683–1686 (1990).

[57] Jackson, R. M., Gabb, H. A., and Sternberg, M. J. E., "Rapid Refinement of Protein Interfaces Incorporating Solvation: Application to the Docking Problem", *J. Mol. Biol.*, Vol. 276, 265–285 (1998).

[58] Labanowski and J. Andzelm, editors, "Density Functional Methods in Chemistry", Springer-Verlag, New York (1991).

BRIEF SUMMARY OF THE INVENTION

Aspects of the present invention relate to a method and apparatus for an analysis of molecular combinations featuring two or more molecular subsets, wherein either one or both molecular subsets are from a plurality of molecular subsets selected from a molecule library, based on computation of the electrostatic affinity of the system via utilization of a basis expansion representing charge density and electrostatic potential functions associated with the first and second molecular subsets in a coordinate system. Sets of transformed expansion coefficients are calculated for a sequence of different configurations, i.e., relative positions and orientations, of the first molecular subset and the second molecular subset using coordinate transformations. The sets of transformed expansion coefficients are constructed via the application of translation and rotation operators to a reference set of expansion coefficients. Then an electrostatic affinity, representing a correlation of the charge density and electrostatic potential functions of the first and second molecular subsets, is computed over the sequence of different sampled configurations for the molecular combination, where each sampled configuration differs in both the relative positions and orientations of the first and second molecular subsets. Aspects of the invention will also be discussed relating to its use in conjunction with other methods for computation of shape complementarity, including the method described in Kita II, in determining a composite or augmented score reflecting both electrostatic affinity and shape complementarity for configurations of a molecular combination. Various embodiments of the invention relating to efficient implementation of the invention in the context of a hardware apparatus are also discussed.

BRIEF DESCRIPTION OF THE DRAWINGS

A more complex appreciation of the invention and many of the advantages thereof will be readily obtained, as the same becomes better understood by references to the detailed description when considered in connection with the accompanying drawings, wherein:

FIGS. 3a, 3b, and 3c respectively show a "ball and stick" representation of an input pose for a methotrexate molecule, a digital representation in the form of a pdb formatted file, and another digital representation in the form of a mol2 formatted file, both files containing structural and chemical information for the molecule depicted in FIG. 3a;

FIGS. 6a and 6b shows illustrations of two molecular subsets in two different configurations with assessed in accordance with embodiments of the present invention;

FIG. 15 shows a flow diagram of a novel and efficient method for computing an electrostatic affinity score for a configuration of a molecular combination based on transformation and combination of basis expansion coefficients for associated charge density functions and electrostatic potential fields in accordance with embodiments of the present invention.

DETAILED DESCRIPTION OF THE INVENTION

Figure 1B:
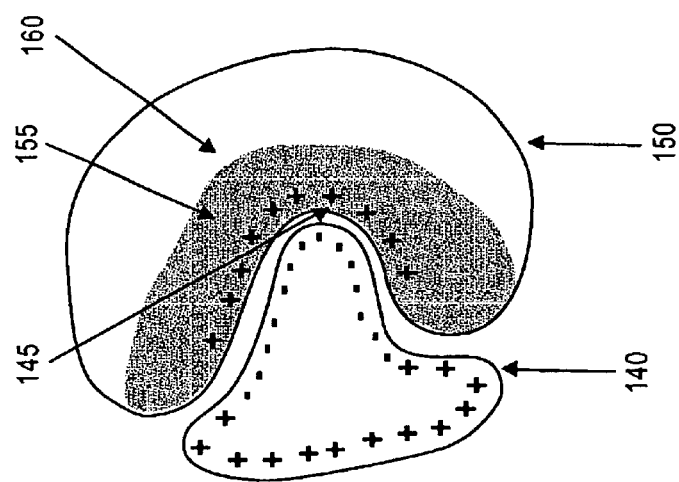
FIGS. 1a and 1b show illustrations of two distinct molecular combinations, with labels for positive and negative charges, both demonstrating high shape complementarity but each respectively showing poor and high electrostatic affinity.
Figure 1A:
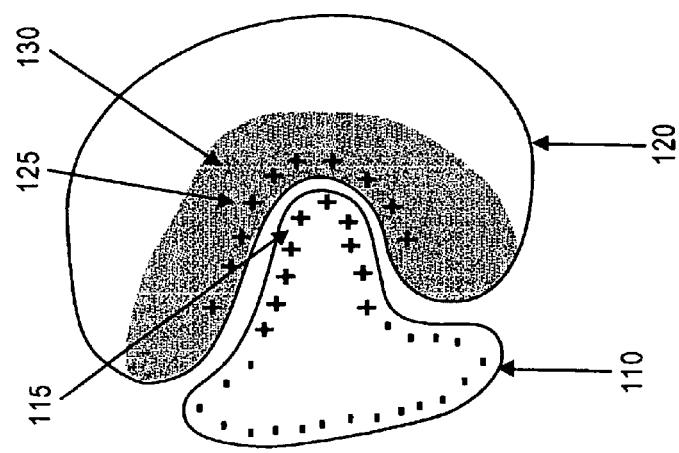

The present invention has many applications, as will be apparent after reading this disclosure. In describing an embodiment of a computational system according to the present invention, only a few of the possible variations are described. Other applications and variations will be apparent to one of ordinary skill in the art, so the invention should not be construed as narrowly as the examples, but rather in accordance with the appended claims.

Embodiments of the invention will now be described, by way of example, not limitation. It is to be understood that the invention is of broad utility and may be used in many different contexts.

A molecular subset is a whole or parts of the components of a molecule, where the components can be single atoms or bonds, groups of atoms and/or bonds, amino acid residues, nucleotides, etc. A molecular subset might include a molecule, a part of a molecule, a chemical compound composed of one or more molecules (or other bio-reactive agents), a protein, one or more subsets or domains of a protein, a nucleic acid, one or more peptides, or one or more oligonucleotides. In another embodiment of the present invention, a molecular subset may also include one or more ions, individual atoms, or whole or parts of other simple molecules such as salts, gas molecules, water molecules, radicals, or even organic compounds like alcohols, esters, ketones, simple sugars, etc. In yet another embodiment, the molecular subset may also include organic molecules, residues, nucleotides, carbohydrates, inorganic molecules, and other chemically active items including synthetic, medicinal, drug-like, or natural compounds.

In yet another embodiment, the molecular subset may already be bound or attached to the target through one or more covalent bonds. In another embodiment the molecular subset may in fact include one or more structural components of the target, such as secondary structure elements that make-up a tertiary structure of a protein or subunits of a protein quaternary structure. In another embodiment the molecular subset may include one or more portions of a target molecule, such as protein domains that include the whole or part of an active site, one or more spatially connected subsets of the protein structure that are selected based on proximity to one or more protein residues, or even disconnected protein subsets that feature catalytic or other surface residues that are of interest for various molecular interactions. In another embodiment, the molecular subset may include the whole of or part of an existing molecular complex, meaning a molecular combination between two or more other molecular subset, as, for example, an activated protein or an allosterically bound protein.

A molecular combination (or combination) is a collection of two or more molecular subsets that may potentially bind, form a molecular complex, or otherwise interact with one another. A combination specifies at the very least the identities of the two or more interacting molecular subsets.

A molecular pose is the geometric state of a molecular subset described by its position and orientation within the context of a prescribed coordinate system. A molecular configuration (or configuration) of a molecular combination represents the joint poses of all constituent molecular subsets of a molecular combination. Different configurations are denoted by different relative positions and orientations of the molecular subsets with respect to one another. Linear coordinate transformations that do not change the relative position or orientation of constituent molecular subsets will not result in different configurations.

For the purposes of the invention different configurations of a molecular combination are obtained by the application of rigid body transformations, including relative translation and rotation, to one or more molecular subsets. For the purposes of the invention, such rigid body transformations are expected to preserve the conformational structure, as well as the stereochemistry and/or tautomerism (if applicable), of each molecular subset. In regard to the invention it is contemplated that when analyzing distinct conformations or stereoisomers of a molecular subset, each distinct conformation or stereoisomer will appear in a distinct molecular combination, each with its own attendant analysis. In this way, molecular combinations featuring flexible molecular subsets may be better analyzed using the invention based on consideration of multiple combinations comprising distinct conformations and/or stereoisomers.

In many of the forthcoming examples and explanations, the molecular combination will represent the typical scenario of two molecular subsets where a ligand biomolecule (first molecular subset) interacts with a target biomolecule (usually a biopolymer; second molecular subset). Thus in regard to the present invention, an of a molecular combination may seek to determine whether, in what fashion (i.e., binding mode), and/or to what degree, a ligand will interact with a target molecule based on computations of electrostatic affinity of one or more configurations. A detailed discussion of the concept of electrostatic affinity will be forthcoming in the description. It should be understood that, unless otherwise indicated, such examples and explanations could more generally apply to molecular combinations wherein more than two molecular subsets bind or interact with one another, representing the whole of, or portion(s) of, one or more target molecules and/or one or more ligands.

As an example, in one embodiment of the present invention the molecular combination may represent a target interacting with a ligand (i.e., target-ligand pair) where one molecular subset is from the protein and the other the ligand. In a further embodiment, the molecular combination may represent a target-ligand pair where one molecular subset is the entire ligand biomolecule but the other molecular subset is a portion of a target biopolymer containing one or more relevant active sites.

In yet another embodiment, the molecular combination may feature more than two molecular subsets, one representing a target (whole or part) and the other two correspond to two distinct ligands interacting with the same target at the same time, such as in the case of competitive thermodynamic equilibrium between a possible inhibitor and a natural binder of a protein. In yet another embodiment the previous example may be turned around such that the molecular combination features two target molecules in competition with one ligand biomolecule.

As another example, in one embodiment the molecular combination may represent a protein-protein interaction in which there are two molecular subsets, each representing the whole or a relevant portion of one protein. In a further embodiment, the molecular combinations may also represent a protein-protein interaction, but now with potentially more than two molecular subsets, each representing an appropriate protein domain.

As a further example, the molecular combination may feature two molecular subsets representing a target-ligand pair but also additional molecular subsets representing other atoms or molecules (hetero-atoms or hetero-molecules) relevant to the interaction, such as, but not limited to, one or more catalytic or structural metal ions, one or more ordered, bound, or structural water molecules, one or more salt molecules, or even other molecules such as various lipids, carbohydrates, acids, bases, mRNA, ATP/ADP, etc. In yet another embodiment, the molecular combination may feature two molecular subsets representing a target-ligand pair but also one or more added molecular subsets representing a whole or portion of a cell membrane, such as a section of a lipid bi-layer, nuclear membrane, etc., or a whole or portion of an organelle such as a mitochondrion, a ribosome, endoplasmic reticulum, etc.

In another embodiment, the molecular combination may feature two or more molecular subsets, with one or more molecular subsets representing various portions of a molecular complex and another subset representing the ligand interacting with the complex at an unoccupied active site, such as for proteins complexed with an allosteric activator or for proteins containing multiple, distinct active sites.

In another embodiment, the molecular combination may feature two or more molecular subsets representing protein chains or subunits interacting noncovalently as per a quaternary protein structure. In another embodiment, the molecular combination may feature two or more molecular subsets representing protein secondary structure elements interacting as per a tertiary structure of a polypeptide chain, induced for example by protein folding or mutagenesis.

In many of the forthcoming examples and explanations, the molecular combination will represent the typical scenario of a target-ligand pair interacting with one another. As already mentioned in regard to the present invention, an analysis of a molecular combination may seek to determine whether, in what fashion, and/or to what degree or with what likelihood, a ligand will interact with a target molecule based on computations of electrostatic affinity. In another embodiment, the analysis may involve a plurality of molecular combinations, each corresponding to a different ligand, selected, for example, from a molecule library (virtual or otherwise), in combination with the same target molecule, in order to find one or more ligands that demonstrate high electrostatic affinity with the target, and are therefore likely to bind or otherwise react with the target. In such cases, it may be necessary to assign a score or ranking to each analyzed molecular combination based on the estimated maximal electrostatic affinity across a set of different configurations for each combination, in order to achieve relative comparison of relevant predicted bioactivity.

In such a scenario where each target-ligand pair is an individual combination, and if there are N ligands to be tested against one target, then there will be N distinct molecular combinations involved in the analysis. For sufficiently large molecule libraries, it may be necessary to analyze millions or more potential molecular combinations for a single target protein. In yet another embodiment, the analysis may be reversed and the plurality of molecular combinations represents a plurality of target molecules, each in combination with the same ligand biomolecule in the same environment. In other embodiments, the molecular combinations may represent multiple ligands and/or targets reacting simultaneously, i.e., more than just a target-ligand pair, and may also include various heteroatoms or molecules as previously discussed.

Figure 2:
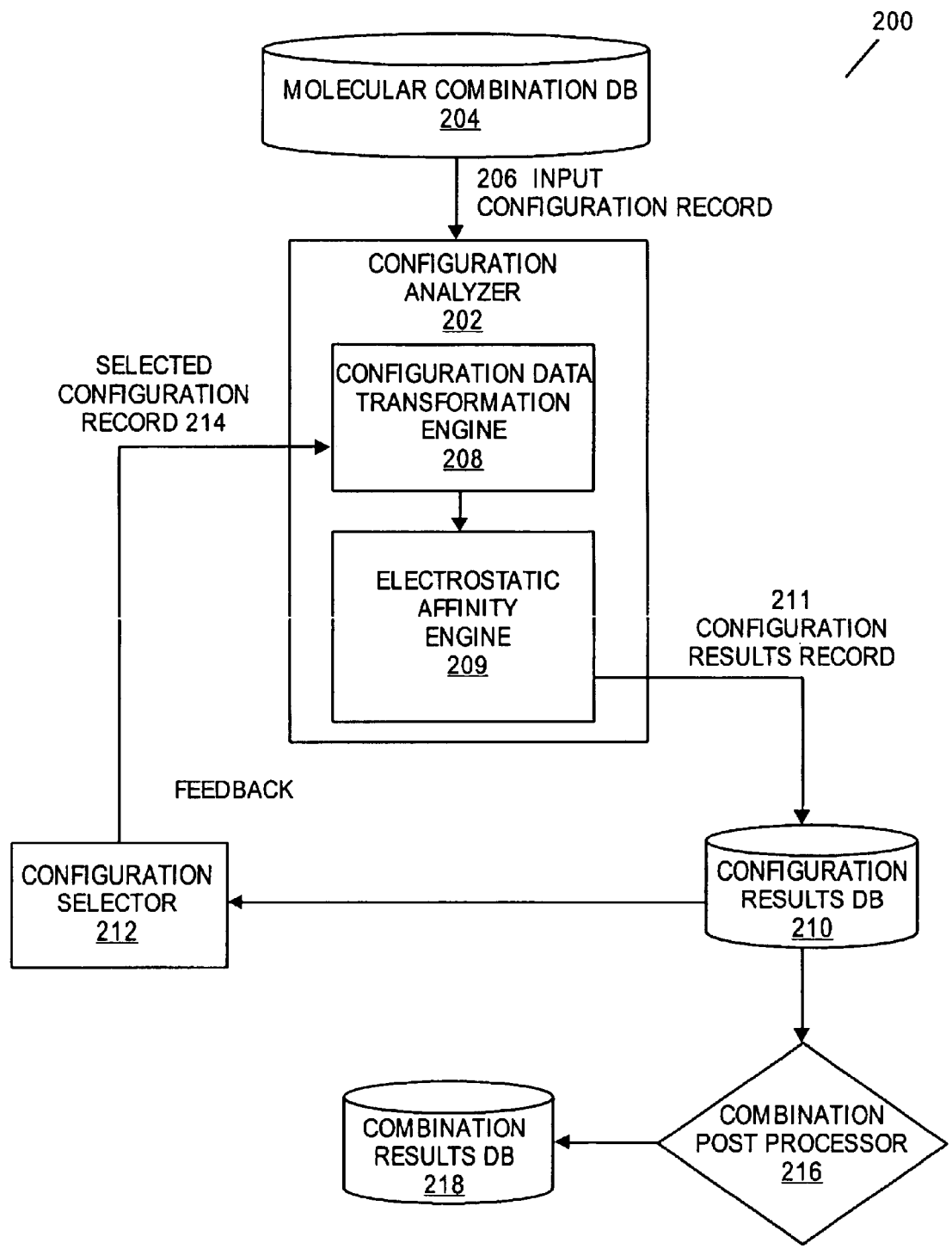
FIG. 2 is a block diagram view of an embodiment of a system that utilizes the present invention in accordance with analysis of a molecular combinations based on computations of electrostatic affinity over a set of sampled configurations.

FIG. 2 illustrates a modeling system 200 for the analysis of molecular combinations including computations of electrostatic affinity across a set of configurations for the molecular combination. As shown a configuration analyzer 202 receives one or more input (or reference) configuration records 206, including relevant structural, chemical, and physical data associated with input structures for both molecular subsets from an input molecular combination database 204. The configuration analyzer 202 comprises a configuration data transformation engine 208 and an electrostatic affinity engine 209. Results from the configuration analyzer 202 are output as configuration results records 211 to a configuration results database 210.

Modeling system 200 may be used to efficiently analyze molecular combinations via computations of electrostatic affinity. In some embodiments, this may include, but is not limited to, prediction of likelihood of formation of a potential molecular complex, or a proxy thereof, the estimation of the binding affinity between molecular subsets in the molecular combination, the prediction of the binding mode (or even additional alternative modes) for the molecular combination, or the rank prioritization of a collection of molecular subsets (e.g., ligands) based on maximal electrostatic affinity with a target molecular subset across sampled configurations of the combination, and would therefore also include usage associated with computational target-ligand docking.

Furthermore, the method provides for performing a dense search in the configurational space of two or more molecular subsets having rigid bodies, that is, assessing relative orientations and translations of the constituent molecular subsets. The method can also be used in conjunction with a process for generating likely yet distinct conformations of one or both molecular subsets, in order to better analyze those molecular combinations where one or both of the molecular subsets are flexible.

In a typical operation, many molecular combinations, each featuring many different configurations, may be analyzed. Since the total possible number of configurations may be enormous, the modeling system 200 may sample a subset of configurations during the analysis procedure according to an appropriate sampling scheme as will be discussed later. However, the sampled subset may still be very large (e.g., millions or even possibly billions of configurations per combination). An electrostatic affinity score is generated for each sampled configuration and the results for one or more configurations recorded in a storage medium.

The molecular combination may then be assessed by examination of the set of configuration results including the corresponding computed electrostatic affinity scores. Once the cycle of computation is complete for one molecular combination, modeling of the next molecular combination may ensue. Alternatively, in some embodiments of the modeling system 200, multiple molecular combinations may be modeled in parallel. Likewise, in some embodiments, during modeling of a molecular combination, more than one configuration may be processed in parallel as opposed to simply in sequence.

In one embodiment, modeling system 200 may be implemented on a dedicated microprocessor, ASIC, or FPGA. In another embodiment, modeling system 200 may be implemented on an electronic or system board featuring multiple microprocessors, ASICs, or FPGAs. In yet another embodiment, modeling system 200 may be implemented on or across multiple boards housed in one or more electronic devices. In yet another embodiment, modeling system 200 may be implemented across multiple devices containing one or more microprocessors, ASICs, or FPGAs on one or more electronic boards and the devices connected across a network.

In some embodiments, modeling system 200 may also include one or more storage media devices for the storage of various, required data elements used in or produced by the analysis. Alternatively, in some other embodiments, some or all of the storage media devices may be externally located but networked or otherwise connected to the modeling system 200. Examples of external storage media devices may include one or more database servers or file systems. In some embodiments involving implementations featuring one or more boards, the modeling system 200 may also include one or more software processing components in order to assist the computational process. Alternatively, in some other embodiments, some or all of the software processing components may be externally located but networked or otherwise connected to the modeling system 200.

In some embodiments, results records from database 210 may be further subjected to a configuration selector 212 during which one or more configurations may be selected based on various results criteria and then resubmitted to the configuration analyzer 202 (possibly under different operational conditions) for further scrutiny (i.e., a feedback cycle). In such embodiments, the molecular configurations are transmitted as inputs to the configuration analyzer 202 in the form of selected configuration records 214. In another embodiment, the configuration selector 212 may examine the results records from database 210 and construct other configurations to be subsequently modeled by configuration analyzer 202. For example, if the configuration analyzer modeled ten target-ligand configurations for a given target-ligand pair and two of the configurations had substantially higher estimated electrostatic affinity than the other eight, then the configuration selector 212 may generate further additional configurations that are highly similar to the top two high-scoring configurations and then schedule the new configurations for processing by configuration analyzer 202.

In some embodiments, once analysis of a molecular combination is completed (i.e., all desired configurations assessed) a combination postprocessor 216 may used to select one or more configuration results records from database 210 in order to generate one or more either qualitative or quantitative measures for the combination, such as a combination score, a combination summary, a combination grade, etc., and the resultant combination measures are then stored in a combination results database 218. In one embodiment, the combination measure may reflect the configuration record stored in database 210 with the best-observed electrostatic affinity. In another embodiment, multiple configurations with high electrostatic affinity are submitted to the combination postprocessor 216 and a set of combination measures written to the combination results database 218. In another embodiment, the selection of multiple configurations for use by the combination postprocessor 216 may involved one or more thresholds or other decision-based criteria.

In a further embodiment, the combination measures output to the combination results database 218 are based on various statistical analysis of a sampling of possibly a large number of configuration results records stored in database 210. In other embodiment the selection sampling itself may be based on statistical methods (e.g., principal component analysis, multidimensional clustering, multivariate regression, etc.) or on pattern-matching methods (e.g., neural networks, support vector machines, etc.)

In another embodiment, the combination postprocessor 216 may be applied dynamically (i.e., on-the-fly) to the configuration results database 210 in parallel with the analysis of the molecular combination as configuration results records become available. In yet another embodiment, the combination postprocessor 216 may be used to rank different configurations in order to store a sorted list of either all or a subset of the configurations stored in database 210 that are associated with the combination in question. In yet other embodiments, once the final combination results records, reflecting the complete analysis of the molecular combination by the configuration analyzer 202, have been stored in database 218, some or all of the configuration records in database 210 may be removed or deleted in order to conserve storage in the context of a library screen involving possibly many different molecular combinations. Alternatively, some form of garbage collection may be used in other embodiments to dynamically remove poor configuration results records from database 210.

In one embodiment, the molecular combination record database 204 may comprise one or more molecule records databases (e.g., flat file, relational, object oriented, etc.) or file systems and the configuration analyzer 202 receives an input molecule record corresponding to an input structure for each molecular subset of the combination. In another embodiment, when modeling target protein-ligand molecular combinations, the molecular combination record database 204 is replaced by an input target record database and an input ligand (or drug candidate) record database. In a further embodiment, the input target molecular records may be based on either experimentally derived (e.g., X-ray crystallography, NMR, etc.), energy minimized, or model-built 3-D protein structures. In another embodiment, the input ligand molecular records may reflect energy minimized or randomized 3-D structures or other 3-D structures converted from a 2-D chemical representation, or even a sampling of low energy conformers of the ligand in isolation. In yet another embodiment, the input ligand molecular records may correspond to naturally existing compounds or even to virtually generated compounds, which may or may not be synthesizable.

Figure 3A:
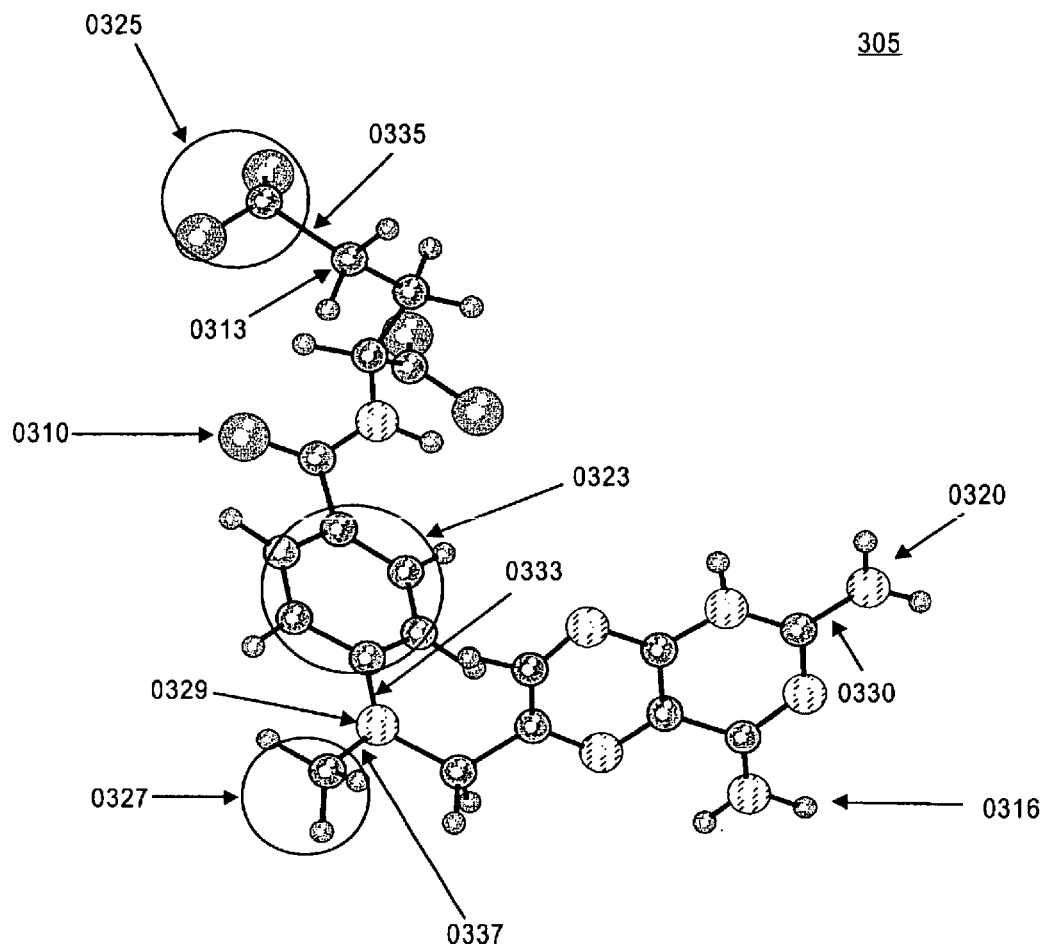
Figure 3C:
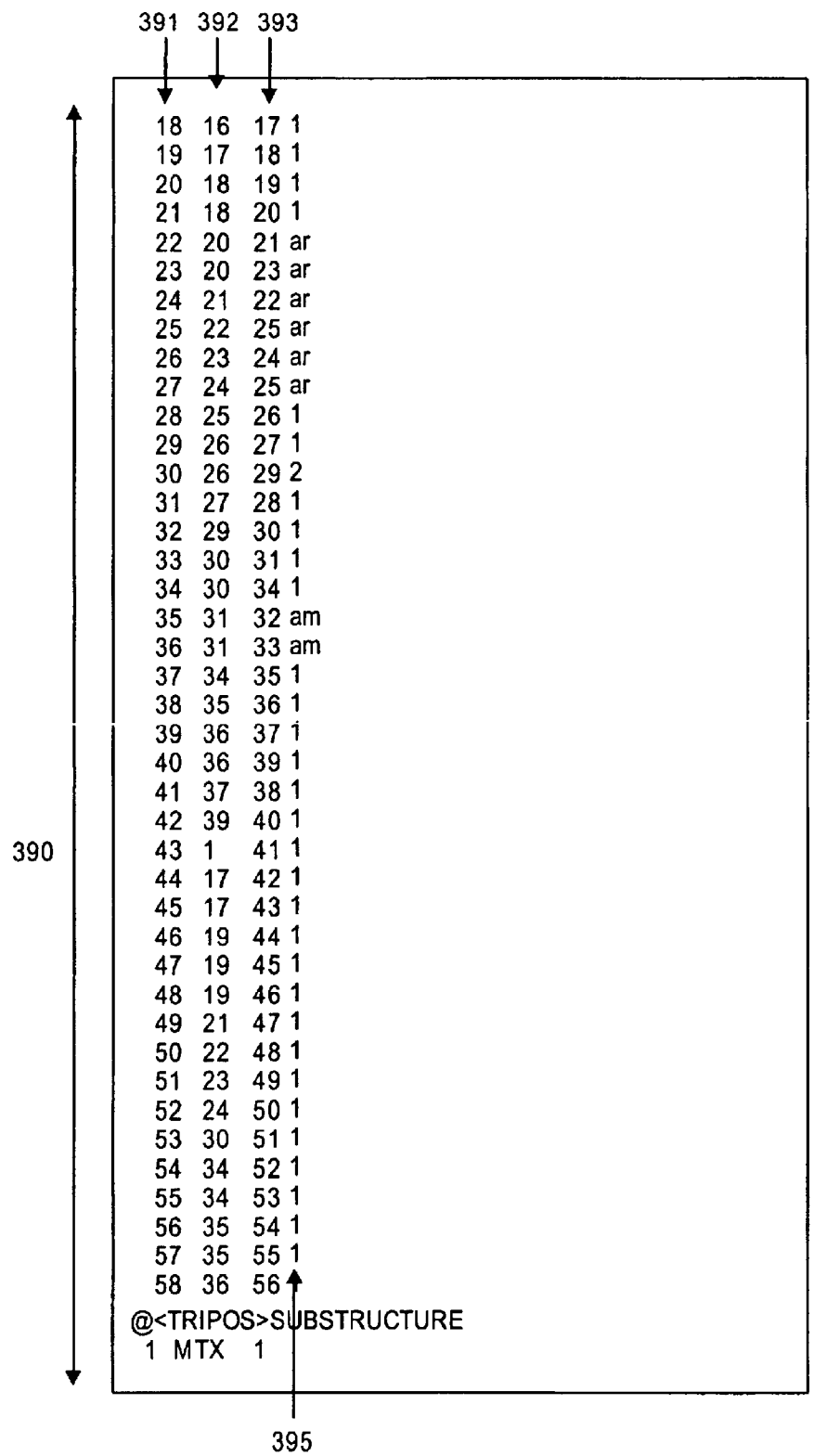

In order to better illustrate an example of an input structure and the associated input molecule record(s) that may form an input configuration record submitted to configuration analyzer 202 we refer the reader to FIGS. 3a, 3b, and 3c.

FIG. 3a shows a "ball-and-stick" rendering of a pose 305 of a methotrexate molecule 300 with chemical formula $C_{20}H_{22}N_8O_5$. The depicted molecular subset consists of a collection of atoms 320 and bonds 330. The small, black atoms, as indicated by item 313, represent carbon atoms. The tiny, white atoms, as indicated by item 316, represent hydrogen atoms, whereas the slightly larger dark atoms (item 310) are oxygen atoms and the larger white atoms (item 329) are nitrogen atoms. Continuing in FIG. 3a, item 323 denotes a circle containing a benzene ring ($C_6H_4$), and item 325 a circle containing a carboxyl group ($COO^-$), and item 327 another circle containing a methyl group ($CH_3$). Item 333 denotes a covalent bond connecting the benzene ring 323 to the ester group that includes the methyl group 327. Item 335 denotes a covalent bond connecting the carbon atom 313 to the carboxyl group 325. Lastly item 337 denotes a covalent bond connecting the methyl group 327 to a nitrogen atom 329.

FIG. 3b shows a pdb file representation 340 of a chemical structure for the methotrexate ligand pose described in FIG. 2a, including a general header 350, a section 360 composed of atom type and coordinate information, and a section 365 regarding bond connectivity information. The header section 350 may contain any annotation or other information desired regarding the identity, source, or characteristics of the molecular subset and its conformation and/or stereochemistry. Section 0360 shows a list of all 33 nonhydrogen atoms of methotrexate and for each atom it includes a chemical type (e.g., atomic element) and three spatial coordinates. For instance, the line for atom 6 shows that it is a nitrogen atom with name NA4 in a compound (or residue if a protein) named MTX in chain A with compound (or residue) ID of 1 and with (x, y, z) coordinates (20.821, 57.440, 21.075) in a specified Cartesian coordinate system. Note that the compound or residue name field may be more relevant for amino or nucleic acid residues in biopolymers.

Section 365 of the PDB file 340, sometimes called the connect record of a PDB file, describes a list of the bonds associated with each atom. For instance, the first line of this section shows that atom 1 is bonded to atoms (2), and (12), whereas the second line shows that atom 2 is bonded to atoms (1), (3), and (4). Notice also how in this example hydrogens are missing and as such the bond connections for each atom may not be complete. Of course, completed variants of the PDB file representation are possible if the positions of hydrogen atoms are already specified, but in many cases where the chemical structure originates from experimental observations the positions of hydrogens may be very uncertain or missing altogether.

FIG. 3c shows a MDL mol2 file containing various additional chemical descriptors above and beyond the information shown in the PDB file in FIG. 3b. Column 370 lists an index for each atom; column 373 lists an atom name (may be nonunique) for each atom; columns 375, 377, and 379 respectively list x, y, z coordinates for each atom in an internal coordinate system; column 380 lists a SYBYL atom type according to the Tripos force field [44] for each atom that codifies information for hybridization states, chemical type, bond connectivity, hydrogen bond capacity, aromaticity, and in some cases chemical group; and columns 382 and 385 list a residue ID and a residue name for each atom (relevant for proteins, nucleic acids, etc.). Section 390 lists all bonds in the molecular subset. Column 391 lists a bond index for each bond; columns 392 and 393 the atom indices of the two atoms connected by the bond; and column 395 the bond type, which may be single, double, triple, delocalized, amide, aromatic, or other specialized covalent bonds. In other embodiments such information may also represent noncovalent bonds such as salt bridges or hydrogen bonds. In this example, notice how the hydrogen atoms have now been included.

In one embodiment the configuration data transformation engine 208 may directly transform one or more input molecular configurations into one or more other new configurations by application of various rigid body transformations. In other embodiments, the configuration data transformation engine 208 may instead apply rigid body transformations to sets of basis expansion coefficients representing charge density and electrostatic potential functions associated with reference poses for each molecular subset as will be discussed in more detail later in the technical description. In some embodiments, the set of configurations visited during the course of an analysis of a molecular combination may be determined according to a schedule or sampling scheme specified in accordance with a search of the permitted configuration space for the molecular combination.

In some embodiments, whether generated by direct transformation of structural coordinates or by transformation of sets of basis expansion coefficients, the configuration data transformation engine 208 may produce new configurations (or new sets of basis expansion coefficients corresponding to new configurations) sequentially and feed them to the electrostatic affinity engine 209 in a sequential manner, or may instead produce them in parallel and submit them in parallel to the electrostatic affinity engine 209.

The electrostatic affinity engine 209 is responsible for generating an electrostatic affinity score or equivalent measure for each sampled configuration of the molecular combinations and makes use of the present invention to efficiently compute the electrostatic affinity for each configuration based on use of basis expansions and rigid body transformations of molecular charge density and electrostatic potential functions. The electrostatic affinity engine 209 may also include one or more storage components for data specific to the computations of electrostatic affinity.

In some embodiments, the configuration results records 211 may include a quantitative measure related to the electrostatic affinity evaluated for each configuration. In one embodiment, this may be a score. In another embodiment, this may be a probability. In other embodiments, the configuration results records 211 may include a qualitative measure related to the electrostatic affinity evaluated for the configuration. In one embodiment, this may be a grade. In another embodiment this may be a categorization (i.e., poor, weak, strong, etc.). In yet another embodiment this may be a simple pass-fail measure.

In many embodiments, the configuration results records 211 may also include information used to specify the identity and/or nature of configuration corresponding to a given electrostatic affinity score. In addition to the identity of the interacting molecular subsets, there may be a need to annotate or otherwise represent the geometrical state of the configuration.
Typically this may be achieved by storing the parameters of the rigid body transformation used to generate the configuration from an input or reference configuration.

In some embodiments, the configuration selector 212 may utilize various selection criteria in order to resubmit certain configurations back to modeling system 202 for more computations. In one embodiment, the selection criteria may be predicated on passing of a threshold or other decision mechanism based on one or more qualitative affinity measures. In another embodiment, the selection criteria may be based on a threshold or other decision mechanism based on one or more quantitative electrostatic affinity scores.

In yet another embodiment, the selection criteria used by the configuration selector 212 may be based on various statistical analysis of a number of different configuration results records stored in database 210, including, but not limited to, principal component analysis, multidimensional clustering, Bayesian filters, multivariate regression analysis, etc. In yet another embodiment, the selection criteria may be based on various pattern matching analysis of a number of different configuration results records stored in database 210, including, but not limited to, use of neural networks, support vector machines, hidden Markov models, etc.

In some embodiments, the configuration data transformation engine 208 may receive certain resubmitted configurations from the configuration selector 212 and utilize them as inputs to start a new cycle of electrostatic affinity computations. For example, if a particular configuration was selected from database 210 based on high electrostatic affinity by the configurations selector 212, the configuration data transformation engine 208 may generate multiple configurations (or multiple sets of basis expansion coefficients corresponding to new configurations) that are similar (i.e., slightly different positions and orientations for each molecular subset) in order to better investigate that portion of the possible configuration space of the molecular combination. In other embodiments, the new cycle of electrostatic affinity computations instigated by the resubmission of the selected configurations records 214 may involve the operation of the configuration analyzer 202 under a different set of conditions or using a different set of control parameters. In further embodiments, the selected configurations records 214 may kick off a new cycle of electrostatic affinity using a different variant of the configuration analyzer 202, including the use of a modified formulation for subsequent electrostatic affinity scores (if appropriate).

At this juncture it is worthwhile to discuss in more detail what is involved in computation of electrostatic affinity including physical concepts such as charge density functions, electrostatic potentials, electrostatic desolvation, as well as the mathematical formalism regarding calculation of electrostatic energy of a physical system.

The term "charge density" refers herein to a volume function, $\rho(\vec{r})$, representing a charge distribution. The "electrostatic potential function" generated by a charge distribution represented by $\rho(\vec{r})$, in vacuum, is given by:

$$\Phi(\vec{r}) = \frac{1}{4\pi\varepsilon_0} \int \frac{\rho(\vec{r}_1)}{|\vec{r} - \vec{r}_1|} d\vec{r}_1 \qquad \text{[Eqn. 2]}$$

where, $\varepsilon_0$ is the dielectric constant of vacuum, $\vec{r}_1$ is the 3-D coordinate of a differential volume element, $d\vec{r}$, within the domain of the charge distribution, and $\vec{r}$ is the 3-D coordinate of the point of evaluation of the electrostatic potential function. Note that Eqn. 2 only applies when the surrounding medium is vacuum or the charges are point charges and the dielectric medium is isotropic. The electrostatic potential function is not to be confused with the electric field, a vector function given by $\vec{E}(\vec{r}) = -\nabla\Phi(\vec{r})$. The electrostatic potential function associated with Eqn. 2 is herein referred to as a Coulomb potential function, given its basis on Coulomb's law of electrostatics.

The electrostatic energy, E, for a charge distribution represented by $\rho(\vec{r})$ and with an associated electrostatic potential function, $\Phi(\vec{r})$, is generally given as follows:

$$E = \frac{1}{2} \int \rho(\vec{r})\Phi(\vec{r}) d\vec{r} \qquad \text{[Eqn. 3]}$$

where the integral is over all points r in the charge distribution. Eqn. 3 reduces to the following form when Eqn. 2 is applicable and E is taken to be the self-electrostatic energy of the charge distribution:

$$U = \frac{1}{8\pi\varepsilon_0} \int \frac{\rho(\vec{r}_1)}{|\vec{r}_2 - \vec{r}_1|} \rho(\vec{r}_2) d\vec{r}_1 d\vec{r}_2 \qquad \text{[Eqn. 4]}$$

where $\vec{r}_1$ and $\vec{r}_2$ are 3-D coordinates of corresponding differential volume elements, $d\vec{r}_1$ and $d\vec{r}_2$, within the domain of the charge distribution.

When a charge distribution corresponding to a solute molecule is embedded in an anisotropic dielectric medium, Eqn. 3 still holds but eqns. 2 & 4 are no longer applicable, as the electrostatic potential function, $\Phi(\vec{r})$, should now include the effects of electrostatic desolvation. As used herein, "solvent" refers to the plurality of atoms, ions, and/or simple molecules (e.g., water, salt, sugars) that comprise an ambient medium, polarizable or otherwise and "electrostatic desolvation" refers to the interaction of a polar or charged solute entity in the presence of a polarizable medium having solvent entities. Herein "solvent entity" refers to individual solvent atoms, solvent molecules, and/or ions of the ambient medium and "solute entity" refers to polar or charged atoms or chemical groups that comprise the charge distributions associated with one or more molecules. Generally, the presence of solvent surrounding the charge distribution requires solution to either the Poisson equation or the Poisson-Boltzmann equation [36][45], depending on the presence of one or more solvent ionic components, as will be discussed below.

For the purposes of the invention, we are interested in the change in the total electrostatic energy of a system comprising charge distributions associated with two molecules embedded in a solvent environment upon formation of a potential molecular complex. A discussion on the calculation of total electrostatic energies involved in the formation of a potential molecular complex can be found in Gilson et al., [45].

Figure 4:
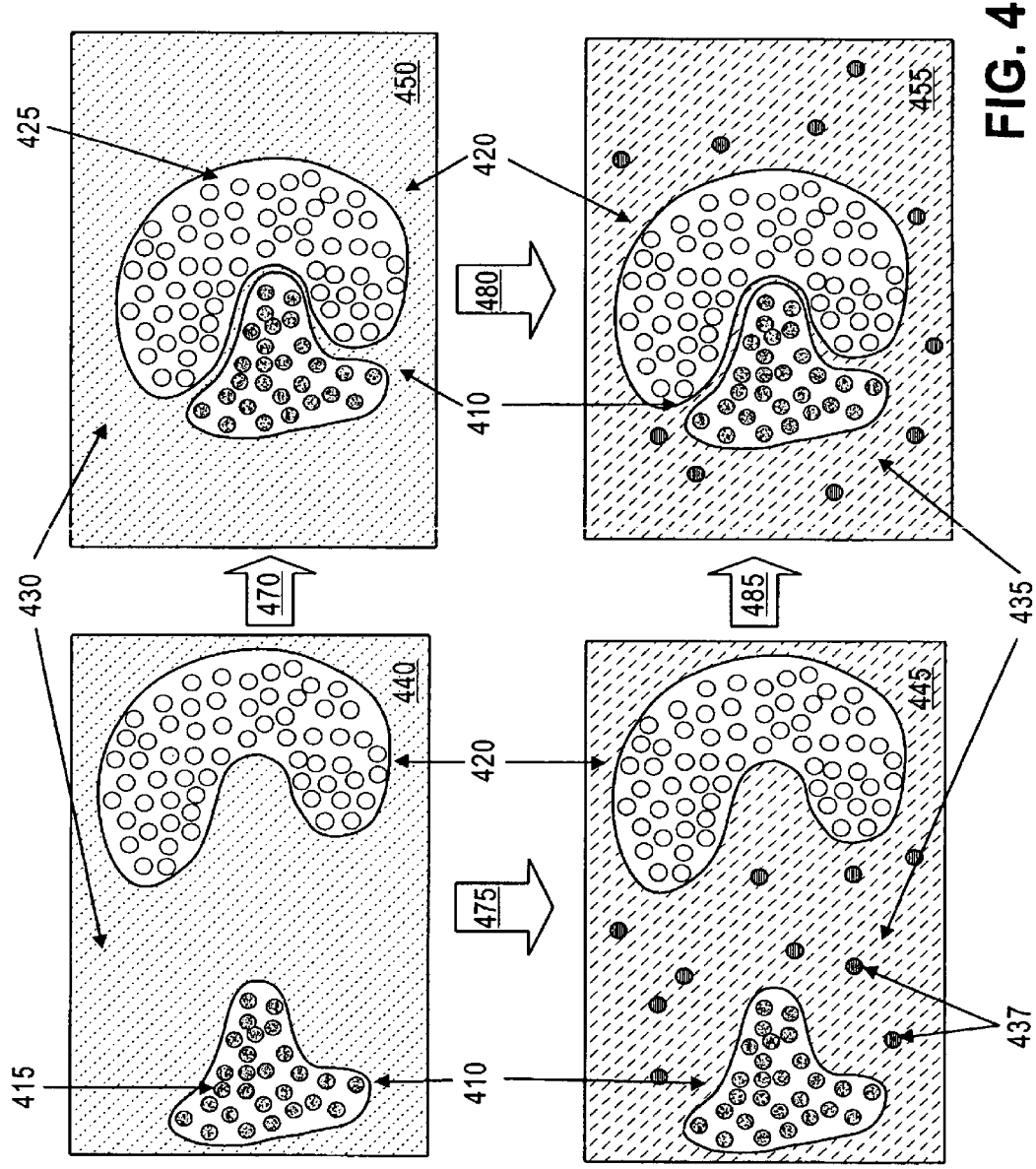
FIG. 4 shows an illustration of the thermodynamic cycle associated with the formation of a potential molecular complex in a solvent environment as relates to an understanding of the concept of electrostatic affinity for a molecular combination.

FIG. 4 depicts the four thermodynamic states of the relevant thermodynamic cycle for such a system. In FIG. 4, the two molecules are represented by 410 and 420 respectively, region 430 refers to a region of vacuum, region 435 refers to region in a solvent environment, and the particles labeled 437 refer to solvent entities comprising region 435. The circles labeled 415 represent the charge distribution of molecule 410, i.e., $\rho_1$, and those circles labeled 425 represent the charge distribution of molecule 420, i.e., $\rho_2$.

In FIG. 4, state 440 refers to a thermodynamic state where the molecules 410 and 420 are isolated and in vacuum, i.e., situated in region 430, whereas state 445 refers to the same two molecules, 410 and 420, in region 435, i.e., embedded as solutes in a solvent medium. State 450 refers to a thermodynamic state wherein molecules 410 and 420 are situated in the vacuum region 430, but are no longer in isolation with respect to one another and may in fact be forming a molecular complex. State 455 is the state analogous to state 450 but now residing in the solvent region 435.

As used herein, "isolation" refers to a state where the two molecules do not interact with one another, i.e., are infinitely far apart. In practice "isolation" would more likely correspond to the case that the two molecules are very far apart relative to their respective characteristic dimensions, and thus their mutual electrostatic interaction energy is negligible.

In FIG. 4, Eqn. 3 for the electrostatic energy is applicable to all four depicted thermodynamic states with $\rho(\vec{r})=\rho_1(\vec{r})+\rho_2(\vec{r})$, but depending on the particular state the form for the electrostatic potential, $\Phi(\vec{r})$, changes. For example, for vacuum state 440, the electrostatic energy, $E_{840}$, is given by:

$$E_{440} = U_1 + U_2 \qquad [\text{Eqn. 5}]$$

$$= \frac{1}{2}\int \rho_1(\vec{r}_1)\Phi_1(\vec{r}_1)d\vec{r}_1 + \frac{1}{2}\int \rho_2(\vec{r}_2)\Phi_2(\vec{r}_2)d\vec{r}_2$$

where $\vec{r}_1$ is any point in a volume containing the charge distribution of molecule 410 ($\rho_1$) and similarly $\vec{r}_2$ is any point in a volume containing the charge distribution of molecule 420 ($\rho_2$). In Eqn. 5, $\Phi_1$ refers to the Coulomb electrostatic potential of molecule 410 in vacuum as defined in Eqn. 4, and similarly $\Phi_2$ refers to the Coulomb electrostatic potential of molecule 420 in vacuum, also given by Eqn. 2. Note that Eqn. 5 was derived from Eqn. 3 utilizing the joint charge distribution $\rho(\vec{r})=\rho_1(\vec{r})+\rho_2(\vec{r})$, linear superposition of the electrostatic potentials, i.e., $\Phi(\vec{r})=\Phi_1(\vec{r})+\Phi_2(\vec{r})$, and the condition of isolation for both molecules In Eqn. 5, $U_1$ refers to the self-electrostatic energy of molecule 410 in isolation and is equivalent to the first integral in Eqn. 5 and is also equivalent to Eqn. 4 when substituting $\rho$ with $\rho_1$. Similarly $U_2$ refers to the self-electrostatic energy of molecule 420 in isolation and is equivalent to the second integral in Eqn. 5 and is also equivalent to Eqn. 4 when substituting $\rho$ with $\rho_2$.

For vacuum state 450, the electrostatic energy, $E_{850}$, is given by:

$$E_{450} = U_1 + U_2 + U_{12} \qquad [\text{Eqn. 6}]$$

$$= \frac{1}{2}\int \rho_1(\vec{r}_1)\Phi_1(\vec{r}_1)d\vec{r}_1 + \frac{1}{2}\int \rho_2(\vec{r}_2)\Phi_2(\vec{r}_2)d\vec{r}_2 +$$

$$\frac{1}{2}\int \rho_1(\vec{r}_1)\Phi_2(\vec{r}_1)d\vec{r}_1 + \frac{1}{2}\int \rho_2(\vec{r}_2)\Phi_1(\vec{r}_2)d\vec{r}_2$$

where $\vec{r}_1$, $\vec{r}_2$, $\rho_1$, $\rho_2$, $\Phi_1$, $\Phi_2$, $U_1$, and $U_2$ are all defined as before in regard to Eqn. 5. Once again, Eqn. 6 was derived from Eqn. 5 using the joint charge distribution $\rho(\vec{r})=\rho_1(\vec{r})+\rho_2(\vec{r})$, linear superposition of the electrostatic potentials, i.e., $\Phi(\vec{r})=\Phi_1(\vec{r})+\Phi_2(\vec{r})$, but now the two molecules are not in isolation and hence the mutual electrostatic interaction energy, $U_{12}$, represented by the third and fourth integrals cannot be ignored. In fact the change in electrostatic energy going from the isolated vacuum state 440 to potential molecular complex in vacuum of state 450, as depicted by arrow 470, is:

$$E_{450} - E_{440} = U_{12} \qquad [\text{Eqn. 7}]$$

$$= \frac{1}{2}\int \rho_1(\vec{r}_1)\Phi_2(\vec{r}_1)d\vec{r}_1 +$$

$$\frac{1}{2}\int \rho_2(\vec{r}_2)\Phi_1(\vec{r}_2)d\vec{r}_2.$$

For state 445, representing molecules 410 and 420 in isolation but embedded in solvent, the total electrostatic energy, $E_{845}$, is given by:

$$E_{445} = U_1'' + U_2'' \qquad [\text{Eqn. 8}]$$

$$= \frac{1}{2}\int \rho_1(\vec{r}_1)\Phi_1'(\vec{r}_1)d\vec{r}_1 + \frac{1}{2}\int \rho_2(\vec{r}_2)\Phi_2'(\vec{r}_2)d\vec{r}_2$$

where $\vec{r}_1$, $\vec{r}_2$, $\rho_1$, and $\rho_2$ are as before in eqns. 5–7, but $\Phi_1'$ and $\Phi_2'$ refer respectively to the electrostatic potential of molecule 410 in solvent in isolation and molecule 420 in solvent in isolation. $\Phi_i'$ differs from the corresponding in vacuo, Coulombic electrostatic potential $\Phi_i$ as a result of electrostatic desolvation, i.e., the interaction of a polar or charged solute entity in the presence of a polarizable medium having solvent entities. As such then Eqn. 4 no longer applies to $\Phi_i'$ and hence Eqn. 4 no longer applies to $U_i'$.

Electrostatic desolvation can be broken into three kinds of interactions: (1) a reaction field term representing the favorable interaction of a solute entity with the induced polarization charge near the solvent-solute interface, (2) a solvent screening effect reflecting the reduction of a Coulombic electrostatic interaction between a pair of solute entities due to intervening solvent containing solvent entities with net charge and/or nonvanishing dipole moments, and (3) interaction of solute entities with an ionic atmosphere comprised of one or more electrolytes in the solvent (if present).

All three effects are dependent on the degree of solvent accessibility for each solute entity, i.e., the size and geometry of the solute-solvent interface. The distance-dependent dielectric/Coulomb model of Eqn. 1 is an attempt to approximate the solvent screening effects. In some cases an additional term based on solvent accessible surface area or fragmental volumes is added in order to approximate the reaction field effect [53][54]. Typically, the presence of an ionic atmosphere is ignored altogether, though previous work, as described in Sitkoff et al., [36], has shown that such simplistic approximations are often consistently inaccurate representations of the role of electrostatic desolvation in the formation of a potential molecular complex.

Returning to FIG. 4, for state 455, representing molecules 410 and 420 in no longer in isolation but still embedded in solvent, the electrostatic energy, $E_{455}$, is given by:

$$E_{455} = U_1' + U_2' \quad [\text{Eqn. 9}]$$

$$= \frac{1}{2} \int \rho_1(\vec{r}_1) \Phi''(\vec{r}_1) d\vec{r}_1 + \frac{1}{2} \int \rho_2(\vec{r}_2) \Phi''(\vec{r}_2) d\vec{r}_2$$

where $\vec{r}_1$, $\vec{r}_2$, $\rho_1$, and $\rho_2$ are as before in eqns. 4–8. In general, the total electrostatic potential, $\Phi''$, of the potential molecular complex in the presence of a polarizable medium, such as that represented by solvent region 435, cannot be represented in terms of two separate electrostatic potential functions. However, as will be discussed later, in some cases it is possible to approximate the total electrostatic potential, $\Phi''$, in Eqn. 9 as two linearly super-imposable potentials, $\Phi_1''$ and $\Phi_2''$, each generated separately by the charge distribution of one of the molecules, while the charge distribution on the other molecule is ignored, though both potentials will be different from their counterparts, $\Phi_1'$ and $\Phi_2'$, in state 450.

Note that in Eqn. 9 the first integral represents the total electrostatic energy of the charge distribution of molecule 410 in state 455, including both its self-electrostatic energy and its mutual interaction with the charge distribution of molecule 420 as mediated by the ambient solvent of region 435. Similarly, the second integral of Eqn. 8 represents the total electrostatic energy of the charge distribution of molecule 420 in state 455.

As depicted by arrow 475, going from state 440 to 445, the difference in total electrostatic energy is solely the result of electrostatic desolvation of each molecule in isolation. Going from state 450 to state 455, as depicted by arrow 480, once gain the difference in total electrostatic energy is solely the result of electrostatic desolvation, but now of the two molecules together in close proximity during formation of a potential molecular complex. Lastly, going from state 445 to state 455, as depicted by arrow 485, the difference in total electrostatic energy is the result of bringing the two molecules closer to one another; thereby bringing the charge distributions on each molecule closer together and also changing the electrostatic desolvation of the two molecules as the solvent accessibilities of solute entities on each molecule are altered.

For the purposes of an analysis of molecular combinations based on computations of electrostatic affinity, the most relevant change of states is arrow 485, and thus the most relevant change in total electrostatic energy that must be calculated is given by $\Delta E = E_{455} - E_{445}$. In practice, due to the complexity of Eqn. 9 and the inclusion of electrostatic desolvation effects in the total electrostatic potential, $\Phi''$, $\Delta E$ may be difficult to accurately compute, especially for a large plurality of distinct molecular configurations. However, as shown in FIG. 4, as indicated by arrow 490, $\Delta E$ may be computed in four steps as follows: (1) compute $-\Delta E_1 = E_{440} - E_{445}$, (2) compute $+\Delta E_2 = E_{450} - E_{440}$, (3) compute $+\Delta E_3 = E_{455} - E_{450}$, and (4) form the sum $\Delta E = -\Delta E_1 + \Delta E_2 + \Delta E_3$. Thus in the syntax of FIG. 4, embodiments of the present invention directly provide for an accurate and efficient estimation of the electrostatic affinity, i.e., $\Delta E = E_{455} - E_{445}$, for a large plurality of different molecular configurations of for one or more molecular combinations.

Figure 5:
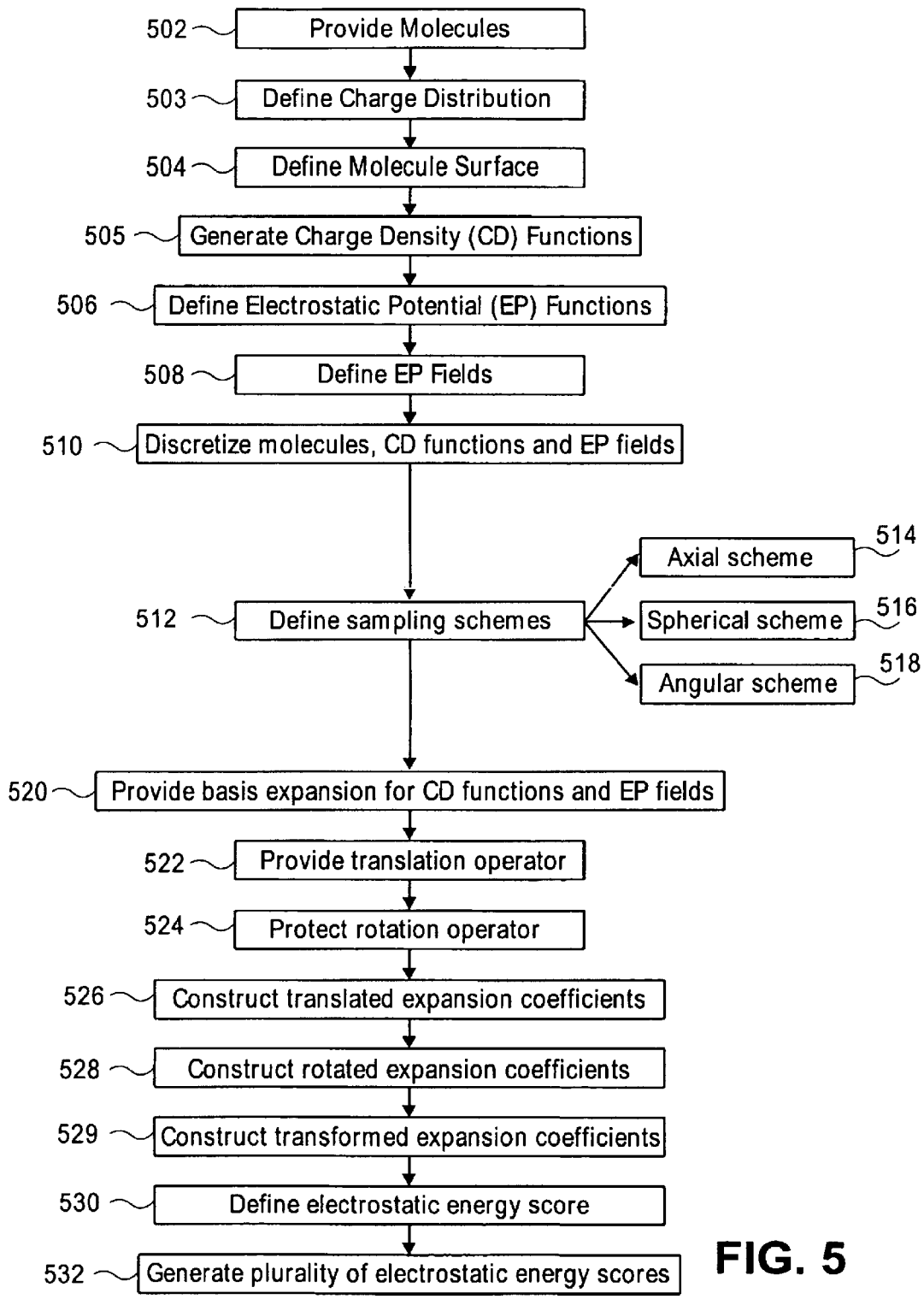
FIG. 5 shows a flow diagram of an exemplary method 500 for estimating the electrostatic affinity associated with analysis of a molecular combination, performed in accordance with embodiments of the present invention.

FIG. 5 shows a flow diagram of an exemplary method 500 of analyzing a molecular combination based on computations of electrostatic affinity across a set of configurations, performed in accordance with embodiments of the present invention. The method 500 of FIG. 5 is described with reference to FIGS. 6–15. As explained below, the method 500 generally involves computing a basis expansion representing charge density and electrostatic potential functions associated with constituent molecular subsets, computing transformed expansion coefficients for different configurations (i.e., relative positions and orientations) of the molecular subsets, and computing a correlation function representing an electrostatic affinity of the two molecular subsets using the transformed expansion coefficients. Embodiments of this method incorporate various combinations of hardware, software, and firmware to perform the steps described below.

Figure 6A:
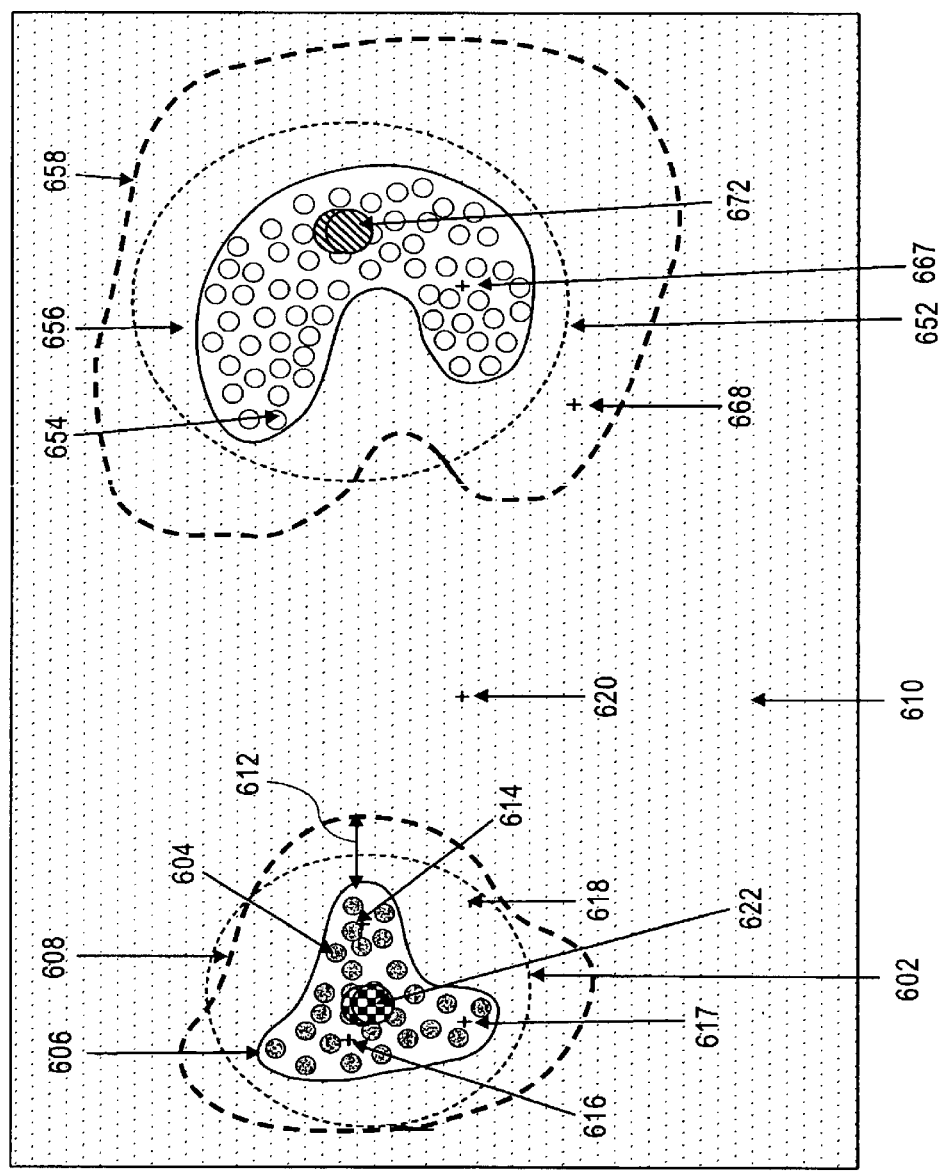

In FIG. 5, in step 502, a first molecular subset 602 and a second molecular subset 652 are provided, as shown in FIG. 6a. The molecular subsets used herein are generally stored as digital representations in a molecule library or other collection such as the molecular combination database 204 of modeling system 200 in FIG. 2. Each molecular subset has a molecular shape, as illustrated in FIG. 6a, wherein the term "molecular shape" generally refers to a volumetric function representing the structure of a molecular subset comprising a plurality of atoms and bonds. Molecular subsets 602 and 652 respectively include a plurality of atoms 604 and 654 that are generally connected by chemical bonds in order to define the structure of each molecular subset. Those skilled in the art will appreciate that the molecular subsets 602 and 652 may have various shapes other than those shown in FIG. 6a. Often the first molecular subset 602 is a ligand, and the second molecular subset 652 is a protein. However, as already discussed in regard to the definition of a molecular subset, the molecular subsets 602 and 652 can have various compositions.

In FIG. 5, in step 503, a first charge distribution is defined for first molecular subset 602, and a second charge distribution may be defined for second molecular subset 652 using a similar methodology. Charges can be conceived of as concentrated at points, but more generally, they are distributed over surfaces or through volumes. For a molecule, the charge distribution typically refers to the plurality of solute entities, representing the charges, partial or otherwise, assigned to constituent atoms and/or chemical groups.

In one embodiment, each solute entity is assigned a charge according to a supplied energy parameter set. An "energy parameter", as used herein, is a numerical quantity representing a particular physical or chemical attribute of a solute entity in the context of the specified energy model for an energy term. An "energy model", as used herein, is a mathematical formulation of one or more energy terms, wherein an energy term represents a particular type of physical and/or chemical interaction. An "energy parameter set", as used herein, is a catalog of energy parameters as pertains to a wide range of chemical species of atoms and bonds for a canonical set of energy models for a number of different energy terms.

An example of an energy term is the electrostatic interaction, which refers to the interaction between two or more solute entities, i.e., ionic, atomic or molecular charges, whether integral or partial charges. As discussed above, a "partial charge" refers to a numerical quantity that represents the effective electrostatic behavior of an otherwise electrically neutral atom, chemical group, or molecule in the presence of an electrical field or another charge distribution. An example of an energy model is a Coulombic electrostatic energy model representing the electrostatic interaction between a pair of atomic or molecular charges in a dielectric medium.

An energy parameter may depend solely on the chemical identity of a solute entity or on the chemical identities of a pair or more of solute entities associated with the given interaction type represented by the energy model; or on the location of the solute entity within the context of a chemical group, a molecular substructure such as an amino acid in a polypeptide, a secondary structure such as an alpha helix or a beta sheet in a protein, or of the molecule as a whole; or on any combination thereof. An example would be the value of charge assigned to a nitrogen atom involved in the peptide bond on the backbone of a lysine residue of a protein with regard to a Coulombic electrostatic energy model. Herein, energy parameter sets includes those defined in conjunction with all-atom or unified atom force fields, often used to estimate the change in energy as a function of the change in conformation of a molecule. Examples of energy parameter sets include those described in AMBER [39][40], OPLS [41], MMFF [42], and CHARMM [43]

In FIG. 5, in step 504, a first molecular surface is defined for first molecular subset 602, and a second molecular surface is defined for second molecular subset 652. The first molecular surface is defined by recognition that, some of atoms 604 are situated along a border or boundary of molecular subset 602. Such atoms are herein referred to as "surface atoms". The surface atoms are proximal to and define a molecular surface 606 for the first molecular subset 602 based on their location.

In one embodiment, the molecular surface 606 can be a solvent accessible molecular surface, which is generally the surface traced by the center of a small sphere rolling over the molecular surface 606. Computational methods for generation of solvent accessible surfaces includes the method presented in Connolly, M. L., "Analytical molecular surface calculation", (1983), *J. Applied Crystallography*, 16, 548–558; all of which is hereby incorporated in its entirety. In another embodiment the molecular surface is defined based on the solute-solvent interface. A second molecular surface 656 is defined in a similar manner for molecular subset 652 based on the subset of atoms 654 that are surface atoms for molecular subset 652.

In FIG. 5, in step 505, a first charge density function, is generated as a representation of the first charge distribution of the first molecular subset 602 over a subset of a volume enclosed by the first molecular surface 606. A charge density function is a volume function representing the charge distribution of a molecular subset and is given by $\rho(\vec{r})$. In FIG. 6a, a position 614 exists within or near one of the atoms 604 which define molecular subset 602 and another position 616 exists outside of and not near any of the atoms 604 of molecular subset 602. Generally, when defining a first charge density function, $\rho_1$, for molecular subset 602, for position 614, and others like it, the charge density function will be nonzero, i.e., $\rho_1 \neq 0$. On other hand, generally, when defining a first charge density function, $\rho_1$, for molecular subset 602, for position 616, and others like it, the charge density function be very small or even zero, i.e., $\rho_1 \cong 0$.

In one embodiment, the first charge density function is defined in terms of a Dirac delta function in order to represent point charges and is given by $\rho_{1,i}(\vec{r}) = C_i q_i \delta(\vec{r})$, where i denotes the $i^{th}$ solute entity, $q_i$ is the net charge of solute entity i, and $C_i$ is a constant, dependent on the chemical identity of the $i^{th}$ solute entity.

In another embodiment, the first charge density function for the first molecular subset 602 is defined as a union of a set of kernel functions. As used herein, "kernel function" is a 3-D volumetric function with finite support that is associated with points in a localized neighborhood about a solute entity.

In one embodiment, each kernel function is dependent on the chemical identity of the associated solute entity. In another embodiment, each kernel function is dependent on the location of the associated solute entity within a chemical group. In yet another embodiment, each kernel function is dependent on the charge of the associated solute entity.

In yet another embodiment, in the case that the solute entity is an atom, the kernel function is a nonzero constant for points within a Van der Waals (vdw) sphere. As used herein, "vdw sphere" is a sphere with radius equal to the Van der Waals radius of an atom of the given type and centered on the atom, and zero at other points. In one example, this nonzero constant has a value of unity. In another example, the nonzero constant has a value such that when multiplied by the volume of the vdw sphere equals the charge assigned to the atom.

Alternatively, as in another embodiment, each kernel function is the charge of the associated solute entity multiplied by a 3-D probability distribution function centered on the solute entity. In yet another embodiment, each kernel function is the charge of the associated solute entity multiplied by a 3-D Gaussian probability distribution function centered on the solute entity and with a known variance. In one example, this variance is a function of the chemical identity of the solute entity or the location of the solute entity within a chemical group.

In yet another embodiment, each kernel function can be the charge of the associated solute entity multiplied by an orthonormal radial basis function. In one embodiment, each kernel function is the charge of the associated solute entity multiplied by a scaled (or unscaled) Laguerre polynomial-based radial basis function. In another embodiment, each kernel function is the charge of the associated solute entity multiplied by a radial/spherical harmonic basis expansion of finite order representing the individual charge distribution of the solute entity. An example of this embodiment is a first charge density function given as follows:

$$\rho_i(\vec{r}) = \frac{q_i}{a_i} S_{10}(r') \qquad [\text{Eqn. 10}]$$

where i denotes the $i^{th}$ solute entity, $r' = |\vec{r} - \vec{A}_i|$ where $\vec{A}_i$ is the center of nearest neighbor atom, $q_i$ is the charge, partial or otherwise of $i^{th}$ solute entity, $S_{10}$ is a scaled radial basis function $S_{nl}$ for n=1 and l=0, and $a_i$ is a scaling factor less than unity, which accounts for the truncation of the charge of the $i^{th}$ solute entity to a small sphere centered on the $i^{th}$ solute entity.

In another embodiment, each kernel function is a quantum mechanical wave function representing the charge distribution of the associated solute entity. As used herein, "quantum mechanical wave function", $\Psi(\vec{r},t)$, describes a quantum mechanical particle, e.g., an electron, an ion, an atom, a molecule, such that its absolute square, $|\Psi(\vec{r},t)|^2$ corresponds to the probability density of finding the particle at position x and time t.

Continuing in FIG. 5, in step 505, a second charge density function, $\rho_2$, is generated as a representation of the second charge distribution of the second molecular subset 652 over a subset of a volume enclosed by the second molecular surface 656 in a manner similar to that used in defining the first charge density function for molecular subset 602.

In FIG. 5, in step 506, a first electrostatic potential function is defined for the first molecular subset 602 when isolated from the second molecular subset 652, based on the electrostatic interaction of the first charge distribution of the first molecular subset 602 with the itself and with various solvent entities in an ambient or aqueous environment of the first molecular subset 602 in isolation. As used herein, the term "ambient environment" refers to the 3-D volume occupied by various solvent entities and may be used interchangeably with ambient material, ambient medium, or even aqueous environment. Alternatively, there may be no solvent entities present in the ambient environment and instead the ambient environment is a vacuum with a dielectric permittivity of $\in_0$.

In one embodiment, the first electrostatic potential function is defined according to the Coulombic electrostatic potential of Eqn. 2 with the assumption of an isotropic dielectric medium representing the polarizable ambient environment of molecular subset 602 in isolation and the representation of the first charge density function is in terms of Dirac delta functions, as discussed above, for point charges.

In another embodiment, the first electrostatic potential function associated with molecular subset 602 in isolation, is a solution to Poisson's equation, whose solution represents the electrostatic potential function for an arbitrary charge density function associated with a solute charge distribution embedded in a dielectric medium, whether isotropic or anisotropic in nature. Poisson's equation is a linear second order elliptical partial differential equation and is given as follows:

$$-\nabla \cdot (\in(\vec{r})\nabla \Phi(\vec{r})) = 4\pi\rho(\vec{r}) \qquad [\text{Eqn. 11}]$$

where, $\Phi(\vec{r})$ is the electrostatic potential at r, $\in(r)$ is the permittivity as a function of position (e.g., $\in_m$ for points in the molecular subset, and $\in_w$ for points in the solvent), and $\rho(r)$ is the arbitrary charge density function. An accurate solution to Poisson's equation, followed by application of Eqn. 3, leads to the total electrostatic energy for the molecular subset that includes both the reaction field and solvent screening effects associated with electrostatic desolvation, as discussed in regard to states 445 and 455 of FIG. 4. However, the effects of an ionic atmosphere are completely ignored in Eqn. 11.

Generally, Eqn. 11 must be solved numerically and an appropriate set of boundary conditions must be specified, i.e., a set of initial values specified on a boundary. A discussion of the relevance of boundary conditions to solutions of partial differential equations (PDEs) and common examples including Neumann, Dirichlet, and Cauchy boundary conditions can be found in Arfken et al., [50].

In another embodiment, the first electrostatic potential function is a solution to the Poisson-Boltzmann equation with suitable boundary conditions and one or more nonzero Debye-Huckel parameters, and represents the electrostatic potential function for the first molecular subset in isolation, including all three types of electrostatic desolvation effects, including the effects of an ionic atmosphere. The Poisson-Boltzmann equation (PBE) is also a second order elliptical partial differential equation, but generally nonlinear, and is given by:

$$-\nabla \cdot (\varepsilon(\vec{r})\nabla \Phi(\vec{r})) + \lambda \bar{\kappa}^2 \sinh\left(\frac{\Phi(\vec{r})}{\lambda}\right) = 4\pi\rho(\vec{r}) \qquad [\text{Eqn. 12}]$$

where $$\lambda = \left(\frac{k_B T}{e_c}\right).$$

The linearized version of Eqn. 12 is given by expanding the hyperbolic sin in terms of $\Phi$ and retaining only the linear component as follows:

$$-\nabla \cdot (\in(\vec{r})\nabla \Phi(\vec{r})) + \bar{\kappa}^2 \Phi(\vec{r}) = 4\pi\rho(\vec{r}) \qquad [\text{Eqn. 13}]$$

In both eqns. 12 and 13, $\Phi(r)$ is the electrostatic potential at r, $\in(r)$ is the permittivity as a function of position (e.g., $\in_m$ for points in the molecular subset, and $\in_w$ for points in the solvent), $\rho(r)$ is the arbitrary charge density function, $\bar{\kappa} = \sqrt{(\in_w \kappa)}$, where $\kappa(r)$ is the Debye-Hu parameter, and $e_C$, $k_B$, and T are respectively, the charge of an electron, Boltzmann constant, and the temperature.

The solutions to eqns. 11–13 are computationally intensive and generally require high memory overhead for accurate solutions, as discussed in references [45][47][50] Moreover, if the conformation of the molecular subset changes, or the molecular subset is brought in close contact to one or more other molecular subsets, the solution must in principle be recomputed as the solute-solvent interface has changed. In practice, however, if the conformational changes are small and the solvent accessibility of solute entities in the molecular subsets do not change appreciably, then previously computed solutions to Eqn. 11, or alternatively eqns. 12 and 13, may be utilized as approximations to the electrostatic potential of the new configuration.

In another embodiment, the first electrostatic potential function is a solution obtained by employing a generalized Born solvation model, and represents the electrostatic potential function for the first molecular subset 602 in isolation, also including the effects of electrostatic desolvation between solute charges and a surrounding ambient environment comprising solvent entities. The Generalized Born (GB) approximation is an alternative approach to calculate charge-charge interactions $W_{ij}$ for pairs of atoms or ions in the presence of continuum solvent, using the following formula $$W_{ij} = \frac{1}{2}\sum_{i \neq j} \frac{q_i q_j}{r_{ij}} - \left[\frac{1}{2}\left(1 - \frac{1}{\varepsilon_w}\right)\sum_{i,j} \frac{q_i q_j}{f^{gb}(r_{ij})}\right] \qquad [\text{Eqn. 14}]$$

where, the first term is the energy in vacuum and the second term is the salvation energy, $\in_w$ is the permittivity of the solvent, $q_i$ is the charge of the $i^{th}$ atom or ion, and $f_{ij}^{gb}$ is a suitably chosen smooth function dependent on the evaluation of various volume integrals over the solvent exclude volume (Still et al., [51] or alternatively on various surface integrals over the solvent accessible surface volume (Ghosh et al., [52])). As already mentioned in the background, while computationally less expensive than numerical solutions to the PBE, the GB solvation models are more complex to evaluate than their Coulombic counterparts.

In another embodiment, the first electrostatic potential function is a solution obtained by employing a molecular dynamics simulation with an explicit solvent dipole model such as those described in [55][56][57].

In FIG. 5, also in step 506 and in a manner similar to that use when defining a first electrostatic potential function for molecular subset 602, a second electrostatic potential function (or function) is defined for the second molecular subset 652 when isolated from the first molecular subset 602, based on the electrostatic interaction of the second charge distribution of the second molecular subset 652 with itself and with solvent entities in an ambient environment of the second molecular subset 652 in isolation.

In FIG. 5, in step 508, a first electrostatic potential field is defined corresponding to a representation of the first electrostatic potential function, generated by the charge distribution associated with molecular subset 602 in isolation, over a first electrostatic potential computational domain 608. The term "electrostatic potential field" should not to be confused with the electric field, a vector function given by $\vec{E}(\vec{r}) = -\nabla \Phi(\vec{r})$ where $\Phi(\vec{r})$ is the electrostatic potential function of a charge distribution.

As used herein, "computational domain" refers to a volume over which the associated function has nonnegligible values. For a function like the electrostatic potential function, which generally has both positive and negative values, "nonnegligible" means that for a point inside the domain the function value has an absolute magnitude above some a priori chosen threshold. Generally, the computational domain represents a topologically connected volume, whether continuous or discrete. The purpose of a finite volumetric computational domain is to reduce the number of computational operations, as well as the amount of required memory overhead and i/o or memory bandwidth. Those skilled in the art should understand that while FIG. 6a shows region 608 represented as a definite band, any volume related to molecular subset 602 can serve as the first electrostatic potential computational domain 608. In some embodiments the electrostatic potential computational domain may include points external to and proximal to the molecular surface 606. In other embodiments the computational domain may also include all of or a portion of the points lying within the volume enclosed by molecular surface 606. A second electrostatic potential computational domain 658 can be defined for molecular subset 652 in a similar manner.

In FIG. 6a, a region 610 outside of both domains 608 and 658 is shown. Position 620 represents a point that is not in either of the computational domains 608 and 658. Generally, point 620 and others like it, will be assigned a value of zero for both the first and second electrostatic potential fields.

In FIG. 6a, regions 608, 658, and 610, either in their entirety or any portions thereof, may lie within an ambient environment. In one embodiment, the ambient environment is a vacuum. In another embodiment, the ambient environment is comprised a plurality of solvent entities. In yet another embodiment, the ambient environment includes water molecular subsets with nonvanishing dipole moments. In yet another embodiment, the ambient environment includes various salt ions. In yet another embodiment, the ambient environment includes an acid or a base such that the solvent is at a nonneutral pH. In yet another embodiment, the ambient environment includes various free radicals. In yet another embodiment, the ambient environment includes various electrolytes. In yet another embodiment, the ambient environment includes various fatty acids. In yet another embodiment, the ambient environment includes a heterogeneous mix of different kinds of solvent entities, such as those already listed.

Positions 617 and 618 represent two different points within the computational domain 608, the first being inside the molecular surface 606 and the latter being external to the volume enclosed by the molecular surface 606. Generally, point 618 and others like it will be assigned a nonzero value for the first electrostatic potential field. Similarly, points 667 and 668 in domain 658 will generally have a nonzero value for the second electrostatic potential field. Moreover, points 618, 668 and 620 will generally have a value zero for both the first and the second charge density function. As will be shown in FIG. 6b, points that lie within both domains 608 and 658 when the two molecular subsets are not in isolation, will generally be assigned nonzero values for both the first and the second electrostatic potential field.

In one embodiment, the computational domain 608 does not include points internal to the molecular surface 606 of molecular subset 602, in which case point 617 would be assigned a value of zero being outside the computational domain for the first electrostatic potential field. In another embodiment, domain 608 is defined by moving a small sphere (or probe sphere) at positions proximal to and external to the first molecular surface 606. In another embodiment, region 608 is defined as the volume swept out by a probe sphere, the center of which moves along the entire first molecular surface 606. In another embodiment, the probe sphere moves along only a portion of the molecular surface 606. In one embodiment, the probe sphere has a constant radius. In FIG. 6a, a domain 608 constructed in this manner is shown and has a characteristic thickness 612 that is equal to the constant radius of the probe sphere.

In another embodiment, the radius of the probe sphere varies as a function of location on the molecular surface 606. Often the radius of the probe sphere is substantially larger than the radius of a typical atom 604 or other solute entity in molecular subset 602. In another embodiment, in order to faithfully represent an appropriate computational domain for the first electrostatic potential function of molecular subset 602, meaning none of the points in region 610 have a significant magnitude for the first electrostatic potential function of molecular subset 602 in isolation, the radius of the probe sphere is substantially larger than the radius, or other characteristic dimension, of a typical solvent entity in the ambient environment of molecular subset 602.

Domain 658 can be constructed for the second electrostatic potential field for molecular subset 652 in a manner similar to domain 608 for molecular subset 602.

In one embodiment the first electrostatic potential field for molecular subset 602 refers to the function formed by truncating the first electrostatic potential function to the first electrostatic potential computational domain 408 as follows:

$$\phi(\vec{r}) = \{\Phi(\vec{r}) \text{ for } \vec{r} \in \vec{D} \text{ and } 0 \text{ for } \vec{r} \notin \vec{D}\} \quad \text{[Eqn. 15]}$$

where $\vec{r}$ is a point in 3-D space, $\Phi(\vec{r})$ is the first electrostatic potential function, $\vec{D}$ is a volumetric computational domain containing points for which $|\Phi(\vec{r})| \geq \Phi_{crit} \geq 0$, $\Phi_{crit}$ is a constant threshold, and $\phi(\vec{r})$ is the first electrostatic potential field. In another embodiment, $\phi(\vec{r})$ is multiplied in Eqn. 15 by a scalar value.

In another embodiment, $\phi(\vec{r})$ is formed instead via the convolution of $\Phi(\vec{r})$ with another function H(r) as follows:

$$\phi(\vec{r})=\{(H*\Phi)(\vec{r}) \text{ for } \vec{r}\in\vec{D} \text{ and } 0 \text{ for } \vec{r}\notin\vec{D}\} \quad [\text{Eqn. 16}]$$

where $\vec{r}$, $\Phi(\vec{r})$, and the domain $\vec{D}$ are as before in Eqn. 15, but $H(\vec{r})$ is an appropriate smoothing filter, e.g., a B-spline or a 3-D Gaussian function. In Eqn. 16, the smoothing filter is intended to smooth out fine scale fluctuations of the electrostatic potential function.

In yet another embodiment, $\phi(\vec{r})$ is defined as the product of a function, $G(\vec{r})$, and the electrostatic potential function, $\Phi(\vec{r})$, as $G(\vec{r})*\Phi(\vec{r})$, where for example $G(\vec{r})$ is a box function, a Gaussian envelope function, or a sigmoid function and the intent of $G(\vec{r})$ is to act as a windowing function. In yet another embodiment, $\phi(\vec{r})$ is defined as the composition of a function, F, and the electrostatic potential function, $\Phi(\vec{r})$, as $F(\Phi(\vec{r}))$, where for example $F(\Phi(\vec{r}))$ is zero for $|\Phi(\vec{r})|$ less than a constant and nonzero otherwise with the intent that F( ) is a threshold function.

A second electrostatic potential field can be defined for the second molecular subset 652 in a similar manner according to the same embodiments.

In FIG. 6b, the first and second molecular subsets 602 and 652 have moved in closer proximity to one another such that the electrostatic potential field of each molecular subset overlaps with solute entities in the other molecular subset. Atoms 604 in molecular subset 602 experience a nonzero value for the second electrostatic potential field associated with the computational domain 658 of molecular subset 652 and, by the same token, atoms 654 in molecular subset 652 experience a nonzero value for the first electrostatic potential field associated with the computational domain 608 of molecular subset 602. Certain atoms 621 of first molecular subset 602 are beyond the second electrostatic potential field domain 658 of second molecular subset 652, such that atoms 621 experience no potential associated with the second charge distribution of molecular subset 652 in this region. The same holds true with respect to atoms 662 in second molecular subset 652 with respect to the first electrostatic potential field domain 608.

In FIGS. 6a–b, those skilled in the art should note that one or more regions within molecular subsets 602 and 652 might be excluded from the calculations, such as regions 622 and 672. In these excluded regions, the corresponding charge density functions and electrostatic potential fields are designated to be zero.

The first and second charge density functions, respectively $\rho_1$ and $\rho_2$, are used in conjunction with the first and second electrostatic potential fields, $\phi_1$ and $\phi_2$, to estimate the change in electrostatic energy upon formation of a potential molecular complex by molecular subsets 602 and 652.

In one embodiment, described with reference to FIG. 7, in step 508 the first molecular subset 602 is represented in discrete space 700 in order to generate in order to generate the relevant charge density functions and electrostatic potential fields. As used herein, "discretization" generally refers to converting a continuous representation to a discrete one, e.g., converting the function from its continuous representation into a series of numbers that best approximates the continuous function as projected onto a set of grid cells.

Figure 8:
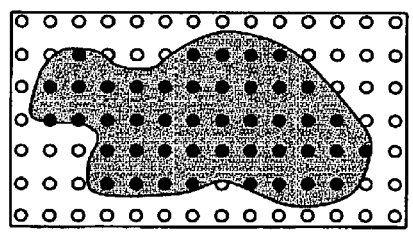
FIG. 8 illustrates how a 2-D continuous shape is discretized in accordance with embodiments of the present invention.

For example, the FIG. 8 illustrates how a general 2-D continuous shape is discretized on a 2-D rectilinear grid. The black dots represent centers of the occupied grid cells; the white dots represent centers of unoccupied grid cells.

Figure 7:
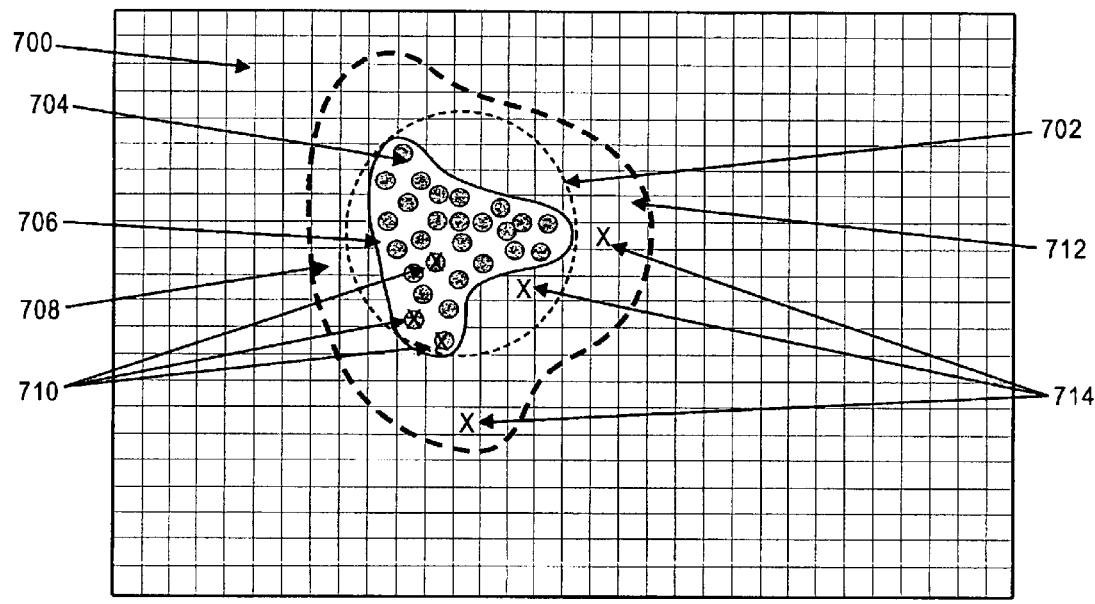
FIG. 7 shows representation of a molecular subset in discrete space for generating discretized charge density functions and electrostatic potential fields, in accordance with embodiments of the present invention.

In FIG. 7, item 702 is a molecular subset analogous to molecular subset 602 of FIGS. 6a–b and domain 708 is a computational domain for the first electrostatic potential field analogous to domain 608 of FIGS. 6a–b. Also in FIG. 7, region 710 is the volume enclosed by the molecular surface 706. Continuing in FIG. 7, the first electrostatic potential field, $\phi_1(\vec{r})$, for a particular grid cell is assigned a nonzero numerical value when the grid cell is inside the computational domain 708, i.e., the grid cell is occupied, and zero otherwise. Similarly, the first charge density function, $\rho_1(\vec{r})$, for a particular grid cell is assigned a zero value for points outside of domain 710 and nonzero otherwise. In one embodiment, the first charge density function is nonzero only for points in domain 710 which are in a localized neighborhood of one of the atoms 704. In another embodiment, the specification for the localized neighborhoods is made based on the functional form for the kernel function locally defining the first charge density function with respect to each atom 704 in molecular subset 702. In one embodiment only a significant fraction of the grid cell must lie within the appropriate domain in order for the grid cell to be considered occupied. In yet another embodiment, those occupied grid cells that, for the relevant discretized function, correspond to an absolute value with magnitude below a chosen numerical threshold, are instead relabeled as unoccupied and the corresponding discretized function value set to zero.

While FIG. 7 shows a two-dimensional cross-sectional view of the charge density and electrostatic potential volumetric functions for the molecular subset 702 as projected onto a 2-D Cartesian grid, those skilled in the art should understand that the principles described above are equally applicable to three-dimensional and higher multidimensional spaces, as well as to other coordinate based representations, where the phrase "coordinate based representation" generally refers to representing a function in terms of coordinates of a coordinate system.

In one embodiment, a Cartesian coordinate based representation is used where each grid cell in three-dimensions is a cuboid. The cuboid grid cells in FIG. 7 with nonzero values for $\phi_1$ are illustrated by example as cells 718 denoting grid cells within the confines of the domain 708. The cuboid grid cells in FIG. 7 with nonzero values for ρ1 are illustrated by example as cells 710 containing one or more, or even parts of, the dark spheres representing atoms within the confines of the molecular surface 702. In this way, values are assigned to $\phi_1$ and $\rho_1$, for each grid cell so that the first electrostatic potential field and the first charge density function for molecular subset 702 are represented as a set of numbers for the entirety of grid cells. In one embodiment, these values are real numbers and can range from (−∞,+∞). In another embodiment, these values are of finite precision. In yet another embodiment, these values are in a fixed-point representation.

The embodiments described above, in regard to the discretization of the first charge density function and the first electrostatic potential field of the first molecular subset, also apply to the discretization of the second charge density function and the second electrostatic potential field of the second molecular subset 602 in step 508.

Figure 9:
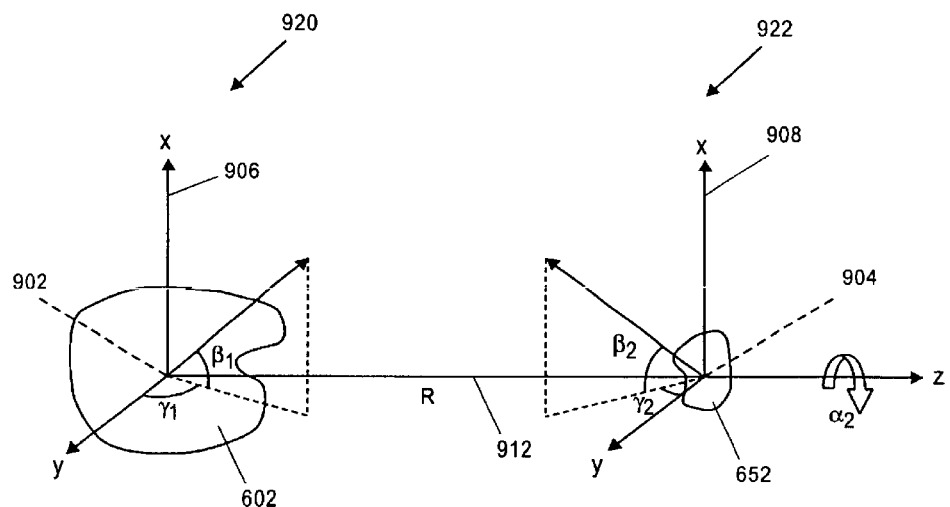
FIG. 9 shows coordinate-based representations of two molecular subsets in a joint coordinate system, in accordance with embodiments of the present invention.

In FIG. 5, in step 510, individual coordinate-based representations for the first and second molecular subsets are defined such that each molecular subset is represented in a coordinate system. A three-dimensional coordinate system is a systematic way of describing points in three-dimensional space using sets of three numbers (or points in a plane using pairs of numbers for a two-dimensional space). An individual coordinate-based representation of the first molecular subset 902 of FIG. 9 includes the first charge distribution and first electrostatic potential field of the first molecular subset 602, using a first coordinate system 906, as shown in FIG. 9. An individual coordinate-based representation of the second molecular subset 652 includes the second charge distribution and second electrostatic potential field of the second molecular subset, using a second coordinate system 908, also shown in FIG. 9.

In one embodiment, the individual coordinate based representations are defined using a spherical polar coordinate system. The spherical polar coordinate system is a three-dimensional coordinate system where the coordinates are as follows: a distance from the origin r, and two angles $\theta$ and $\phi$ found by drawing a line from the given point to the origin and measuring the angles formed with a given plane and a given line in that plane. Angle $\theta$ is taken as the polar (co-latitudinal) coordinate with $\theta \in [0, \pi]$ and angle $\phi$ is the azimuthal (longitudinal) coordinate with $\phi \in [0, 2\pi]$. An illustration is provided in FIG. 10a.

In another embodiment, the individual coordinate based representations are defined using a cylindrical coordinate system (FIG. 10b), which is another three dimensional coordinate system where the coordinates are described in terms of (r, $\theta$, z), where r and $\theta$ are the radial and angular components on the (x, y) plane and z component is the z-axis coming out of the plane.

Figure 10A:
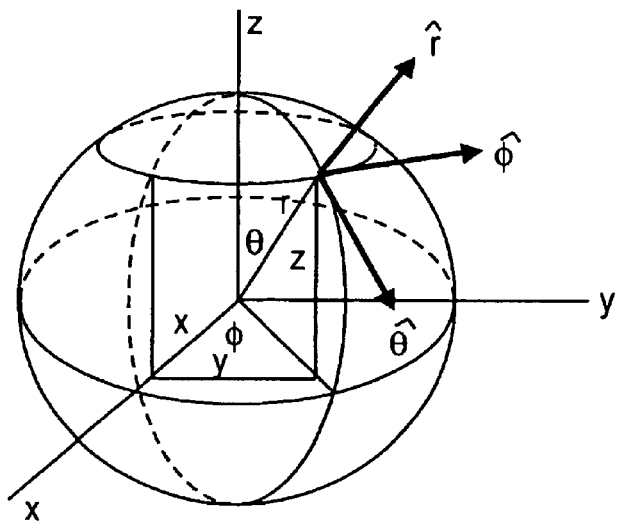
FIGS. 10a, 10b, and 10c show representations of various coordinate systems used in the present invention.
Figure 10B:
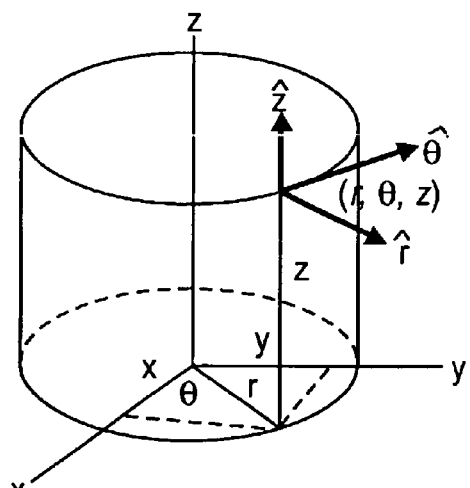
Figure 10C:
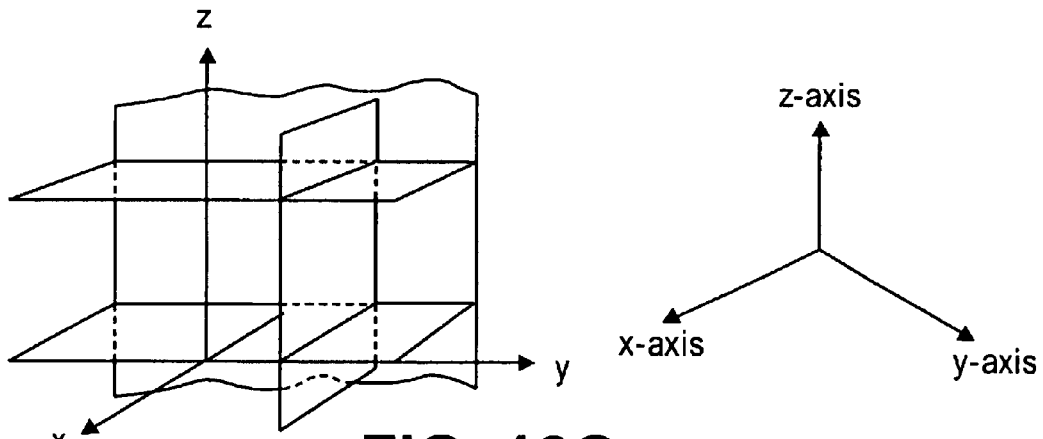

In yet another embodiment, the individual coordinate based representations are defined using a Cartesian coordinate system. The Cartesian coordinate system describes any point in three-dimensional space using three numbers, by using a set of three axes at right angles to one another and measuring distance along these axes. The three axes of three-dimensional Cartesian coordinates, conventionally denoted the x-, y- and z-axes, are chosen to be linear and mutually perpendicular. In three dimensions, the coordinates can lie anywhere in the interval $[-\infty, +\infty]$. An illustration is provided in FIG. 10c. Note that the diagrams in FIGS. 10a, 10b, and 10c are excerpted from web pages available at Eric Weisstein's World of Mathematics on the worldwide web at http://mathworld.wolfram.com/.

For practical purposes of computation in software and/or hardware, the individual coordinate based representations are generally discrete in nature. The individual coordinate based representations are used to compute a reference set of basis expansion coefficients as described below.

A point in space can be represented in many different coordinate systems. It is possible to convert from one type of coordinate based representation to another using a coordinate transformation. A coordinate transformation relabels the coordinates from one coordinate system to another coordinate system. For example, the following equations represent the transformation between Cartesian and spherical polar coordinate systems: {x=r sin $\theta$ cos $\phi$, y=r sin $\theta$ sin $\phi$, z=r cos $\theta$}, and thus a Cartesian coordinate base representation for the first electrostatic potential field for molecular subset 602 can be converted to a spherical polar coordinate based representation for the first electrostatic potential field for molecular subset 602 by applying an appropriate Cartesian to spherical coordinate transform.

In FIG. 5, also in step 510, the individual coordinate based representations 906 and 908 of the first and second molecular subsets are then placed in a joint coordinate system, as shown in FIG. 9. The joint coordinate system is used to represent distinct configurations of the molecular combination. The joint coordinate system is also used to generate new configurations by translating and/or rotating the respective individual coordinate based representations of molecular subsets 602 and 652 relative to one another, as described below. In one embodiment, the joint coordinate system is also used to transform a reference set of basis expansion coefficients for each molecular subset as part of a process to generate shape complementarity scores for each configuration of a molecular combination, as described below.

In one embodiment, a first three-dimensional Cartesian frame 920 is provided for the first molecular subset 602, and a second three-dimensional Cartesian frame 922 is provided for the second molecular subset, as shown in FIG. 9. Herein the term "Cartesian frame" generally refers to the unit vectors in the Cartesian coordinate system, as illustrated in FIG. 10c.

In FIG. 9, the first and second Cartesian frames 920 and 922 are centered at respective molecular centers 902 and 904 of the first and second molecular subsets. The molecular center is generally a point in 3-D space that is designated as the center of the molecular subset. In one embodiment, the molecular center is the geometric center of mass of the molecular subset. In another embodiment, the molecular center is the centroid of the molecular subset. An intermolecular axis 912 is defined as the vector between the molecular centers 902 and 904, and the z-axes of the respective Cartesian frames 920 and 922 are both aligned with the intermolecular axis 912.

In principal, any rotation in three dimensions may be described using three angles. The three angles giving the three rotation matrices are called Euler angles. There are several conventions for Euler angles, depending on the axes about which the rotations are carried out. In a common convention described in FIG. 11, the first rotation is by angle $\phi$ about z-axis, the second is by angle $\theta \in [0, \pi]$ about x-axis, and the third is by angle $\psi$ about z-axis (again). If the rotations are written in terms of rotation matrices B, C and D, then a general rotation A can be written as A=BCD where B, C, and D are shown below and A is obtained by multiplication of the three matrices.

$$D \equiv \begin{bmatrix} \cos\phi & \sin\phi & 0 \\ -\sin\phi & \cos\phi & 0 \\ 0 & 0 & 1 \end{bmatrix},$$ [Eqn. 17]

$$C \equiv \begin{bmatrix} 1 & 0 & 0 \\ 0 & \cos\theta & \sin\theta \\ 0 & -\sin\theta & \cos\theta \end{bmatrix}, B \equiv \begin{bmatrix} \sin\psi & -\cos\psi & 0 \\ \cos\psi & \sin\psi & 0 \\ 1 & 1 & 1 \end{bmatrix}$$

Figure 11:
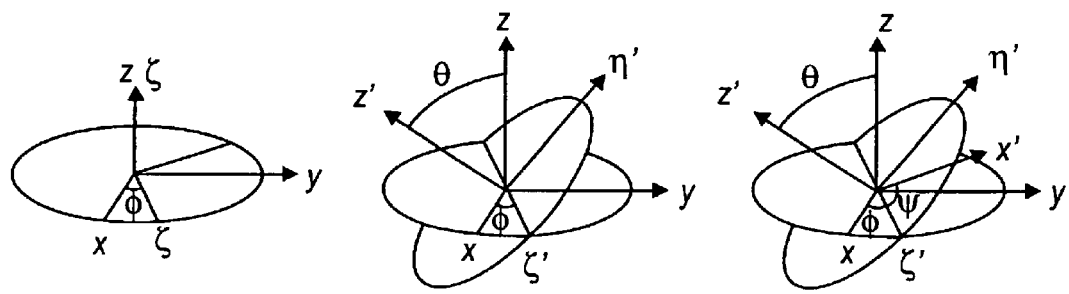
FIG. 11 shows a representation of Euler angles as used in various embodiments of the present invention.
Figure 12:
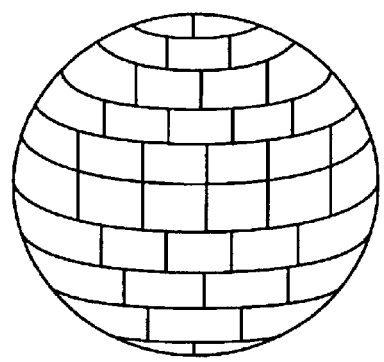
FIG. 12 shows a spherical sampling scheme used in various embodiments of the present invention.

The diagrams in FIG. 11 are excerpted from web pages available at Eric Weisstein's World of Mathematics on the worldwide web at http://mathworld.wolfram.com/.

Another commonly used convention for Euler angles is the well-known "roll, pitch, and yaw" convention encountered in aeronautics. Herein, the roll Euler angle is the Euler angle representing a rotation, $\alpha$, about the z-axis, the pitch Euler angle is the Euler angle representing a rotation, $\beta$, about the y-axis and the yaw Euler angle is the Euler angle representing a rotation, $\gamma$, about x-axis.

In one embodiment, as shown in FIG. 9, R is the intermolecular separation between the first molecular subset 602 and the second molecular subset 652. $\beta_1$ and $\beta_2$ refer to pitch Euler angles representing rotation of each corresponding molecular subset in the x-z plane (i.e., around the y-axis). $\gamma_1$ and $\gamma_2$ refer to yaw Euler angles representing rotations in the y-z plane (i.e., around the x-axis). Therefore, $(\beta_1, \gamma_1)$ are polar and azimuthal Euler angles describing the pitch and yaw of the first molecular subset 602 with respect to the joint coordinate system, ($\beta_2, \gamma_2$) are polar and azimuthal Euler angles describing the pitch and yaw of the second molecular subset 652 with respect to the joint coordinate system, and $\alpha_2$ is a twist Euler angle describing the roll of the second molecular subset 652 with respect to the intermolecular axis. In this way, a set of six coordinates, (R, $\beta_1$, $\gamma_1$, $\alpha_2$, $\beta_2$, $\gamma_2$), completely specify the configuration of the molecular combination, i.e., the relative position and orientation of the molecular subsets.

For practical purposes of computation in software and/or hardware, the coordinate variables of the joint coordinate system, (R, $\beta_1$, $\gamma_1$, $\alpha_2$, $\beta_2$, $\gamma_2$), are generally sampled as a discrete set of values. In other embodiments, the joint coordinate system may be characterized by a different set of parameters other than (R, $\beta_1$, $\gamma_1$, $\alpha_2$, $\beta_2$, $\gamma_2$). For example, ($\alpha_2$, $\beta_2$, $\gamma_2$) may be any one of several sets of permissible Euler angles for molecular subset 652. In another example the angular parameters are not Euler angles. In yet another example, the parameters of the joint coordinate system are expressed in terms of translation and rotation operators, defined below, as applied to ($\mu$, $\nu$, $\phi$) of a prolate spheroidal coordinate system for each molecular subset.

In FIG. 5, as part of the sampling scheme definitions in step 512, an axial sampling scheme is defined in step 514. The axial sampling scheme has a plurality of axial sample points representing a sequence of positions distributed along the intermolecular axis 912 in FIG. 9. As used herein, a "sample point" generally refers to one of a sequence of elements defining the domain of a discretized function, and "sampling scheme" generally refers to a scheme for selecting a sequence of sample points.

An "axial sampling scheme" is a scheme for selecting sample points along an axis or a line (i.e., "axial sample points") and thus provides for relative translation of the individual coordinate based representation 602 of the first molecular subset with respect to the coordinate based representation 652 of the second molecular subset. The allowed values of the intermolecular separation, R, are defined by the axial sampling scheme. In another embodiment, the axial sampling scheme is a regular sampling scheme, which involves selecting sample points at regular intervals. In one embodiment, the axial sampling scheme is an irregular sampling scheme, which involves selecting sample points at irregular intervals according to a nonlinear mapping.

In one embodiment, the endpoints for the axial sampling scheme can be set based on geometric analysis of the electrostatic potential computational domains 608 and 658 of both the first and second molecular subsets. In another embodiment, the geometric analysis constitutes a determination of a maximum radial extent of each molecular subset, and the endpoints of the axial sampling scheme for the first molecular subset 602 are set based on a function of the maximum radial extents of each molecular subset.

In FIG. 5, in step 516, a first spherical sampling scheme is defined for the first molecular subset 602. The first spherical sampling scheme has a plurality of spherical sample points representing a sequence of positions distributed on a surface of a first unit sphere centered on the molecular center of the first molecular subset. In one embodiment, the allowed values of the pitch and yaw Euler angels, ($\beta_1$, $\gamma_1$), for molecular subset 602 are defined by the first spherical sampling scheme.

In one embodiment, the first spherical sampling scheme is the Cartesian product of a regular sampling of the pitch Euler angle ($\beta_1$) and a regular sampling of the yaw Euler angle ($\gamma_1$), where the Cartesian product of two sets A and B is a set of the ordered pairs, $\{(a, b) | a \in A, b \in B\}$ and either set is allowed to be a single element set. This is an example of an irregular sampling scheme in that spherical sample points near the poles will be closer together than at or near the equator.

In another embodiment, the first spherical sampling scheme is defined via an icosahedral mesh covering the two-dimensional surface of a sphere, where "icosahedral mesh" refers to the projection of all vertices and face centers of a many-sided icosahedron onto a unit sphere. In this way an evenly spaced 2-D grid can be constructed on the surface of the sphere as shown in the illustration in FIG. 12. This is an example of a regular sampling scheme in that each spherical sample point corresponds to the center of a 2-D surface element of approximately the same surface area. Similar icosahedral-based regular spherical sampling schemes are discussed in ref. [13].

A second spherical sampling scheme for the second molecular subset 652 can be constructed in the same manner as the first spherical sampling scheme. In this way, the allowed values of the pitch and yaw Euler angels, ($\beta_2$, $\gamma_2$), for molecular subset 652 are defined by this second spherical sampling scheme.

In FIG. 5, in step 518, an angular sampling scheme is defined for the second molecular subset 652. The angular sampling scheme has a plurality of angular sample points representing a sequence of positions distributed on a circumference of a unit circle orthogonal to the intermolecular axis 912 of FIG. 9 that is connects the molecular centers of each molecular subset. The allowed values of the roll Euler angle, $\alpha_1$, for molecular subset 652 are defined by this angular sampling scheme. In one embodiment, the angular sampling scheme is a regular sampling scheme, representing intervals with uniform arc length. In another embodiment, the angular sampling scheme is an irregular sampling scheme.

In FIG. 5, in step 520, a basis expansion with a corresponding set of basis functions is provided. The "basis expansion," as used herein, refers to decomposition of a general function into a set of coefficients, each representing projection onto a particular basis function. One can express this decomposition in a mathematical form, i.e., a general function in M-dimensions, $f(\vec{x})$, can be written in terms of a set of basis functions $B_i(\vec{x})$, as $$f(\vec{x}) = \sum_{i=0}^{i=\infty} a_i B_i(\vec{x}) \qquad \text{[Eqn. 18]}$$

where, $i \in \{0, 1, 2, \ldots \infty\}$ refers to a specific basis function, $\vec{x}$ is a set of M coordinates, and each basis function, $B_i$, is generally one member of a set of M-dimensional functions in a function space such that any general function in the function space can be expressed as a linear combination of them with appropriately chosen coefficients. In Eqn. 18, $a_i$ is the expansion coefficient associated with the $i^{th}$ basis function, $B_i$.

The choice of basis expansion and hence the choice of a set of basis functions is often dictated by the choice of coordinate system for representation of the general function in question. Characteristics and/or underlying symmetries of the given function can also influence the choice of basis expansion.

For practical purposes of computation in software and/or hardware, the upper limit of the summation in Eqn. 18 has a finite value, N. This upper limit is referred to as the order of the basis expansion. This leads to the following mathematical form for the basis expansion:

$$f(\vec{x}) = \sum_{i=0}^{i=N} a_i B_i(\vec{x}) \qquad \text{[Eqn. 19]}$$

and the plurality of expansion coefficients $\{a_1, a_2, a_3, \ldots, a_N\}$ are known as a set of expansion coefficients.

Such an approximation, as in Eqn. 19, necessitates the existence of representation errors because the basis expansion is now of finite order. However, in general, if N is chosen to be sufficiently large, the representation errors will be small for all but the most intransigent of functions. In one embodiment, the order of the expansion is predetermined and is much larger than unity, e.g., $N \geq 30$. In another embodiment, the order of the expansion is adaptively determined based on a preliminary quantitative analysis of representation errors for trial values of the expansion order, and may therefore be of different magnitude for different pairs of molecular subsets 602 and 652 based on the characteristics of their respective charge density function and electrostatic potential field.

In one embodiment, the basis expansion is an orthogonal basis expansion comprising a plurality of mutually orthogonal basis functions. If the basis functions satisfy the following mathematical condition, they are called mutually orthogonal:

$$\int_{\vec{x}} B_i(\vec{x}) B_j(\vec{x}) d\vec{x} = C_{ij} \delta_{ij} \qquad \text{[Eqn. 20]}$$

where $C_{ij}$ is a constant (not necessarily unity when i=j), $\delta_{ij}$ is the usual Kronecker delta, and the integral is over the entire M-dimensional space.

For an orthogonal basis expansion, an expansion coefficient, as, corresponding to a particular basis function, $B_i$, can be written as follows:

$$a_i = \left(\frac{1}{C_{ii}}\right) \int_{\vec{x}} f(\vec{x}) B_i(\vec{x}) d\vec{x} \qquad \text{[Eqn. 21]}$$

where $C_{ii}$ is a constant.

However, once again for the practical purposes of computation, the expansion coefficients are discretized by converting the integral in Eqn. 21 to a finite summation. In the case of a set of expansion coefficients for an orthogonal basis expansion, the discretized expansion coefficient, $a_i$, for an orthonormal basis function, $B_i$, takes the following form:

$$a_i = \left(\frac{1}{C_{ii}}\right) \sum_c f(\vec{x}_c) B_i(\vec{x}_c) \qquad \text{[Eqn. 22]}$$

where the summation is over the discrete points c, i.e., $\vec{x}_c$ is a sample point in the M-dimensional space represented here by $\vec{x}$.

In another embodiment, the basis expansion is an orthonormal basis expansion comprising a plurality of mutually orthonormal basis functions. If the basis functions are mutually orthogonal and in Eqn. 22, $C_{ii}$ is unity for all relevant basis functions, then the basis functions are said to be mutually orthonormal. This similarly simplifies the expressions for $a_i$ in eqns. 21 and 22.

A general 3-D function in spherical polar coordinates can be represented in terms of a radial/spherical harmonics basis expansion comprising a plurality of basis functions, each basis function defined as the product of one of a set of orthonormal radial basis functions, $R_{nl}(r)$, and one of a set of real-valued spherical harmonics basis functions, $y_l^m(\theta,\phi)$, as follows:

$$f(r, \theta, \phi) = \sum_{nlm}^{n=N} a_{nl} R_{nl}(r) y_l^m(\theta, \phi) \qquad \text{[Eqn. 23]}$$

where $\{a_{nlm}\}$ is the set of radial/spherical harmonics expansion coefficients, $(r, \theta, \phi)$ are the spherical coordinates of a point in 3D space, n=[1, N], integer, l=[0, n−1], integer, m=[−1, 1], integer.

The usage of such an expansion is common practice in the quantum mechanical description of numerous atomic and molecular orbitals. Hence the indices n, l, and $|m| \geq 0$ are often respectively referred to as the principal quantum number, angular quantum (or orbital) number and azimuthal (or magnetic moment) quantum number.

In Eqn. 23, each radial basis function, $R_{nl}(r)$, is a 1-D orthonormal basis function depending solely on the radius, r.

The form for the radial basis functions is often chosen based on the problem at hand, e.g., the scaled hydrogen atom radial wave function in quantum mechanics is based for example on associated Laguerre polynomials (Arfken et al) as follows:

$$R_{nl}(r) = \left[\left(\frac{2}{k^{3/2}}\right) \frac{(n-l-1)!}{\Gamma\left(n+\frac{1}{2}\right)}\right]^{1/2} e^{-\rho/2} \rho^{l/2} L_{n-l-1}^{l+1/2}(\rho) \qquad \text{[Eqn. 24]}$$

where the square root term in the normalization factor, $\rho$ is the scaled distance, $\rho = r^2/k$, k is the scaling parameter, $\Gamma$ is the gamma function, and L( ) are the associated Laguerre polynomials; where a general Laguerre polynomial is a solution to the Laguerre differential equation given by:

$$xy'' + (1-x)y' + \lambda y = 0 \qquad \text{[Eqn. 25]}$$

and the associated Laguerre polynomials themselves are given explicitly as follows:

$$L_n^k(x) = \sum_{m=0}^{n} \left((-1)^m \frac{(n+k)!}{(n-m)!(k+m)!m!} x^m\right), \qquad \text{[Eqn. 26]}$$

according to Rodrigues' formula.

Various radial basis functions can be used in accordance with embodiments of the present invention. In one embodiment, the radial basis functions include the scaled Laguerre polynomial-based functions of Eqn. 24. In another embodiment, the radial basis functions include unscaled forms of Eqn. 24 in terms of r (not $\rho$) and without the normalization constants. In yet another embodiment the radial basis functions include a Bessel function of the first kind $J_n(r)$). In yet another embodiment the radial basis functions include a Hermite polynomial function ($H_n(r)$). In other embodiments, the radial basis functions include any mutually orthonormal set of basis functions that depend on the radius in a spherical coordinate system centered on the respective molecular center of the molecular subset in question.

In Eqn. 23, each real-valued spherical harmonic basis function, $y_l^m(\theta, \phi)$, is a 2-D orthonormal basis function depending on the angular variables $(\theta, \phi)$ of a spherical coordinate system centered on the molecular center of the each molecular subset. Spherical harmonics satisfy a spherical harmonic differential equation, representing the angular part of the Laplace's equation in spherical coordinate system:

$$\frac{\Phi(\phi)}{\sin\theta}\frac{d}{d\theta}\left(\sin\theta\frac{d\Theta}{d\theta}\right) + \frac{\Theta(\theta)}{\sin^2\theta}\frac{d^2\Phi(\phi)}{d\phi^2} + l(l+1)\Theta(\theta)\Phi(\phi) = 0. \quad \text{[Eqn. 27]}$$

The spherical harmonics themselves are complex-valued, separable functions of $\theta$ and $\phi$, and are given in terms of an associated Legendre polynomial, $P_l^m(x)$, by the equation, $$Y_l^m(\theta, \phi) \equiv \sqrt{\frac{2l+1}{4\pi}\frac{(l-m)!}{(l+m)!}}\, P_l^m(\cos\theta)e^{im\phi}, \quad \text{[Eqn. 28]}$$

where the associated Legendre polynomial is given by:

$$P_l^m(x) = \frac{(-1)^m}{2^l l!}(1-x^2)^{m/2}\frac{d^{l+m}}{dx^{l+m}}(x^2-1)^l \quad \text{[Eqn. 29]}$$

Figure 13:
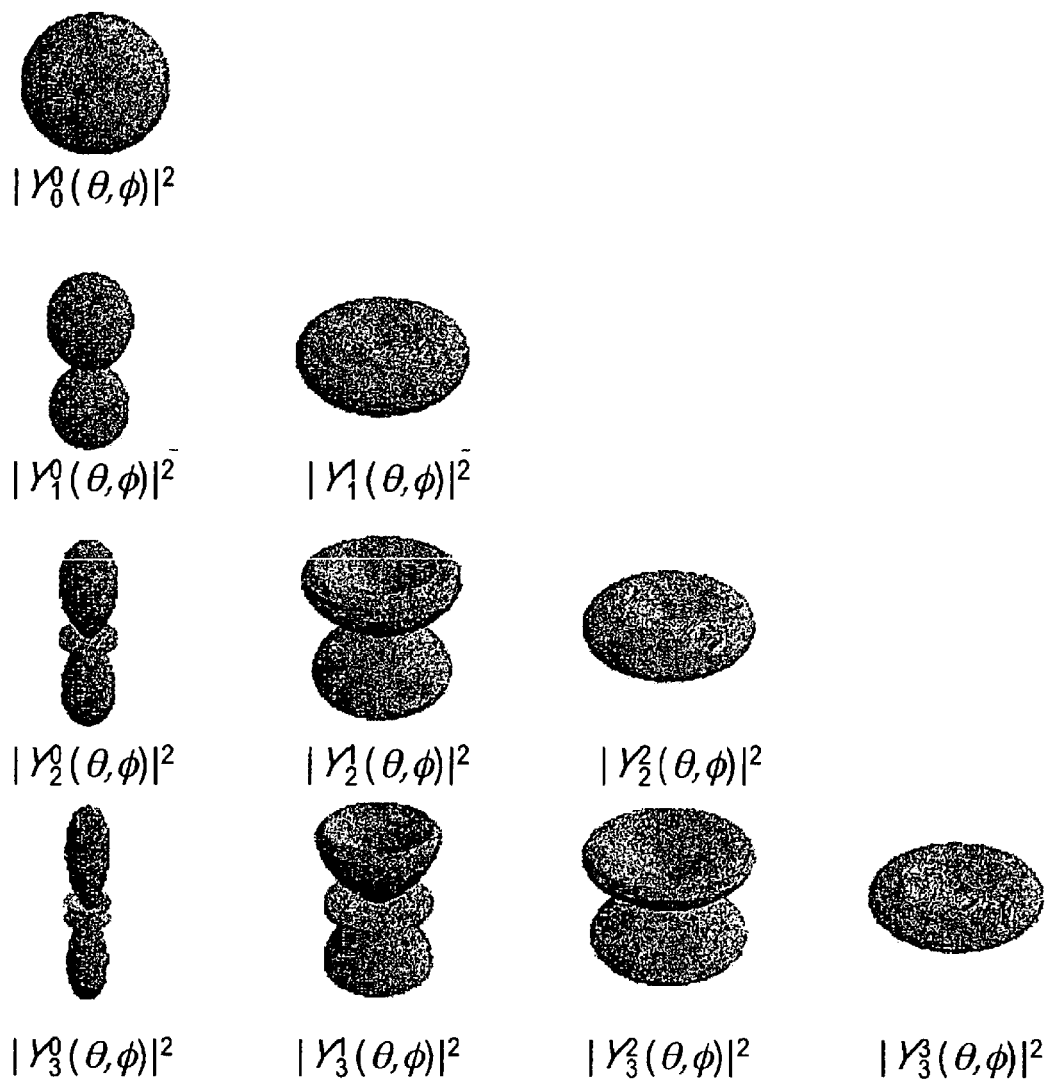
FIG. 13 is an illustration of spherical harmonics function.

Spherical harmonics can be used to represent 3-D molecular shapes in the context of molecular docking, as described in Kita II. An illustration of the first few spherical harmonics is shown in FIG. 13, in terms of their amplitudes.

Real-valued spherical harmonics functions, $y_l^m(\theta, \phi)$, can be obtained from suitable linear combinations of $Y_l^m$ and its complex conjugate $Y^*{}_l^m$ in order to represent the real and imaginary parts of $Y_l^m$, as follows:

$$y_l^m(\theta, \phi) = \begin{cases} (Y_l^m(\theta, \phi) + Y_l^m(\theta, \phi)^*)/\sqrt{2} & m > 0 \\ (Y_l^0(\theta, \varphi)) & m = 0 \\ -i(Y_l^m(\theta, \phi) - Y_l^m(\theta, \phi)^*)/\sqrt{2} & m < 0 \end{cases} \quad \text{[Eqn. 30]}$$

Based on Eqn. 23, the expansion coefficients $\{a_{nlm}\}$ coefficients for an arbitrary 3-D volume function $f(r, \theta, \phi)$ are defined as:

$$a_{nlm} = \int f(r,\theta,\phi)R_{nl}(r)y_l^m(r,\theta,\phi)dV \quad \text{[Eqn. 31]}$$

where the integral is over the extent of function $f(r, \theta, \phi)$ in spherical coordinates and $dV$ is a differential volume element in spherical coordinates.

The discretized analog of the expansion coefficients in Eqn. 31 are given by:

$$a_{nlm} = \sum_c f(r_c, \theta_c, \phi_c)R_{nl}(r_c)y_l^m(r, \theta, \phi)\Delta V_c \quad \text{[Eqn. 32]}$$

where the summation is over all grid cells, c, and $(r_c, \theta_c, \phi_c)$ are the spherical coordinates of the center of grid cell c and $\Delta V_c$ is the volume of grid cell c. Eqn. 32 may then be used to represent various volumetric functions associated with a given molecular subset via corresponding sets of expansion coefficients.

Now instead, in one embodiment of the present invention, the following variants of Eqn. 32 that are displayed in Eqn. 33 & 34, are used in step 520 of FIG. 5, to respectively describe the first electrostatic potential field and the first charge density function of molecular subset 602 in terms of corresponding sets of expansion coefficients:

$$\varphi_{nlm}^1 = \sum_c \varphi_1(r_c, \theta_c, \phi_c)R_{nl}(r_c)y_l^m(\theta_c, \phi_c)\Delta V_c \quad \text{[Eqn. 33]}$$

$$\rho_{nlm}^1 = \sum_c \rho_1(r_c, \theta_c, \phi_c)R_{nl}(r_c)y_l^m(\theta_c, \phi_c)\Delta V_c \quad \text{[Eqn. 34]}$$

where again the summation is over all grid cells, c, $(r_c, \theta_c, \phi_c)$ are the spherical coordinates of the center of grid cell c and $\Delta V_c$ is the volume of grid cell c. But now $\phi_1(r_c, \theta_c, \phi_c)$ and $\rho_1(r_c, \theta_c, \phi_c)$ are respectively the coordinate based representations based on a spherical polar coordinate system for the first electrostatic potential field and the first charge density function for molecular subset 602, and $\{\phi^1_{nlm}\}$ and $\{\rho^1_{nlm}\}$ are corresponding sets of expansion coefficients for an initial pose of molecular subset 602, herein designated as reference sets of expansion coefficients for molecular subset 602.

In one embodiment of the present invention, the grid cells in Eqn. 32 are cuboids from a Cartesian coordinate system and the spherical 3-tuples $(r_c, \theta_c, \phi_c)$ are converted 'on-the-fly' to Cartesian 3-tuples $(x_c, y_c, z_c)$ using a suitable coordinate transformation, for easy addressing of the function, f, over a lattice representation stored in a computer-readable memory. In another embodiment the grid cells can be a varying volume, $\Delta V_c$. In yet another embodiment the grid cells represent small volumes in a spherical coordinate system. In yet another embodiment the grid cells represent small volumes in a cylindrical coordinate system.

Similarly, in step 520 of FIG. 5, the coordinate based representations for the second electrostatic potential field and the second charge density function for molecular subset 652, respectively, $\phi_2$ and $\rho_2$, are represented via use of eqns. 33 & 34 in terms of sets of expansion coefficients, namely $\{\phi^2_{nlm}\}$ and $\{\rho^2_{nlm}\}$, for an initial configuration of molecular subset 652, also designated herein as reference sets of expansion coefficients but now for molecular subset 652.

Thus in step 520 of FIG. 5, altogether there are four sets of reference expansion coefficients computed for the two molecular subsets 602 and 652, each corresponding to an electrostatic potential field or a charge density function for one of the molecular subsets. Once again, the reference sets for molecular subset 602 are designated as $\{\phi^1_{nlm}\}$ and $\{\rho^1_{nlm}\}$, respectively, and the reference sets for molecular subset 602 are designated as $\{\phi^2_{nlm}\}$ and $\{\rho^2_{nlm}\}$ respectively. In another embodiment, the four reference sets of expansion coefficients are computed using Eqn. 22 where the set of basis functions $\{B_i\}$ correspond to a general basis expansion, i.e., need not be the radial/spherical harmonics expansion of Eqn. 23, upon which eqns. 31–34 are predicated.

As discussed before in regard to various embodiments as related to eqns. 11–13 and even Eqn. 2, the generation of the electrostatic potential function, and hence the electrostatic potential field, $\phi$, for a molecular subset is both computationally intensive and in the cases of Eqn. 11–13 often requires high memory overhead and high memory and/or i/o bandwidth in order to achieve accurate solutions. In one embodiment, as $\phi$ refers in Eqn. 31 to the coordinate based representation of the electrostatic field for a molecular subset in isolation, the first electrostatic potential field is precomputed ahead of time for an initial configuration of molecular subset 602 and stored in a computer-addressable memory for later retrieval. Then, during step 520 of FIG. 5, the appropriate discretized values for $\phi_1$ are retrieved from storage and then used to generate the corresponding reference set of expansion coefficients, $\{\phi^1_{nlm}\}$, as per Eqn. 31.

In one embodiment of the present invention, the set of values comprising $\{f(r_c, \theta_c, \phi_c)\}$ for all grid cells c (both occupied and unoccupied) in a coordinate based representation for the first electrostatic potential field of molecular subset 602 are converted to a stream or an array of Cartesian-based values $\{f(x_c, y_c, z_c)\}$ via a suitable coordinate transformation and stored on a computer-readable and recordable medium for future retrieval. Later, when the stored values are to be used in the context of Eqn. 33 to compute expansion coefficients, the stored values are first retrieved and then converted back into $\{f(r_c, \theta_c, \phi_c)\}$ by an inverse coordinate transformation.

Similarly the values corresponding to the coordinate based representation for the second electrostatic potential field for molecular subset 652 can be precomputed, stored and retrieved in a similar manner, including the use of coordinate transformations to convert back in forth from a spherical polar coordinate based representation to a Cartesian coordinate based representation, more suitable for storage in a computer-addressable memory. The same embodiments can be applied to the charge density functions of either molecular subset in order to facilitate efficient computation of the reference sets of expansion coefficients $\{\rho^1_{nlm}\}$ and $\{\rho^2_{nlm}\}$ as per Eqn. 34.

In another embodiment, in the context of a hardware implementation of the invention, the possibly expensive precomputation step of $\{\phi(r_c, \theta_c, \phi_c)\}$, and alternatively $\{\phi(z_c, y_c, z_c)\}$, associated with the previous embodiments, can be performed off-chip in software or via other dedicated hardware. In yet another embodiment, also in the context of a hardware implementation of the invention, the computer-addressable memory used to store the coordinate based representations of the electrostatic potential field resides off-chip, e.g., in a DRAM module or in an attached I/O storage device, or other external memory. In another embodiment, the same can be applied to the precomputation, storage, and retrieval of the coordinate based representations of one or both of the charge density functions in the context of a hardware implementation of the invention. The aforementioned embodiments also apply to an implementation of the present invention in a mixed software/hardware system.

In FIG. 5, in step 522, the method continues with providing a translation operator representing translation of the coordinate based representation 906 of the first molecular subset with respect to the coordinate based representation 908 of the second molecular subset in the joint coordinate system displayed in FIG. 9. The term "translation operator" refers to an operator that, when applied to a point, results in the point's translation along a vector as defined by the translation operator. The operator can be applied to any collections of points as a subset of 3-D space, e.g., a line, a curve, a surface, or a volume.

In one embodiment, the translation operator is a matrix function of the displacement along the intermolecular axis 612 between the first and second molecular subsets. Then the translation operator can be directly applied to the set of reference expansion coefficients for both the first charge density function and the first electrostatic potential field of molecular subset 602, while leaving molecular subset 652 untouched. Note in one embodiment of the present invention, the coordinate based representations for the first charge density function and the first electrostatic potential field of molecular subset 602 are translated together in that they do translate (i.e., slip) relative to one another. In another embodiment, molecular subset 602 is held fixed and the translation operator is directly applied to the set of reference expansion coefficients for the second charge density function and the second electrostatic potential field of molecular subset 652.

In one embodiment, using the joint $(R,\beta_1,\gamma_1,\alpha_2,\beta_2,\gamma_2)$ coordinate system of FIG. 9, in conjunction with the radial/spherical harmonics expansion of Eqn. 23, the translation operator representing the translation of the coordinate based representation of the internal volume function for molecular subset 602 from R=0 (meaning molecular centers of molecular subsets 902 and 904 are the same point in FIG. 9) to R>0 is directly applied to the reference sets of expansion coefficients $\{\rho^1_{nlm}\}$ and $\{\phi^1_{nlm}\}$ for the first charge density function and the first electrostatic potential field for molecular subset 602 according to the following rule:

$$\tilde{\rho}^{1,2}_{nlm}(R) = \sum_{n'l'} \rho^{1,2}_{n'l'm'} K_{nn'll'|m|}(R)\delta_{mm'} \qquad [\text{Eqn. 35}]$$

$$\tilde{\varphi}^{1,2}_{nlm}(R) = \sum_{n'l'} \varphi^{1,2}_{n'l'm'} K_{nn'll'|m|}(R)\delta_{mm'}$$

where $\{\tilde{\rho}_{nlm}^{1}\}$ and $\{\tilde{\phi}_{nlm}^{1}\}$ are the new translated set of expansion coefficients for the first charge density function and the first electrostatic potential field for molecular subset 602, (n, l, m) are quantum numbers for the new translated expansion coefficient, (n', l', m') are quantum numbers for the one of the set of reference expansion coefficients, the summation is over all possible values of n' and l', $\delta_{mm'}$ is the standard Kronecker delta, and $K_{nn'll'|m|}$ are matrix elements of a translation matrix function with values equal to resultant overlap integrals between two different basis functions of the radial/spherical harmonics expansion, with quantum numbers n, l, m and n', l', m' respectively, separated by a distance R, and which are nonzero only when m=m'.

The exact form for the translation matrix $K_{nn'll'|m|}$ depends on the choice of radial basis functions used in Eqn. 23. Eqn. 35 has been used previously to efficiently derive a new set of translated expansion coefficients from a reference set of expansion coefficients as described in Danos, M., and Maximon, L. C., "Multipole matrix elements of the translation operator", J. Math. Phys.,6(1),766–778, 1965; and Talman, J. D., "Special Functions: A Group Theoretical Approach", W. A. Benjamin Inc., New York, 1968; all of which are hereby incorporated by reference in their entirety.

In one embodiment, the entire set of translation matrix elements, $K_{nn'll'|m|}$, may be precomputed for all relevant values of n, n', l, l', & m for a finite order of expansion, N, and stored on a computer-readable and recordable medium for future retrieval as needed. This is advantageous since calculation of the overlap integrals which define each translation matrix element can be very costly and yet for a given finite order of expansion and a given form for the radial basis functions used in Eqn. 22, the calculations need to be done only once and the resultant K-matrix is applicable to any molecular subset regardless of size and shape. Moreover, for the large values of N, the number of translation matrix elements is $O(N^5)$.

In FIG. 5, in step 524, the method continues with providing a first rotation operator representing rotation (change of orientation) of the coordinate based representation 906 of the first charge density function and the first electrostatic potential field for the first molecular subset 602 with respect to the Cartesian frame 920 co-located with the molecular center 902 of molecular subset 602 in the joint coordinate system of FIG. 9. Note in one embodiment of the present invention, the coordinate based representations for the first charge density function and the first electrostatic potential field of molecular subset 602 are rotated together in that they do rotate relative to one another.

The term "rotation operator" generally refers to an operator that, when applied to a point, results in the point's rotation about an axis as defined by the rotation operator. The operator can be applied to any collections of points, e.g., a line, a curve, a surface, or a volume. As described with regard to Eqn. 17, any rotation in 3-D can be represented by a set of three Euler angles.

In one embodiment, different orientations of the coordinate based representation 906 of the first charge density function and the first electrostatic potential field for the first molecular subset 902 with respect to the Cartesian frame 920 are generally represented by a set of three Euler angles representing roll ($\alpha_1$), pitch ($\beta_1$), and yaw ($\gamma_1$), as shown in FIG. 9. In another embodiment the roll angle ($\alpha_1$), describing rotation with respect to the z-axis of the Cartesian frame 920, is ignored since with respect to the common z-axis of the joint coordinate system only the relative orientation between the two molecular subsets is relevant. Then the orientation of molecular subset 902 with respect to Cartesian frame 920 is fully described by a pair of Euler angles ($\beta_1, \gamma_1$) In another embodiment the angles need not be Euler angles and in fact depend on the choice of joint coordinate system.

In one embodiment, the first rotation operator is a matrix function of ($\alpha_1, \beta_1, \gamma_1$). Then the first rotation operator can be directly applied to the set of reference expansion coefficients for the first charge density function and the first electrostatic potential field of molecular subset 602. In one embodiment, using the joint $(R, \beta_1, \gamma_1, \alpha_2, \beta_2, \gamma_2)$ coordinate system of FIG. 9, in conjunction with the radial/spherical harmonics expansion of Eqn. 23, the first rotation operator representing the rotation of the coordinate based representation of the first charge density function and the first electrostatic potential field for molecular subset 602 from ($\alpha_1=0, \beta_1=0, \gamma_1=0$) to arbitrary ($\alpha_1, \beta_1, \gamma_1$) ) is directly applied to the reference set of expansion coefficients $$\{\tilde{p}^1_{nlm}\} \text{ and } \{\tilde{\varphi}^1_{nlm}\}$$

for the first charge density function and the first electrostatic potential field for molecular subset 602 according to the following rule:

$$\tilde{p}^1_{nlm} = \sum_{m'=-l}^{m'=+l} p^1_{nlm'} R^l_{mm'}(\alpha_1, \beta_1, \gamma_1)$$ [Eqn. 36]

$$\tilde{\varphi}^1_{nlm} = \sum_{m'=-l}^{m'=+l} \varphi^1_{nlm'} R^l_{mm'}(\alpha_1, \beta_1, \gamma_1)$$

where $$\{\tilde{p}^1_{nlm}\} \text{ and } \{\tilde{\varphi}^1_{nlm}\}$$

are the new rotated set of expansion coefficients, (n, l, m) are the quantum numbers for the new rotated expansion coefficient, m' denotes the magnetic moment quantum number for the set of reference expansion coefficients, $$\{p^1_{nlm}\} \text{ or } \{\varphi^1_{nlm}\},$$

the summation is over all possible values of m', and $R_{mm'}^1$ are matrix elements of a block diagonal matrix such that each $R^{(l)}$ denotes a $(2l+1)*(2l+1)$ block sub matrix.

This property that the harmonic expansion coefficients transform amongst themselves under rotation in a similar way in which rotations transform the (x, y, z) coordinates in Cartesian frame was first presented in the context of molecular shapes by Leicester, S. E., Finney, J. L., and Bywater, R. P., in "A Quantitative Representation of Molecular-Surface Shape. 1. Theory and Development of the Method" (1994), J. Mathematical Chemistry, 16(3–4), 315–341; all of which is hereby incorporated by reference in its entirety.

For an arbitrary Euler rotation with angles ($\alpha, \beta, \gamma$) and for a pair of positive magnetic moment quantum numbers, m and m', the individual matrix elements are computable in terms of Wigner rotation matrix elements, $d^1_{mm'}(\beta)$, as follows:

$$R_{mm'}^1(\alpha,\beta,\gamma) = d_{mm'}^1(\beta)\cos(m'\gamma+m\alpha) + (-1)^m d_{-mm'}^1(\beta)\cos(m'\gamma+m\alpha)$$ [Eqn. 37]

where $d^1_{mm'}(\beta)$, the elements of the Wigner rotation matrix are given by:

$$d^l_{mm'}(\beta) = \sum_{k=k_1}^{k_2} (-1)^{k+m'-m} C(l, m, k)$$ [Eqn. 38]

$$\left(\cos\frac{\beta}{2}\right)^{2l+m-m'-2k} \left(\sin\frac{\beta}{2}\right)^{2k+m'-m}$$

with $k_1$=max (0, m−m'), $k_2$=min(1−m', 1+m), and C(l,m,k) being a constant function. Similar forms exist for the other eight possible signed pairs of m and m'. For further details on Wigner matrix elements, refer to Su, Z., and Coppens, P., J. Applied Crystallography, 27, 89–91 (1994); all of which is hereby incorporated by reference in their entirety. In one embodiment, where ($\alpha_1=0$) for all rotations of molecular subset 602, Eqn. 37 simplifies and the $R^1_{mm'}$ matrix elements are functions of ($\beta_1, \gamma_1$) alone.

For basis expansions other than the radial/spherical harmonics expansion of Eqn. 23, eqns. 36 and 37 will be replaced by appropriate analogs depending on the choice of angular basis functions, with suitable indices representing each basis function.

In FIG. 5, also in step 524, the method continues with providing a second rotation operator representing rotation of the coordinate based representation 908 of the second charge density function and the second electrostatic potential field of molecular subset 652 with respect to the Cartesian frame 922 co-located with the molecular center 904 of molecular subset 652 in the joint coordinate system. Note in one embodiment of the present invention, the coordinate based representations for the second charge density function and the second electrostatic potential field of molecular subset 652 are rotated together in that they do rotate relative to one another.

As with the first molecular subset 602, different orientations of the coordinate based representation 908 of the second charge density function and the second electrostatic potential field of for the second molecular subset 652 with respect to the Cartesian frame 922 are generally represented by a set of three Euler angles representing roll ($\alpha_2$), pitch ($\beta_2$), and yaw ($\gamma_2$), as shown in FIG. 9. In another embodiment the angles need not be Euler angles and in fact depend on the choice of joint coordinate system.

In one embodiment, the second rotation operator is a matrix function of ($\alpha_2, \beta_2, \gamma_2$). Then the second rotation operator can be directly applied to the set of reference expansion coefficients for the second charge density function and the second electrostatic potential field of molecular subset 652 in a manner similar to the application of the first rotation operator to the set of reference expansion coefficients for the first charge density function and the first electrostatic potential field of molecular subset 602.

In one embodiment, the matrix function representing the second rotation operator can be split up into two distinct rotation operators, the first being a function of $(\beta_2, \gamma_2)$ alone (i.e., $\alpha_2=0$) and the second being a function of the roll Euler angle, $\alpha_2$, alone (i.e., $(\beta_2=0, \gamma_2=0)$). Thus either of these two rotation operators can be applied first to the reference set of expansion coefficients in order to obtain an intermediate rotated set of coefficients and the remaining operator then applied in succession in order to generate a final resultant set of rotated coefficients. In such an embodiment, the two rotation operators are designated as the second and third rotation operators in order to avoid confusion regarding the first rotation operator for molecular subset 602. Moreover, in this embodiment, when in conjunction with the radial/spherical harmonics expansion of eqns. 23, 36, and 37 can be applied for determining the result of application of each rotation operator to the second molecular subset 652, in which case the application of the third rotation operator reduces to simple multiplication by constants and sines and cosines of the quantity (m'α).

In another embodiment, similar to that described in Kita II, the simplified form for the third rotation operator permits direct application of the third rotation operator to electrostatic affinity scores themselves, as described below, as opposed to intermediate rotated expansion coefficients for the second charge density function and the second electrostatic potential field of associated with the second molecular subset 652.

In FIG. 5, in step 526, after the translation operators are defined, sets of translated expansion coefficients are constructed for the first molecular subset 602 from the sets of reference expansion coefficients for the first charge density function and the first electrostatic potential field of molecular subset 602. The term "translated expansion coefficients" generally refers to a set of expansion coefficients obtained by applying a translation operator to another set of expansion coefficients.

As discussed above, step 514 provides for an axial sampling scheme comprised of axial sample points, which delimit the allowed values of the intermolecular separation, R, in FIG. 9 as applied to the relative translation of the two molecular subsets. In order to account for all allowed relative translations of the two molecular subsets, it is necessary to compute a set of translated expansion coefficients for both the first charge density function and the first electrostatic potential field of the first molecular subset 602, $$\{\tilde{\rho}^1_{nlm}(R = R_i)\} \text{ and } \{\tilde{\varphi}^1_{nlm}(R = R_i)\},$$

corresponding to each distinct axial sample point, $R_i$, in the axial sampling scheme.

As discussed above, this is accomplished via direct application of a translation operator in the form of a matrix multiplication to the reference sets of expansion coefficients for the first molecular subset 602, $$\{\rho^1_{nlm}(R = 0)\} \text{ and } \{\varphi^1_{nlm}(R = 0)\}.$$

In one embodiment, where the radial/spherical harmonics expansion of Eqn. 23 is utilized, Eqn. 35 governs the construction of $$\{\tilde{\rho}^1_{nlm}(R = R_i)\} \text{ and } \{\tilde{\varphi}^1_{nlm}(R = R_i)\}$$

for all axial sample points. Any and all permutations of the order in which axial sample points are visited is permitted, so long as in the end the construction is completed for all axial sample points.

In another embodiment, molecular subset 602 is held fixed, and the translation operator is directly applied instead to the reference sets of expansion coefficients for the second charge density function and the second electrostatic potential field of the second molecular subset 652, $$\{\rho^2_{nlm}(R = 0)\} \text{ and } \{\varphi^2_{nlm}(R = 0)\}.$$

Since only relative translation of the two molecular subsets in meaningful, it is necessary to apply the translation operator to the coordinate based representations for ρ and φ for only one of the two molecular subsets.

In FIG. 5, in step 528, after the rotation operators are defined, sets of rotated expansion coefficients are constructed for the second molecular subset 652 from the sets of reference expansion coefficients for the second charge density function and the second electrostatic potential field of molecular subset 652. The term "rotated expansion coefficients" generally refers to a set of expansion coefficients obtained by applying a rotation operator to another set of expansion coefficients. As discussed above, step 516 provides for a second spherical sampling scheme comprised of spherical sample points which delimit the allowed values of the pitch and yaw Euler angles, $(\beta_2, \gamma_2)$, in FIG. 9 as applied to orientation of the second molecular subset 652. Also as discussed above, step 518 provides for an angular sampling scheme comprised of angular sample points which delimit the allowed values of the roll Euler angle, $\alpha_2$, in FIG. 9 as applied to rotation of the second molecular subset 652 with respect the joint z-axis.

In order to account for all allowed orientations of the second molecular subset 652, it is necessary to compute a set of rotated expansion coefficients for the second charge density function and the second electrostatic potential field of the second molecular subset 652, $$\{\tilde{\rho}^2_{lmn}(\alpha_2 = \alpha_{2i}, \beta_2 = \beta_{2j}, \gamma_2 = \gamma_{2k})\} \text{ and}$$

$$\{\tilde{\varphi}^2_{lmn}(\alpha_2 = \alpha_{2i}, \beta_2 = \beta_{2j}, \gamma_2 = \gamma_{2k})\},$$

corresponding to each distinct angular sample point, $\alpha_{2i}$, in the angular sampling scheme and each distinct spherical sample point, $(\beta_{2j}, \gamma_{2k})$, in the second spherical sampling scheme, i.e., $(\alpha_{2i}, \beta_{2j}, \gamma_{2k}) \in$ Cartesian product of the angular sampling scheme and the second spherical sampling scheme.

As discussed above, this computation is accomplished via direct application of a rotation operator in the form of a matrix multiplication to the reference sets of expansion coefficients for the second molecular subset 652, $$\{\rho^2_{nlm}\} \text{ and } \{\varphi^2_{nlm}\}.$$

In one embodiment, where the radial/spherical harmonics expansion of Eqn. 23 is utilized, Eqn. 35 governs the construction of $$\{\tilde{\rho}_{lmn}^2(\alpha_2 = \alpha_{2i}, \beta_2 = \beta_{2j}, \gamma_2 = \gamma_{2k})\} \text{ and}$$

$$\{\tilde{\varphi}_{lmn}^2(\alpha_2 = \alpha_{2i}, \beta_2 = \beta_{2j}, \gamma_2 = \gamma_{2k})\}$$

for all ($\alpha_{2i}$, $\beta_{2u}$, $\gamma_{2k}$) ∈ Cartesian product of the angular sampling scheme and the second spherical sampling scheme. Any and all permutations of the order in which each ($\alpha_{2i}$, $\beta_{2j}$, $\gamma_{2k}$) is visited is permitted, so long as in the end the construction is completed for all permitted ($\alpha_{2i}$, $\beta_{2j}$, $\gamma_{2k}$). Also as discussed above, in one embodiment the construction can be accomplished by two distinct rotational operators, the first a function of the pitch and yaw Euler angles, ($\beta_2$, $\gamma_2$), and the second a function solely of the roll Euler angle, $\alpha_2$. Moreover, in another embodiment, the latter operator (designated previously as the "third rotation operator") can be deferred until generation of electrostatic energy affinity, as described below.

In FIG. 5, in step 529, sets of transformed expansion coefficients are constructed for the first molecular subset 602 from the sets of translated expansion coefficients generated in FIG. 5, step 524, for the first charge density function and the first electrostatic potential field of molecular subset 602. The term "transformed expansion coefficients" generally refers to a set of expansion coefficients obtained by applying an operator representing an arbitrary linear transformation on another set of expansion coefficients. This linear transformation may be the composition of one or more translation and/or rotation operators.

As discussed above, step 516 provides for a first spherical sampling scheme comprised of spherical sample points which delimit the allowed values of the pitch and yaw Euler angles, ($\beta_1$, $\gamma_1$), in FIG. 9 as applied to orientation of the first molecular subset 602. As discussed above, in regard to step 524, each set of translated expansion coefficients corresponds to an axial sample point of an axial sampling scheme which delimits the allowed values of the intermolecular separation, R, in FIG. 9 as applied to the relative translation of the two molecular subsets. In order to account for all allowed configurations (both orientations and relative translation) of the first molecular subset 602, it is necessary to compute a set of transformed expansion coefficients for both the first charge density function and the first electrostatic potential field of the first molecular subset 602, $$\{\tilde{\rho}_{nlm}^1(R = R_i, \alpha_1 = 0, \beta_1 = \beta_{1j}, \gamma_1 = \gamma_{1k})\} \text{ and}$$

$$\{\tilde{\varphi}_{nlm}^1(R = R_i, \alpha_1 = 0, \beta_1 = \beta_{1j}, \gamma_1 = \gamma_{1k})\},$$

corresponding to each distinct axial sample point, $R_i$, in the axial sampling scheme and each distinct spherical sample point, ($\beta_{1j}$, $\gamma_{1k}$), in the first spherical sampling scheme, i.e., ($R_i$, $\alpha_1=0$, $\beta_{1j}$, $\gamma_{1k}$) ∈ Cartesian product of the axial sampling scheme and the first spherical sampling scheme.

As discussed above, this computation is accomplished via direct application of a first rotation operator in the form of a matrix multiplication to the translated sets of expansion coefficients of step 524 for the first molecular subset 602, $$\{\tilde{\rho}_{nlm}^1(R = R_i)\} \text{ and } \{\tilde{\varphi}_{nlm}^1(R = R_i)\}.$$

In one embodiment, where the radial/spherical harmonics expansion of Eqn. 23 is utilized, a variant of Eqn. 35 governs the construction of $$\{\tilde{\rho}_{nlm}^1(R = R_i, \alpha_1 = 0, \beta_1 = \beta_{1j}, \gamma_1 = \gamma_{1k})\} \text{ and}$$

$$\{\tilde{\varphi}_{nlm}^1(R = R_i, \alpha_1 = 0, \beta_1 = \beta_{1j}, \gamma_1 = \gamma_{1k})\}$$

in terms, respectively, of $$\{\tilde{\rho}_{nlm}^1(R = R_i)\} \text{ and } \{\tilde{\varphi}_{nlm}^1(R = R_i)\}$$

for all ($R_i$, $\alpha_1=0$, $\beta_{1j}$, $\gamma_{1k}$) ∈ Cartesian product of the axial sampling scheme and the first spherical sampling scheme. Any and all permutations of the order in which the ($R_i$, $\alpha_1=0$, $\beta_{1j}$, $\gamma_{1k}$) are visited are permitted, so long as in the end the construction is completed for all permitted ($R_i$, $\alpha_1=0$, $\beta_{1j}$, $\gamma_{1k}$).

Due to commutativity, the transformed coefficients for the first molecular subset 602 can be generated by the application of the first rotation operator and the translation operator in any order. Operations are "commutative" if the order in which they are done does not affect the results of the operations. In one embodiment, as the first rotation operator commutes with the translation operator, the first rotation operator is applied to the set of reference expansion coefficients, in order to generate sets of rotated coefficients first charge density function and the first electrostatic potential field for the first molecular subset 602, in a manner similar to step 526 for the second molecular subset 652.

However, in general, it is more efficient in terms of computations (and potential storage) to generate sets of translated coefficients for one axial sample point at a time and to then subsequently apply the first rotation operator in order to generate the sets of transformed coefficients for the first molecular subset 602.

In FIG. 5, in step 530, an electrostatic energy affinity is defined. As used herein, the "electrostatic affinity score" is a representation of the change in total electrostatic energy of a system going from a state of two molecular subsets in isolation in an ambient environment (e.g., state 445 in FIG. 4) to the potential formation of a molecular complex comprised of the two molecular subsets in close proximity at a relative orientation and position to one another and embedded in the same ambient medium (e.g., state 455 in FIG. 4). In order for the present invention to perform a dense search in the conformational space of the two molecular subsets treated as rigid bodies, i.e., for possibly millions of relative orientations and translations of the two molecular subsets, in an efficient manner, the "electrostatic affinity score" is intended to be an accurate approximation of the relevant change in electrostatic energy, e.g., $\Delta E = E_{455} - E_{445}$ of FIG. 4 and eqns. 8–9.

In one embodiment, the self-electrostatic energies of both molecular subset 602 and molecular subset 652 are assumed to be nearly the same before (i.e., in relative isolation) and after the formation of a potential molecular complex. Such an approximation justifies the previously described embodiments where the computational domains 608 and 658 do not include points internal to their respective molecular surfaces 606 and 656.

However, in some cases it is plausible to approximate the total electrostatic potential, $\Phi''$, in Eqn. 9 as two linearly super-imposable potentials, $\Phi_1''$ and $\Phi_2''$, each generated separately by the charge distribution of on one of the molecular subsets, while the charge distribution on the other molecular subset is ignored, though both potentials will be different from their counterparts, $\Phi_1'$ and $\Phi_2'$, in state 445.

Such an approximation of the total electrostatic potential, $\Phi''$, is suitable when either (a) there is no ionic atmosphere comprised of one or more electrolytes present in the ambient medium, i.e., Eqn. 11 for the Poisson equation is applicable, (b) the interaction of solute entities on molecular subsets 602 and 652 with an existing ionic atmosphere in the ambient medium can be ignored due to the Debye-Huckel parameter, as defined in regard to eqns. 12–13, being very small at all points of the system, or (c) the original $\Phi$" is relatively small everywhere so that the linearized version of for the Poisson Boltzmann equation, as shown in Eqn. 13, is applicable.

To this effect, in some embodiments, the mutual electrostatic interaction between molecular subsets 602 and 652 in state 455 of FIG. 4 is approximated by representing the total electrostatic potential, $\Phi$", appearing in Eqn. 9, in terms of a linear superposition of two electrostatic potential functions, $\Phi_1$" and $\Phi_2$", respectively for molecular subsets 602 and 652. In another embodiment the aforementioned linear superposition is a direct sum.

In another embodiment, when super-position is appropriate, $\Phi_1$" and $\Phi_2$" are replaced by $\Phi_1$' and $\Phi_2$', the electrostatic potential functions for each molecular subset when in isolation as defined in regard to Eqn. 8 for state 445 of FIG. 4. Such an approximation means that changes in both the solvent screening and the self-reaction field of each charge distribution with the ambient polarizable medium as a result of changes in the relative position and orientation of the two molecular subsets are ignored.

In yet another embodiment, $\Phi_1$' and $\Phi_2$' are instead replaced by the coordinate based representations of the two electrostatic potential fields, respectively $\phi_1$ and $\phi_2$, defined in step 508 of FIG. 5 in regard to molecular subsets 602 and 652.

In one embodiment, the "electrostatic affinity score" is defined as follows:

$$\Delta E = \frac{C_1}{2} \int (\rho_1 \varphi_2 + \rho_2 \varphi_1) dV + c_2 \qquad \text{[Eqn. 39]}$$

where dV represents a differential volume element in the joint coordinate system of FIG. 9 and $c_1$ and $c_2$ are empirical constants. In Eqn. 39, $\rho_1$ and $\rho_2$ are, respectively, the coordinate based representations of the first and second charge density functions of molecular subset 602 and 652 and, as described earlier, may take on various forms according to different embodiments. In Eqn. 39, $\phi_1$ and $\phi_2$ are respectively the coordinate based representations of the first and second electrostatic potential fields of molecular subset 602 and 652 and, as described earlier, may take on various forms according to different embodiments. As already described, Eqn. 9 represents and approximation of the change in total electrostatic energy of the system comprised of the two molecular subsets and an ambient medium upon formation of a potential molecular complex, e.g., $\Delta E = E_{455} - E_{445}$ of FIG. 4 and eqns. 8–9.

The electrostatic affinity score of Eqn. 39 represents a correlation between the first charge density function of the first molecular subset 602 with the second electrostatic potential field of the second molecular subset 652, and a correlation between the second charge density function of the second molecular subset 652 with the first electrostatic potential field of the first molecular subset 602. This correlation represents the electrostatic affinity score of both molecular subsets for one relative position and orientation of their coordinate based representations in the joint coordinate system of FIG. 9.

Figure 14A:
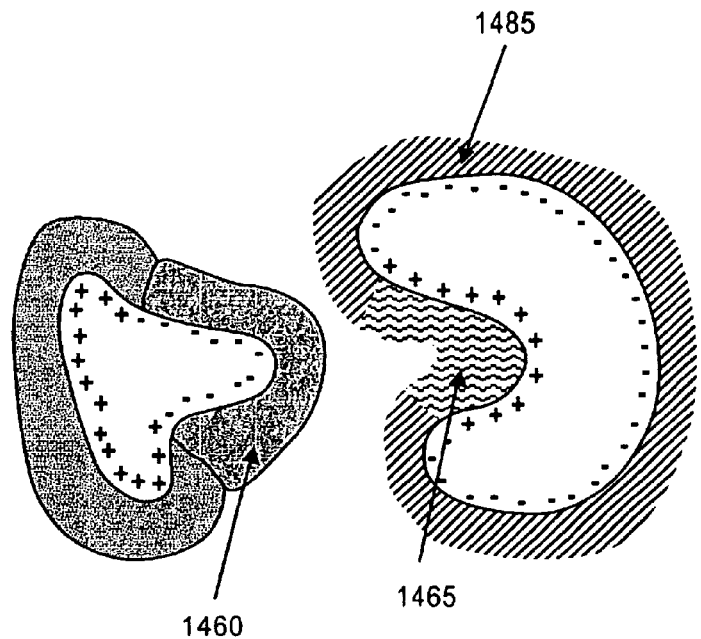
FIG. 14 shows two molecular subsets in various configurations, i.e., having various relative translations and orientations to one another, for computing electrostatic affinity scores, in accordance with embodiments of the present invention.
Figure 14B:
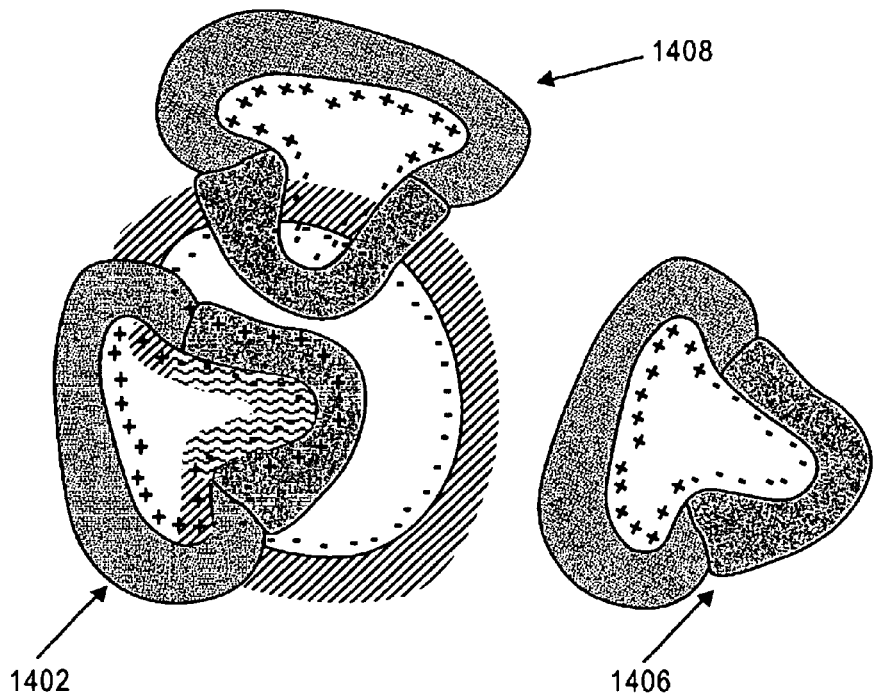

Electrostatic affinity scores are computed for different relative positions and orientations of the first and second molecular subsets 602 and 652, as shown in FIG. 14. In some embodiments, a good score, i.e., a negative value of significant magnitude, is generated when a region such as 1460 with a strong electrostatic potential field of one molecular subset overlaps with a region such as 1465 containing strong net charge of opposite sign as represented by the charge density function of the other molecular subset, such as when the molecular subsets are oriented and positioned as indicated by reference numeral 1402, thus representing better electrostatic affinity score. Poorer scores, i.e., near zero or even positive are generally calculated when there is either little or no overlap, as indicated by reference numeral 1406, or when a region such as 1480 with a strong electrostatic potential field of one molecular subset overlaps with a region such as 1485 containing strong net charge of the same sign as represented by the charge density function of the other molecular subset, such as when the molecular subsets are oriented and positioned as indicated by reference numeral 1408.

Continuing in FIG. 5, in step 532, a plurality of electrostatic affinity scores are generated by iterating over the set of sampled configurations for the molecular combination, where the set of sampled configurations is the Cartesian product of the set of sampled poses for the first molecular subset and the set of sampled poses for the second molecular subset. The iteration over the set of sampled configurations for the molecular combination, for the purpose of generating the plurality of electrostatic affinity scores, can be performed in any order.

In one embodiment, the prediction of the binding mode is generally decided based on the particular configuration, i.e., relative position and orientation, that yields the highest electrostatic affinity score. In another embodiment, the magnitude of the best score, or the top x % of scores, determines the results of the analysis of the molecular combination of the two molecular subsets. In another embodiment, all electrostatic affinity scores below a preset numerical threshold are rejected, and only those configurations with passing scores are retained for further analysis. In yet another embodiment, the electrostatic affinity scores are filtered based on an adaptive threshold dependent on observed statistics of the scores as they are generated. In yet another embodiment, the statistical analysis of both passing score magnitudes, as well as multidimensional clustering of the relative position and orientation coordinates of passing configurations, is used to predict the binding mode and/or assess the nature and likelihood of the molecular combination. In one embodiment, in the context of a hardware or mixed software/hardware implementation of the invention, the passing scores and their corresponding states are selected and output to memory off hardware.

In yet another embodiment, the above strategies can be used when screening a collection of second molecular subsets against the same first molecular subset 602 in order to predict potential binding modes and estimate binding affinity based on computations of electrostatic affinity, in order to select promising candidates for further downstream processing in the drug discovery pipeline.

In one embodiment, the plurality of electrostatic affinity scores is calculated at one value for the order of the expansion, $N_1$, and then the results are quantitatively analyzed according to certain decision criteria. In another embodiment, the decision criteria are based on a cluster analysis of the electrostatic affinity scores. As used herein, the term "cluster analysis" generally refers to a multivariate analysis technique that seeks to organize information about variables so that relatively homogeneous groups, or "clusters", can be formed. The clusters formed with this family of methods should be highly, internally homogenous (members from same cluster are similar to one another) and highly, externally heterogeneous (members of each cluster are not like members of other clusters).

A further plurality of electrostatic affinity scores may then be calculated at a higher value for the order of the expansion, $N_2 > N_1$, based on results of the quantitative analysis. The electrostatic affinity scores may be computed at the higher expansion order, $N_2$, only at those sample points for which the corresponding shape complementarity score computed at the lower expansion order, $N_1$, satisfies the decision criteria imposed by the aforementioned quantitative analysis.

In one embodiment, in order to accurately assess the likelihood of combination of molecular subsets 602 and 652 including those encountered in the context of screening against a series of molecular subsets from a molecule library, an augmented score, S', is defined as follows:

$$S' = S - \gamma \Delta E \qquad \text{[Eqn. 40]}$$

where S is a shape complementarity score for the two molecular subsets, for example such as defined in regard to Kita II, $\Delta E$ is the electrostatic affinity score of Eqn. 39, and $\gamma$ is a scalar constant, meant to weight the two scores relative to one another.

In one embodiment the augmented score, S', is generated for a plurality of different configurations of the molecular combination in a manner similar to that described above in regard to the electrostatic affinity score. In another embodiment, the augmented scores are generated by separately generating the shape complementarity scores and the electrostatic affinity scores for a plurality of different configurations of the molecular combination. In another embodiment, the shape complementarity and electrostatic affinity scores are generated concurrently for a plurality of different configurations of the molecular combination, thereby determining the augmented scores.

To compute S and $\Delta E$ concurrently, one option is to perform the computation in parallel using parallel processing units or elements. Those skilled in the art will appreciate that additional processing elements, as well as possible additional memory overhead and memory and/or i/o bandwidth, must be used in order to perform the computations, e.g., twice as many processing elements to do roughly twice as much work in similar amount of time. In one embodiment, the computation of shape complementarity and electrostatic affinity scores for a given configuration of the molecular combination is interleaved such that one type of score calculation is performed right after completion of another type of score calculations on one set of processing elements that support both kinds of score calculations.

In one embodiment, the above embodiments regarding the identification of passing electrostatic affinity scores can be applied to the augmented score by separately applying decision criteria to both the shape complementarity score, S, and the electrostatic affinity score, $\Delta E$, and those molecular configurations with both passing S and passing $\Delta E$ are deemed to be passing in terms of the augmented score, S'. In another embodiment, the above embodiments regarding the identification of passing electrostatic affinity scores can be directly applied to the augmented score itself.

Similarly, the above embodiments involving computation of electrostatic affinity scores in two or more passes represented by different values for the order of the basis expansion can be directly applied to the augmented score as well.

Generally, it is inefficient to directly evaluate Eqn. 39 in its integral form. By first applying a basis expansion to the coordinate based representations of the charge density functions and the electrostatic potential fields of the two molecular subsets to obtain reference sets of expansion coefficients and then using appropriate translation and rotation operators to generate sets of transformed expansion coefficients for the first molecular subset 602 corresponding to sampled poses of the first molecule, and to likewise generate sets of transformed expansion coefficients for the second molecular subset 652 corresponding to sample poses of the second molecular subset, the electrostatic affinity score, and hence the augmented score of Eqn. 40, for a given configuration of the molecular combination can be computed efficiently and to arbitrary precision based on the magnitude of N, the order of the expansion.

In one embodiment, within the context of the joint coordinate system of FIG. 9 and using the radial/spherical harmonics expansion of Eqn. 23, and also the formulations of eqns. 33–36 to construct and transform reference sets of expansions coefficients for the coordinate based representations of both the charge density functions and electrostatic potential fields for both molecular subsets 602 and 652, Eqn. 39 can be rewritten as follows:

$$\Delta E'(R, \beta_1, \gamma_1, \alpha_2, \beta_2, \gamma_2) = \sum_{nlm}^{N} \left( \hat{\rho}_{nlm}^1 \hat{\varphi}_{nlm}^2 + \hat{\varphi}_{nlm}^1 \hat{\rho}_{nlm}^2 \right) \qquad \text{[Eqn. 41]}$$

where $\Delta E'$ is the term corresponding to the integral in Eqn. 31 (ignoring the constants $c_1$ and $c_2$). The transformed expansion coefficients for the first molecular subset are evaluated at a sample point, i.e., $$\{\hat{\rho}_{nlm}^1 (R = R_i, \alpha_1 = 0, \beta_1 = \beta_{1j}, \gamma_1 = \gamma_{1k})\} \text{ and}$$

$$\{\hat{\varphi}_{nlm}^1 (R = R_i, \alpha_1 = 0, \beta_1 = \beta_{1j}, \gamma_1 = \gamma_{1k})\}$$

and the rotated expansion coefficients for the second molecular subset are evaluated at a sample point, i.e., $$\{\hat{\rho}_{lmn}^2 (\alpha_2 = \alpha_{2i}, \beta_2 = \beta_{2j}, \gamma_2 = \gamma_{2k})\} \text{ and}$$

$$\{\hat{\varphi}_{lmn}^2 (\alpha_2 = \alpha_{2i}, \beta_2 = \beta_{2j}, \gamma_2 = \gamma_{2k})\}.$$

In the embodiment where the third rotation operator is directly applied to the computed electrostatic affinity scores themselves, the score may be computed in two steps. In the first step, two intermediate factors $\Lambda_m^+$ and $\Lambda_m^+$ are computed, $$\Lambda_m^+ = \sum_{nlm}^{N} \left( \hat{\rho}_{nlm}^1 \hat{\varphi}_{nlm}^2 + \hat{\varphi}_{nlm}^1 \hat{\rho}_{nlm}^2 \right) \qquad \text{[Eqn. 42]}$$

$$\Lambda_m^- = \sum_{nlm}^{N} \left( \hat{\rho}_{nlm}^1 \hat{\varphi}_{nl\overline{m}}^2 + \hat{\varphi}_{nlm}^1 \hat{\rho}_{nl\overline{m}}^2 \right)$$

where $\overline{m}$ denote the negative value of m, the transformed expansion coefficients for the first molecular subset are as before $$\{\hat{\rho}_{nlm}^1 (R = R_i, \alpha_1 = 0, \beta_1 = \beta_{1j}, \gamma_1 = \gamma_{1k})\}$$

$$\text{and } \{\hat{\varphi}_{nlm}^1 (R = R_i, \alpha_1 = 0, \beta_1 = \beta_{1j}, \gamma_1 = \gamma_{1k})\}$$

but the rotated expansion coefficients for the second molecular subset are evaluated at a sample point based on application of the second rotation operator alone, i.e., $\{\tilde{p}_{lmn}^2(\alpha_2 = 0, \beta_2 = \beta_{2j}, \gamma_2 = \gamma_{2k})\}$ and $\{\tilde{\varphi}_{lmn}^2(\alpha_2 = 0, \beta_2 = \beta_{2j}, \gamma_2 = \gamma_{2k})\}$.

In the second step, the electrostatic affinity score is given by, $$\Delta E'(R, \beta_1, \gamma_1, \alpha_2, \beta_2, \gamma_2) = \sum_{m=-l}^{m=+l} (\Lambda_m^+ \cos(m\alpha_2) + \Lambda_m^- \sin(\bar{m}\alpha_2)) \quad \text{[Eqn. 43]}$$

where m is the azimuthal quantum number, and $\alpha_2$ represents the angular value associated with the third rotation operator. Splitting off the third rotation operator in the above manner generally reduces the total computation significantly.

As described above, a plurality of electrostatic affinity scores is generated for each existing element of the set of sampled configurations of the molecular combination, and can be generated in any order. In FIG. 9, this represents a sampling of electrostatic affinity scores over a six-dimensional space representing the relative positions and orientations of the two molecular subsets as given by $\{(R=R_i, \beta_1=\beta_{1j}, \gamma_1=\gamma_{1k}, \alpha_2=\alpha_{2l}, \beta_2=\beta_{2m}, \gamma_2=\gamma_{2n})\}$ where $\{R_1\}$ refers to the elements of the axial sampling scheme of step 514, $\{\beta_{1j},\gamma_{1k}\}$ to the elements of the first spherical sampling scheme of step 516, $\{\beta_{2m},\gamma_{2n}\}$ to the elements of the second spherical sampling scheme, (also of step 516), and $\{\alpha_{2l}\}$ to the elements of the angular sampling scheme of step 518.

In another embodiment, a plurality of augmented scores, as defined in Eqn. 40, are generated in a similar manner, using Eqn. 41, or alternatively eqns. 42–43, for the electrostatic affinity score and analogous expressions for the shape complementarity score as discussed previously in regard to Kita II. As described above, the shape complementarity and electrostatic affinity scores may be constructed concurrently or separately, though the choice will have direct implications on the feasibility of various embodiments for identification of passing augmented scores, also discussed above.

For reasonable sampling resolution for each sampling scheme, the total number of electrostatic affinity score scores can be very large. For example, if there are 50 axial sample points, each 1 Å apart, 1000 first spherical sample points from an icosahedral mesh, 1000 second spherical sample points from an icosahedral mesh, and 100 angular sample points, this represents approximately five billion scores. However, reduction of the sampling resolution can lead to unacceptable inaccuracies in the final prediction and characterization of the optimal binding mode for the two molecular subsets. Thus efficiency in performing the repeated computation of Eqn. 41, or alternatively eqns. 42–43, for $\Delta E'=\Delta E'(R,\beta_1,\gamma_1,\alpha_2,\beta_2,\gamma_2)$ for each sampled configuration is important, whether it be accomplished using computer software and/or hardware. In other embodiments, as discussed below, the method provides for further increased computational efficiency when considering the screening of a collection of molecular subsets from a molecule library against the same first molecular subset 602.

In order to increase efficiency when there is more prior knowledge about the first molecular subset 602, in one embodiment, the computation of electrostatic affinity scores is restricted to a subset of the possible orientations of the first molecular subset by constraining the first spherical sample points to a subset of the surface of the unit sphere. In another embodiment, the computation of electrostatic affinity scores can be restricted to a subset of the possible orientations of the first molecular subset by placing limits on the pitch and yaw Euler angles for the first molecular subset. In another embodiment, when the first molecular subset 602 includes a biopolymer with one or more known active sites, the computation of electrostatic affinity is restricted to a subset of possible orientations of the first molecular subset by constraining the first spherical sample points to those that lie with the active site.

In the context of large-scale screening, often little prior knowledge is known about the binding kinetics of the second molecular subset, however, if prior knowledge is available, in one embodiment the computation of electrostatic affinity scores is further restricted to a subset of the possible orientations of the second molecular subset by placing limits on the angular sample points for the second molecular subset and/or placing limits on the roll, pitch, and yaw Euler angles for the second molecular subset.

In other embodiments, the aforementioned embodiments regarding restriction of computation of electrostatic affinity scores to a subset of possible configurations for the molecular combination based on prior knowledge can be applied to the computation of augmented scores by similarly restricting the computation of shape complementarity and electrostatic affinity scores, whether performed concurrently or separately, to a subset of possible configurations of the molecular combination.

In order to increase computational efficiency regardless of prior knowledge, one embodiment of the current invention employs a strategy as shown in FIG. 15. Step 1520 corresponds to the direct application of the translation operator to the set of reference expansion coefficients for the first charge density function and first electrostatic potential field of molecular subset 602 in order to generate a set of translated coefficients, i.e., $\{\tilde{p}_{nlm}^1(R = R_i)\}$ and $\{\tilde{\varphi}_{nlm}^1(R = R_i)\}$ at each distinct axial sample point, $R_i$. Step 1525 shows the complete set of translated coefficients for molecular subset 602 generated in 1520, corresponding to all axial sample points, $\{R_i\}$, being subsequently stored on a computer-readable and recordable medium.

In FIG. 15, step 1530 then shows the entire set of electrostatic affinity scores being constructed for one specifically chosen axial sample point, $R_{i0}$, in the following manner. First all of the translated expansion coefficients for the first charge density function and first electrostatic potential field of molecular subset 602 corresponding to the chosen axial sample point, $R_{i0}$, are retrieved from the storage medium of step 1525 in step 1540. Then, in step 1550, the second rotation operator is applied to the set of reference expansion coefficients for the second charge density function and second electrostatic potential field of molecular subset 652 in order to generate a set of rotated coefficients, i.e., $\{\tilde{p}_{lmn}^2(\beta_2 = \beta_{2j0}, \gamma_2 = \gamma_{2k0})\}$ and $\{\tilde{\varphi}_{lmn}^2(\beta_2 = \beta_{2j0}, \gamma_2 = \gamma_{2k0})\}$ at a given second spherical sample point distinct $(\beta_{2j0}, \gamma_{2k0})$. Then, in step 1560, the first rotation operator corresponding to a specific change in orientation by $(\beta_{1j0}, \gamma_{1k0})$, is applied to each set of translated coefficients retrieved in step 1540, generating corresponding sets of transformed coefficients for first charge density function and first electrostatic potential field of molecular subset 602, i.e., $\{\tilde{p}^1_{nlm}(R = R_{i0}, \beta_1 = \beta_{1j0}, \gamma_1 = \gamma_{1k0})\}$ and $\{\tilde{\varphi}^1_{nlm}(R = R_{i0}, \beta_1 = \beta_{1j0}, \gamma_i = \gamma_{1k0})\}$ for one axial sample point, $R_{i0}$, and for one specific first spherical sample point $(\beta_{1j0}, \gamma_{1k0})$.

Then continuing with the description of step 1530, a set of transformed coefficients from step 1560 and a set of rotated coefficients from step 1550 are combined in step 1570 in order to compute a single electrostatic affinity score corresponding to $\{\Delta E'_{(i0,j0,k0,m0,n0)} = \Delta E'(R=R_{i0}, \beta_1=\beta_{1j0}, \gamma_1=\gamma_{1k0}, \beta_2=\beta_{2m0}, \gamma_2=\gamma_{2n0})\}$ for one axial sample point, $R_{i0}$, one first spherical sample point $(\beta_{2j0}, \gamma_{2k0})$, and one second spherical sample point $(\beta_{2j0}, \gamma_{2k0})$, according to Eqn. 41 or an alternative form such as in eqns. 42–43. In step 1580, only necessary if step 1570 utilized eqns. 42–43 as opposed to Eqn. 41, the third rotation operator is applied directly to the scores obtained in step 1570, according to Eqn. 43, in order to construct a set of scores corresponding to $\{\Delta E'_{(i0,j0,k0,1,m0,n0)} = \Delta E'(R=R_{i0}, \beta_1=\beta_{1j0}, \gamma_1=\gamma_{1k0}, \alpha_2=\alpha_{2l}, \beta_2=\beta_{2m0}, \gamma_2=\gamma_{2m0})\}$ for one axial sample point, $R_{i0}$, one first spherical sample point $(\beta_{2j0}, \gamma_{2k0})$, one second spherical sample point $(\beta_{2j0}, \gamma_{2k0})$, and all angular sample points $(\alpha_{2l})$ describing rotation of molecular subset 652 around the z-axis of the joint coordinate system shown in FIG. 9. In step 1590, in immediate succession, the resultant scores from step 1580, or step 1570 if 1580 was skipped, are delivered for application of various decision criteria as described above.

Steps 1550, 1560, 1570, 1580, and 1590 are then repeated multiple times in order to generate the entire set of electrostatic affinity scores for one specifically chosen axial sample point, $R_{i0}$, i.e., $\{\Delta E'_{(i0,j,k,l,m,n)} = \Delta E'(R=R_{i0}, \beta_1=\beta_{1j}, \gamma_1=\gamma_{1k}, \alpha_2=\alpha_{2l}, \beta_2=\beta_{2m}, \gamma_2=\gamma_{2n})\}$ for one axial sample point, $R_{i0}$, all first spherical sample points $(\beta_{2j}, \gamma_{2k})$, all second spherical sample points $(\beta_{2j}, \gamma_{2k})$, and all angular sample points $(\alpha_{2l})$. The number of repetitions of steps 1550 and 1560 depends on the order in which the individual scores in step 1570 are computed. The entirety of step 1530 (including steps 1540, 1550, 1560, 1570, 1580, and 1590) is then repeated for another distinct axial sample point, $R_i$, and so on for all axial sample points in $\{R_i\}$.

In one embodiment, step 1580 can be skipped if instead the third rotation operator was included in step 1550 as part of a composite rotation matrix, as previously discussed. Moreover, in another embodiment, steps 1550 and 1560 may instead calculate sets of coefficients for more than one spherical sample point at a time, depending on the usage of computer-readable memory to store intermediate results.

In another embodiment, since it is impractical to perform steps 1550 and 1560 one at a time for each score generated in 1570, steps 1550 and 1560 are performed concurrently A times and pipelined in front of step 1570, in order to feed the input requirements for generating A*A scores in step 1570. In another embodiment step 1550 is performed A times and step 1560 is performed B times, the results of which are stored in an intermediate computer-readable memory and pipelined in front of step 1570, in order to feed the input requirements for generating A*B scores in step 1570.

In yet another embodiment, step 1540 is performed in a pipelined fashion using an intermediate computer-addressable memory so that the sets of translation coefficients corresponding to the next axial sample point are read in concurrently while performing one pass of step 1530. In another embodiment, for the purposes of hardware architecture, the entire set of translated coefficients generated in step 1520 are directly stored in on-chip computer-readable memory in step 1525 as opposed to off-chip computer-readable memory. In another embodiment, step 1530 performs the calculation of electrostatic affinity scores for more than one axial sample point in parallel and in a concurrent fashion. In another embodiment step 1525 is skipped, and the translation operator is directly applied before the initiation of one pass through step 1530.

In certain alternative embodiments, initially sets of rotated expansion coefficients corresponding to each molecular subset are formed via direct application of an appropriate rotation operator to the sets of reference expansion coefficients for the corresponding charge density functions and electrostatic potential fields. The resultant sets of rotated expansion coefficients are respectively computed for all points of the first and second sampling schemes and then stored on a computer-recordable medium.

The remaining steps of these alternative embodiments are similar to that discussed in FIG. 15 in regard to the iterated step 1530 (comprising steps 1540, 1550, 1560, 1570, 1580, and 1590) with the following two exceptions. First, step 1540 now involves the retrieval of rotated expansion coefficients for both molecular subsets. Second, step 1560 now involves application of a translation operator corresponding to the current axial sample point to the rotated expansion coefficients for the molecular subset 602 in order to form a set of translated expansion coefficients for molecular subset 602. From there the iteration over all sampled configurations may proceed in any order (e.g., axial loop is the outer loop vs. orientation loop on the outside), though as discussed in Kita II similar styles of embodiments involving pregeneration of rotated expansion coefficients when applied to shape complementarity computations are significantly more costly computationally than their FIG. 15 counterparts.

For the embodiments displayed in FIG. 15, as well as the aforementioned alternative embodiments that interchange the order of application of translation and rotation operators, it is possible to compute augmented scores as per Eqn. 40. Kita II provides detailed discussions regarding analysis of molecular combinations based on computation of shape complementarity scores via basis expansions.

In some embodiments, architectural components involving charge density may be only slightly modified in order to also handle the internal volumetric function, $\tau$, and similarly the architectural components involving the electrostatic potential field are only slightly modified in order to handle the external volumetric function, $\sigma$, in order to generate shape complementarity scores either in parallel or in a sequential or even interleaved manner.

In one embodiment, the shape complementarity scores are calculated using separate architectural components from those used to calculate the electrostatic affinity score, and the calculations are effectively parallelized in such a way that the combined augmented score for a given relative configuration of the system can be thresholded jointly, i.e., storage buffer requirements for individual shape complementarity and electrostatic affinity scores are minimal.

In another embodiment, the shape complementarity and electrostatic affinity scores are computed in an interleaved fashion using the same, or nearly identical (with some specialized modifications) architectural components so that any given time the calculation pipeline is alternating between generation of shape complementarity and electrostatic affinity scores and joint thresholding can be performed in an optimal fashion.

Joint thresholding of both the shape complementarity and electrostatic affinity scores is often important since, as discussed above, it is difficult to judge optimal binding modes based on only the shape complementarity or the electrostatic affinity score alone. Yet performing calculations for the shape complementarity and electrostatic affinity scores separately and not in a parallelized or interleaved fashion would necessitate excessively large memory buffers and/or I/O or DRAM bandwidth for any significantly high density search over the configuration space.

Among other things, embodiments of the present invention also provide for precomputation of translation expansion coefficients for both the charge density function and the electrostatic potential field of a molecular subset. These translation expansion coefficients can then be stored on a computer-readable medium. Then before computing electrostatic affinity scores, the stored translated expansion coefficients can be retrieved as needed for each distinct axial sample point, corresponding to a different relative translation of the two molecular subsets. In one embodiment, in the context of a hardware or a mixed software/hardware implementation of the present invention the translation expansion coefficients are stored off-chip. In another embodiment the translation expansion coefficients are stored on-chip for faster access.

In the context of analysis of a molecular combination, the translation can be applied once to a set of reference coefficients for the first charge density function and the first electrostatic potential field of molecular subset 602 for a finite number of translation values, performed off-chip, and the results stored for subsequent use in screening against a series of second molecular subsets selected from a molecule library or other collection. As already mentioned, the molecule library is generally a database, plurality of databases, or other storage media in which a plurality of digital representations of molecular subsets are stored.

Those skilled in the art should be aware that the methodology described above is applicable to a wide variety of correlation-based score calculations. In addition to electrostatic affinity score calculations described above, the methods are equally applicable to many other correlation-based score calculations based on volumetric functions associated with molecular subsets in the context of a high density search over relative orientations and positions of the two molecular subsets.

It will be understood that the above described arrangements of apparatus and the method there from are merely illustrative of applications of the principles of this invention and many other embodiments and modifications may be made without departing from the spirit and scope of the invention as defined in the claims.

What is claimed is:

1. A method of computing electrostatic affinity for a set of molecular configurations of a molecular combination, wherein the molecular combination includes at least a first molecular subset and a second molecular subset, the method comprising:

defining, for each of the first and second molecular subsets:
1) a charge distribution based on a plurality of atoms and bonds forming the molecular subset or a portion thereof;
2) a molecular surface based on locations of a plurality of surface atoms of the molecular subset; and
3) an electrostatic potential function based on the electrostatic interaction of the corresponding charge distribution of the molecular subset with itself and with charges associated with an ambient environment of the molecular subset in isolation;

generating a charge density function for each molecular subset as a representation of the corresponding charge distribution of the molecular subset over a subset of a volume enclosed by the corresponding molecular surface;

defining an electrostatic potential computational domain for each molecular subset that encloses a subset of the volume external to the corresponding molecular surface, including positions that are proximal to the molecular surface;

generating an electrostatic potential field for each molecular subset as a representation of the corresponding electrostatic potential function over the corresponding electrostatic potential computational domain;

defining a coordinate-based representation for the first molecular subset in a first coordinate system;

defining a coordinate-based representation for the second molecular subset in a second coordinate system distinct from the first coordinate system;

placing the coordinate-based representations of the first and second molecular subsets in a joint coordinate system with separate frames for each molecular subset centered at respective molecular centers of each molecular subset, with an intermolecular axis defined therebetween and the z-axes of the frames aligned with the intermolecular axis;

obtaining a basis expansion with a set of basis functions, wherein each of the charge density functions and electrostatic potential fields are represented by a respective set of expansion coefficients, designated as a reference set for the corresponding molecular subset;

obtaining a translation operator, along with an associated axial sampling scheme comprising a plurality of axial sample points distributed along the intermolecular axis, reflecting discretized relative translation of the first molecular subset with respect to the second molecular subset in a joint coordinate system;

obtaining a first rotation operator, along with an associated first spherical sampling scheme comprising a plurality of spherical sample points distributed on the surface of a unit sphere centered on the first molecular subset, representing discretized rotation of the first molecular subset with respect to a frame located at the center of the first molecular subset;

obtaining a second rotation operator, along with an associated second spherical sampling scheme comprising a plurality of spherical sample points distributed on the surface of a unit sphere centered on the second molecular subset, representing discretized rotation of the second molecular subset with respect to a frame located at the center of the second molecular subset;

obtaining a third rotation operator, along with an associated angular sampling scheme comprising a plurality of angular sample points distributed on a circumference of a unit circle orthogonal to the intermolecular axis, representing discretized rotation of the second molecular subset with respect to the intermolecular axis;

defining an electrostatic affinity score for a molecular configuration, representing a correlation between the charge density function of the first molecular subset with the electrostatic potential field of the second molecular subset and the charge density function of the second molecular subset with the electrostatic potential field of the first molecular subset at a given relative position and orientation of the first and second molecular subsets in the associated joint coordinate system;

defining a set of sampled poses of the first molecular subset as prescribed by a Cartesian product of the axial sample points of the axial sampling scheme for the first molecular subset and the spherical sample points of the first spherical sampling scheme for the first molecular subset;

defining a set of sampled poses of the second molecular subset as prescribed by the Cartesian product of the spherical sample points of the second spherical sample scheme, and the angular sample points of the angular sampling scheme;

defining a set of sampled configurations for the molecular combination comprising the two molecular subsets as prescribed by the Cartesian product, or a subset thereof, of the set of sampled poses for the first molecular subset and the set of sampled poses for the second molecular subset;

constructing a set of transformed expansion coefficients for the first molecular subset corresponding to a set of sampled poses of the first molecular subset by applying both the translation operator and the first rotation operator to the reference set of expansion coefficients for both the first charge density function and the first electrostatic potential function for the first molecular subset;

constructing a set of transformed expansion coefficients for the second molecular subset, corresponding to a set of sampled poses for the second molecular subset by applying both the second and third rotation operators to the reference set of expansion coefficients for both the second charge density function and the second electrostatic potential function for the second molecular subset;

computing the defined electrostatic affinity score for a sampled configuration in terms of the set of transformed expansion coefficients for both the first charge density function and the first electrostatic potential field for the first molecular subset, corresponding to a sampled pose of the first molecular subset, and the set of transformed expansion coefficients for both the second charge density function and the second electrostatic potential function for the second molecular subset, corresponding to a sampled pose of the second molecular subset; and generating a plurality of electrostatic affinity scores by iterating over the set of sampled configurations of the molecular combination and generating an electrostatic affinity score for each configuration.

2. The method of claim 1, wherein the described method of computing electrostatic affinity is used as part of an analysis of a molecular combination involving computation of electrostatic affinity, or equivalent measures, for each of a set of sample configurations of the molecular combination.

3. The method of claim 1, wherein the first charge density function for the first molecular subset is defined as a union of a set of kernel functions, each kernel function associated with one of the atoms or bonds in the first molecular subset, wherein each kernel function might be dependent on the chemical identity of the associated atom or bond, wherein the kernel function might be dependent on the location of the associated atom or bond within a chemical group and wherein the kernel function is dependent on the partial or full charge of the associated atom or bond.

4. The method of claim 3, wherein the partial or full charge of the associated atom or bond is assigned based on an energy parameter set.

5. The method of claim 3, wherein the kernel function associated with an atom or bond might be nonzero for positions within a Van der Waals sphere centered on the atom or bond and zero otherwise.

6. The method of claim 5, wherein the kernel function is a nonzero constant for positions within a Van der Waals sphere centered on each atom with a value such that when multiplied by the volume of the Van der Waals sphere equals the charge assigned to the atom.

7. The method of claim 3, wherein each kernel function is the charge of the associated atom or bond multiplied by a 3-D probability distribution function centered on the atom or bond.

8. The method of claim 7, wherein the 3-D probability distribution function is a 3-D Gaussian function centered on the atom or bond and with known variance.

9. The method of claim 8, wherein the variance is dependent on the chemical identity of the associated atom or bond, wherein the variance is dependent on the location of the associated atom or bond within a chemical group and/or wherein the variance is dependent on the magnitude of the partial or full charge of the associated atom or bond.

10. The method of claim 3, wherein each kernel function is the charge of the associated atom or bond multiplied by an orthonormal radial basis function.

11. The method of claim 3, wherein each kernel function is the charge of the associated atom or bond multiplied by a Laguerre polynomial-based radial basis function, scaled or unsealed.

12. The method of claim 3, wherein each kernel function is a quantum mechanical wave function representing the charge distribution of the associated atom or bond.

13. The method of claim 3, wherein each kernel function is the charge of the associated atom or bond multiplied by a radial/spherical harmonics basis expansion of finite order of expansion representing the charge distribution of the atom or bond.

14. The method of claim 1, wherein the electrostatic potential computational domain for each molecular subset also includes a subset of the internal volume enclosed within the corresponding molecular surface.

15. The method of claim 1, wherein the electrostatic potential computational domain for each molecular subset is the volume proximal to the corresponding molecular surface that is swept by moving a probe sphere having a center which moves along the corresponding molecular surface.

16. The method of claim 15, wherein the molecular surface used in defining the electrostatic potential computational domain for each molecular subset is the solvent accessible surface.

17. The method of claim 15, wherein the probe sphere center moves along a portion of the corresponding molecular surface of each molecular subset.

18. The method of claim 15, wherein the probe sphere has a constant radius.

19. The method of claim 15, wherein the probe sphere has a radius that varies as a function of location on the corresponding molecular surface.

20. The method of claim 15, wherein the radius of the probe sphere is larger than a characteristic radius associated with one or more of the atoms or bonds that is included in either molecular subset or with one or more solvent entity that makes up the ambient environment of either molecular subset.

21. The method of claim 1, wherein the ambient environment comprises one or more solvent entities, with solvent entities including one or more of individual solvent atoms, solvent molecules, or solvent ions.

22. The method of claim 21, wherein the solvent molecules include one or more of water molecules, sugar molecules, fatty acids, salts, acids, bases, or free radicals.

23. The method of claim 1, wherein the electrostatic potential function defined for each molecular subset in isolation is a Coulombic electrostatic potential function in a homogeneous dielectric medium.

24. The method of claim 1, wherein the electrostatic potential function defined for each molecular subset in isolation is a solution to a Poisson equation with suitable boundary conditions.

25. The method of claim 1, wherein the electrostatic potential function defined for each molecular subset in isolation includes a provision for the effects of electrostatic desolvation between one or more solute charges and a surrounding ambient environment comprising solvent entities.

26. The method of claim 1, wherein the electrostatic potential function defined for each molecular subset in isolation is a solution to the Linearized Poisson-Boltzmann equation with suitable boundary conditions and one or more nonzero Debye-Huckel parameters.

27. The method of claim 1, wherein the electrostatic potential function defined for each molecular subset in isolation is obtained by employing a Generalized Born solvation model.

28. The method of claim 1, wherein the electrostatic potential function defined for each molecular subset in isolation is obtained by employing a molecular dynamics simulation with an explicit solvent dipole model.

29. The method of claim 1, wherein the coordinate based representation of each molecular subset is defined using a spherical, cylindrical or Cartesian coordinate system.

30. The method of claim 1, wherein the molecular center of each molecular subset is a center of mass or a centroid of the corresponding molecular subset.

31. The method of claim 1, wherein the joint coordinate system used in moving or rotating the coordinate based representations of the first molecular subset and the second molecular subset relative to one another is different from the joint coordinate system used in the final calculations of the electrostatic affinity scores.

32. The method of claim 1, wherein an order of the basis expansion used in representing both charge density function and the electrostatic potential field for each molecular subset has a finite value and where the finite value for the order of the basis expansion might be predetermined.

33. The method of claim 32, where the finite value for the order of the basis expansion is adaptively determined based on a quantitative analysis of basis expansion errors for trial values of the order of the basis expansion.

34. The method of claim 1, wherein the basis expansion used in representing both the charge density function and electrostatic potential field for each molecular subset is an orthogonal basis expansion comprising a plurality of mutually orthogonal or orthonormal basis functions.

35. The method of claim 1, wherein the basis expansion used in representing both the charge density function and electrostatic potential field for each molecular subset is a radial/spherical harmonics basis expansion comprising a plurality of basis functions defined as products of a set of orthonormal radial basis functions and a set of spherical harmonics basis functions.

36. The method of claim 35, wherein the radial basis functions include a mutually orthonormal set of basis functions which depend on the radius in a spherical coordinate system centered on the molecular center of the first molecular subset.

37. The method of claim 36, wherein the radial basis functions include scaled or unscaled Laguerre polynomial-based radial basis functions.

38. The method of claim 35, wherein the spherical harmonics basis functions are real-valued.

39. The method of claim 35, wherein the radial/spherical harmonics basis expansion has a finite value for the order of the expansion and the expansion coefficients, representing the charge density function or the electrostatic potential function of the molecular subset, are discretized radial/spherical harmonic expansion coefficients.

40. The method of claim 1, wherein different orientations of the coordinate based representation of the each molecular subset with respect to the Cartesian frame located at the corresponding molecular center of the molecular subset are represented by a set of three Euler angles representing roll, pitch, and yaw.

41. The method of claim 40, wherein the roll Euler angle for the first molecular subset, representing a change in orientation of the first molecular subset with respect to the z-axis of the first molecular subset's Cartesian frame, is disregarded, and different orientations of the first molecular subset are represented by a pair of Euler angles, namely the pitch and yaw Euler angles, and different orientations for the second molecular subset are represented by a full set of three Euler angles, including the roll Euler angle for the second molecular subset, representing a change in orientation of the second molecular subset with respect to the z-axis of the Cartesian frame of the second molecular subset.

42. The method of claim 40, wherein the first rotation operator for the first molecular subset is represented by a matrix function of the roll, pitch, and yaw Euler angles for the first molecular subset.

43. The method of claim 40, wherein the basis expansion of the first molecular subset is a radial/spherical harmonics basis expansion comprising a plurality of basis functions defined as products of a set of radial basis functions and a set of spherical harmonics basis functions, and the first rotation operator is a Wigner rotation matrix with indices specified in terms of quantum numbers of the radial/spherical harmonics basis expansion.

44. The method of claim 40, wherein the first rotation operator for the first molecular subset is represented by a matrix function of the pitch and yaw Euler angles for the first molecular subset, the second rotation operator for the second molecular subset is represented by a matrix function of the pitch and yaw Euler angles for the second molecular subset, and the third rotation operator for the second molecular subset is represented by a matrix function of the roll Euler angle for the second molecular subset.

45. The method of claim 44, wherein the basis expansion for each molecular subset is the radial/spherical harmonics basis expansion of claim 13 and the first and second rotation operators are Wigner rotation matrices with indices specified in terms of the quantum numbers of the basis expansion for both molecular subsets and the roll Euler angle is set to zero.

46. The method of claim 1, wherein the two successive applications of the second and third rotation operators to the coordinate based representation of the second molecular subset are combined and performed as a single combined rotation operator.

47. The method of claim 46, wherein the combined rotation operator is represented by a matrix function of roll, pitch, and yaw Euler angles for the second molecular subset and said matrix function might be a Wigner rotation matrix with indices specified in terms of quantum numbers of the basis expansion for the second molecular subset.

48. The method of claim 1, wherein the sets of transformed expansion coefficients for the charge density function and the electrostatic potential field of the second molecular subset are generated by applying only the second rotation operator, and the resultant intermediate electrostatic affinity scores are subjected to a matrix multiplication representing the third rotation operator in order to generate a plurality of final electrostatic affinity scores that represent the set of angular sample points for the second molecular subset.

49. The method for claim 48, wherein the basis expansion for each molecular subset is the radial/spherical harmonics basis expansion of claim 13 and the matrix function representing the third rotation operator as applied to electrostatic affinity scores is a function of the roll Euler angle of the second molecular subset, with indices specified by azimuthal quantum numbers of the basis expansion for both molecular subsets.

50. The method of claim 1, wherein the translation operator applied to the coordinate based representation of the first molecular subset is a matrix function of the displacement along the intermolecular axis between the two molecular subsets.

51. The method of claim 1, wherein the coordinate based representation of the charge density function of the first molecular subset is generated for a specific coordinate system, stored on a recordable medium as a set of discrete values, each discrete value representing a portion of the information representing the coordinate based representation of the charge density function of the first molecular subset, then the stored discrete values retrieved as needed when constructing a set of reference expansion coefficients for the charge density function of the first molecular subset, having first converted each discrete value into another value representing the corresponding portion of the information representing the coordinate based representation of the charge density function of the first molecular subset in a coordinate system used to define the basis expansion, the conversion being accomplished by a suitable coordinate transformation.

52. The method of claim 1, wherein the coordinate based representation of the electrostatic potential field of the first molecular subset is generated for a specific coordinate system, stored on a recordable medium as a set of discrete values, each discrete value representing a portion of the information representing the coordinate based representation of the electrostatic potential field of the first molecular subset, then the stored discrete values retrieved as needed when constructing a set of reference expansion coefficients for the electrostatic potential field of the first molecular subset, having first converted each discrete value into another value representing the corresponding portion of the information representing the coordinate based representation of the electrostatic potential field of the first molecular subset in a coordinate system used to define the basis expansion, the conversion accomplished by a suitable coordinate transformation.

53. The method of claim 1, wherein either the axial and/or the first spherical sampling schemes for the first molecular subset are regular sampling schemes.

54. The method of claim 1, wherein either the axial and/or the first spherical sampling schemes for the first molecular subset are irregular sampling schemes.

55. The method of claim 1, wherein endpoints of the axial sampling scheme for the first molecular subset are assigned based on analysis of the electrostatic potential computational domains for both molecular subsets.

56. The method of claim 55, wherein the analysis constitutes a determination of the maximum radial extent of points external to the molecular surface of each molecular subset and for which the value of the electrostatic potential field for each molecular subset in isolation is above a specified minimum threshold, and the endpoints of the axial sampling scheme for the first molecular subset are set based on a sum of the maximum radial extents determined for each molecular subset.

57. The method of claim 1, wherein the angular and/or the second spherical sampling scheme for the second molecular subset are regular sampling schemes.

58. The method of claim 1, wherein the angular and/or the second spherical sampling scheme for the second molecular subset are irregular sampling schemes.

59. The method of claim 1, wherein constructing the set of transformed expansion coefficients for the first molecular subset is accomplished by applying the first rotation operator, corresponding to the sampled orientation for the first molecular subset, to the reference set of expansion coefficients for both the charge density and electrostatic potential field for the first molecular subset, and then applying the translation operator, corresponding to an axial sample point, to the set of rotated expansions coefficients for both the charge density and electrostatic potential functions for the first molecular subset.

60. The method of claim 1, wherein constructing the set of transformed expansion coefficients for the first molecular subset is accomplished by applying the translation operator, corresponding to an axial sample point, to the reference set of expansion coefficients for both the charge density and electrostatic potential functions for the first molecular subset, and then applying the first rotation operator, corresponding to the sampled orientation for the first molecular subset to the set of translated expansions coefficients for both the charge density and electrostatic potential functions for the first molecular subset.

61. The method of claim 1, wherein the computation of electrostatic affinity scores is restricted to a subset of the possible orientations of the first molecular subset by constraining the first spherical sample points to a subset of the surface of the unit sphere.

62. The method of claim 1, wherein the computation of electrostatic affinity scores is restricted to a subset of the possible orientations of the first molecular subset by placing limits on the pitch and yaw Euler angles for the first molecular subset.

63. The method of claim 1, wherein the computation of electrostatic affinity scores is further restricted to a subset of the possible orientations of the second molecular subset by placing limits on angular sample points for the second molecular subset.

64. The method of claim 1, wherein the computation of electrostatic affinity scores is restricted to a subset of the possible orientations of the second molecular subset by placing limits on the roll, pitch, and yaw Euler angles for the second molecular subset.

65. The method of claim 1, wherein the set of computed electrostatic affinity scores is subjected to a set of decision criteria in order to select the optimal electrostatic affinity scores at corresponding positions and orientations of the two molecular subsets.

66. The method of claim 65, wherein the decision criteria is based on a preset numerical threshold.

67. The method of claim 65, wherein the decision criteria is based on an adaptive threshold dependent on observed statistics of the electrostatic affinity scores as the electrostatic affinity scores are generated.

68. The method of claim 65, wherein the decision criteria is based on a cluster analysis of the electrostatic affinity scores.

69. The method of claim 1, wherein the plurality of sets of electrostatic affinity scores are calculated at one value for the order of the expansion, the electrostatic affinity scores are quantitatively analyzed, and a further plurality of electrostatic affinity scores are calculated at a higher value for the order of the expansion based on results of an intervening analysis.

70. The method of claim 69, wherein the second plurality of electrostatic affinity scores is computed only at sample points for which an initial electrostatic affinity score satisfies a set of decision criteria in order to select the optimal electrostatic affinity scores at corresponding positions and orientations of the two molecular subsets.

71. The method of claim 1, wherein the first molecular subset includes a biopolymer or a part of a biopolymer.

72. The method of claim 1, wherein the first molecular subset includes a biopolymer with one or more known active sites, and the computation of electrostatic affinity scores is restricted to a subset of possible orientations of the first molecular subset by constraining the first spherical sample points to those that lie within the active sites.

73. The method of claim 1, wherein the first molecular subset includes one or more of a synthetic compound, a chemical group, a medicinal compound or a carbohydrate.

74. The method of claim 1, wherein the analysis of the molecular combination is determined between a first molecular subset and each of a plurality of second molecular subsets selected from a molecule library, the method comprising the additional step of storing all the sets of translated or rotated expansion coefficients for the first molecular subset on recordable media and retrieving the appropriate set of translated or rotated expansion coefficients when constructing sets of transformed expansion coefficients for the first molecular subset.

75. The method of claim 74, wherein the set of computed electrostatic affinity scores is further subjected to a set of decision criteria in order to generate an optimal electrostatic affinity score, or equivalent measure, representing the configuration with the maximal electrostatic affinity for each combination and the resultant optimal electrostatic affinity scores are then ranked according to a sorting criteria in order to prioritize those second molecular subsets selected from the molecule library that exhibit high electrostatic affinity with the first molecular subset.

76. The method of claim 74, wherein the plurality of computed electrostatic affinity scores are stored on a recordable medium, the method being repeated for further molecular combinations featuring second molecular subsets selected from the molecule library, and a cluster analysis is performed on the set of stored, electrostatic affinity scores to perform an analysis of each molecular combination of the first molecular subset with each second molecular subset selected from the molecule library.

77. The method of claim 1, wherein the set of transformed expansion coefficients for the first molecular subset corresponding to a set of sampled poses of the first molecular subset is obtained by first applying the translation operator to a set of corresponding reference expansion coefficients to form a set of translated expansion coefficients and then applying the first rotation operator to the set of translated expansion coefficients for both the charge density function and the electrostatic potential field for the first molecular subset.

78. The method of claim 77, wherein sets of translated expansion coefficients for the first molecular subset are generated for all axial sample points and stored on a recordable medium and then retrieved at the time of application of the first rotation operator in order to form the corresponding set of transformed expansion coefficients.

79. The method of claim 1, wherein the set of transformed expansion coefficients for the first molecular subset corresponding to a set of sampled poses of the first molecular subset is obtained by first applying the first rotation operator to a set of corresponding reference expansion coefficients to form a set of rotated expansion coefficients and then applying the translation operator to the set of rotated expansion coefficients for both the charge density function and the electrostatic potential field for the first molecular subset.

80. The method of claim 79, wherein sets of rotated expansion coefficients for the first molecular subset are generated for all first spherical sample points and stored on a recordable medium and then retrieved at the time of application of the translation operator in order to form the corresponding set of transformed expansion coefficients.

81. The method of claim 1, wherein the iteration over sampled configurations involves computation of electrostatic affinity scores for all joint sampled orientations of both the first and second molecular subsets for a given axial sample point, and then proceeding to repeat the process for all axial sample points.

82. The method of claim 1, wherein the electrostatic affinity score for a given sampled configuration is combined with a corresponding shape complementarity score, or equivalent measure, in order to form an augmented score reflecting both shape complementarity and electrostatic affinity for each sampled configuration of a molecular combination as part of an analysis of the molecular combination.

83. The method of claim 82, wherein the shape complementarity score is computed via utilization of basis expansions for internal and external shape volume functions.

84. The method of claim 82, wherein the combination of electrostatic affinity and shape complementarity is a linear combination.

85. The method of claim 82, wherein the set of computed electrostatic affinity scores and the set of computed shape complementarity scores are separately subjected to a set of decision criteria or thresholds in order to select optimal augmented scores at corresponding positions and orientations of the two molecular subsets.

86. The method of claim 82, wherein the set of computed electrostatic affinity scores and the set of computed shape complementarity scores are jointly subjected to a set of decision criteria or thresholds in order to select optimal augmented scores at corresponding positions and orientations of the two molecular subsets.

87. The method of claim 86, wherein for a given sampled configuration one or more electrostatic affinity scores and one or more shape complementarity scores are computed concurrently thereby facilitating the joint thresholding of the two measures at the time augment score for the given sampled configuration is constructed.

88. The method of claim 86, wherein for a given sampled configuration one or more electrostatic affinity scores and one or more shape complementarity scores are computed in an interleaved fashion thereby facilitating the joint thresholding of the two measures at the time augment score for the given sampled configuration is constructed.

89. The method of claim 1, wherein the computational system for analysis of molecular combinations based on computation of electrostatic affinity scores comprises one or more of a general purpose programmable computer-including software to implement the computational platform, dedicated hardware, firmware, or a combination thereof.

* * * * *